US011938197B2

(12) United States Patent
Alexander et al.

(10) Patent No.: US 11,938,197 B2
(45) Date of Patent: Mar. 26, 2024

(54) POLYNUCLEOTIDES AND VECTORS FOR THE EXPRESSION OF TRANSGENES

(71) Applicants: Children's Medical Research Institute, Westmead (AU); The Sydney Children's Hospitals Network (Randwick and Westmead) (incorporating The Royal Alexandra Hospital for Children), Westmead (AU)

(72) Inventors: Ian Alexander, Westmead (AU); Sharon Cunningham, Westmead (AU)

(73) Assignees: THE SYDNEY CHILDREN'S HOSPITALS NETWORK (RANDWICK AND WESTMEAD (INCORPORATING THE ROYAL ALEXANDRA HOSPITAL FOR CHILDREN), Westmead (AU); CHILDREN'S MEDICAL RESEARCH INSTITUTE, Westmead (AU)

( * ) Notice: Subject to any disclaimer, the term of this patent is extended or adjusted under 35 U.S.C. 154(b) by 421 days.

(21) Appl. No.: 16/477,168

(22) PCT Filed: Jan. 10, 2018

(86) PCT No.: PCT/AU2018/050011

§ 371 (c)(1),
(2) Date: Jul. 10, 2019

(87) PCT Pub. No.: WO2018/129586

PCT Pub. Date: Jul. 19, 2018

(65) Prior Publication Data

US 2019/0365926 A1 Dec. 5, 2019

(30) Foreign Application Priority Data

Jan. 10, 2017 (AU) ................................ 2017900050

(51) Int. Cl.
*C12N 15/67* (2006.01)
*A61K 48/00* (2006.01)
(Continued)

(52) U.S. Cl.
CPC ........ *A61K 48/0058* (2013.01); *C12N 9/1018* (2013.01); *C12N 15/67* (2013.01);
(Continued)

(58) Field of Classification Search
CPC .. A61K 48/0058; C12N 9/1018; C12N 15/67; C12N 15/86; C12N 2750/14143; C12N 2840/007; C12Y 201/03003
See application file for complete search history.

(56) References Cited

U.S. PATENT DOCUMENTS 10,660,970 B2 * 5/2020 Monahan .................. A61P 3/00
2002/0136710 A1 9/2002 Samulski et al.
(Continued)

FOREIGN PATENT DOCUMENTS

WO WO 15/139093 * 9/2015
WO WO 2015/138348 A1 9/2015
WO WO 2015/139093 A1 9/2015

OTHER PUBLICATIONS

Luksan et al, Human Mutation 31: e1294-e1303, 2010.*
(Continued)

*Primary Examiner* — Kevin K Hill
(74) *Attorney, Agent, or Firm* — Knobbe, Martens, Olson & Bear LLP

(57) ABSTRACT

Polynucleotides and vectors can be used for the expression of a transgene in cells, such as liver cells. The expression of the transgene from the polynucleotides and vectors can be useful in gene therapy. Various methods can be used for
(Continued)

pAAV2-hOTCE.hAATp(2232).SV40int.huOTCco.BGHpA

Sgfl/Kpnl/Pacl Bglll | Notl Xbal/EcoRI | EcoRV/Sall | Ahll(Spel)/Sbfl

| ITR | OTC enh | hAAT promoter (2232) | SV int | Kozak-Human OTC codon optimised | BGHpA | ITR |
|---|---|---|---|---|---|---|

pAAV2-hOTCE.hOTCp(2232).SV40int.huOTCco.BGHpA

Sgfl/Kpnl/Pacl Bglll | Notl Xbal/EcoRI | EcoRV/Sall | Ahll(Spel)/Sbfl

| ITR | OTC enh | huOTC promoter (2232) | SV int | Kozak-Human OTC codon optimised | BGHpA | ITR |
|---|---|---|---|---|---|---|

expressing the transgene from the polynucleotides and vectors in liver cells.

7 Claims, 6 Drawing Sheets

Specification includes a Sequence Listing.

(51) Int. Cl.
*C12N 9/10* (2006.01)
*C12N 15/86* (2006.01)

(52) U.S. Cl.
CPC .... *C12N 15/86* (2013.01); *C12N 2750/14143* (2013.01); *C12N 2840/007* (2013.01); *C12Y 201/03003* (2013.01)

(56) References Cited

U.S. PATENT DOCUMENTS

| | | | | |
|---|---|---|---|---|
| 2007/0161031 | A1* | 7/2007 | Trinklein | C12Q 1/6897 435/6.11 |
| 2011/0201088 | A1 | 8/2011 | Beall et al. | |
| 2014/0107185 | A1* | 4/2014 | Maclaren | C12N 9/1085 435/320.1 |
| 2015/0225717 | A1* | 8/2015 | Lee | C12N 15/111 435/375 |
| 2016/0074474 | A1* | 3/2016 | Passini | A61K 9/0085 514/44 R |
| 2016/0206750 | A1* | 7/2016 | Monahan | A01K 67/027 |
| 2016/0362687 | A1* | 12/2016 | Monia | C12N 15/113 |
| 2017/0326256 | A1* | 11/2017 | Doering | A61P 7/02 |

OTHER PUBLICATIONS

Nishiyori et al, J. Biol. Chem. 269(2): 1323-1331, 1994.*

Wang et al, Molecular Genetics and Metabolism 105: 203-211, 2012.*

Kramer et al, In Vitro and in Vivo Comparative Study of Chimeric Liver-Specific Promoters, Mol. Therapy 7(3): 375-385, 2003.*

Gehrke et al, Chimeric transcriptional control units for improved liver-specific transgene expression, Gene 322: 137-143, 2003.*

GenBank DC625962 (macaque, 2014).*

GenBank M17030 (mouse OTC, 1993).*

GenBank XP016799394 (chimpanzee OTC, 2018).*

GenBank BX396262, *Homo sapiens* AAT promoter sequence and cDNA, 2010.*

GenBank AL132708.3, *Homo sapiens* chromosome 14 BAC R-34911, 2015.*

GenBank BC114496.1, *Homo sapiens* ornithine carbamoyltransferase, 2006.*

Cunningham et al., AAV2/8-mediated Correction of OTC Deficiency Is Robust in Adult but Not Neonatal Spf$^{ash}$ Mice, Molecular Therapy, vol. 17, No. 8, pp. 1340-1346, 2009.

Wang et al., Sustained Correction Of OTC Deficiency In Spf$^{ash}$ Mice Using Optimized Self Complementary AAV2/8 Vectors, Gene Therapy, vol. 19, pp. 404-410, 2012.

Wang et al., Preclinical Evaluation Of A Clinical Candidate AAVS Vector For Ornithine Transcarbamylase (OTC) Deficiency Reveals Functional Enzyme From Each Persisting Vector Genome, Molecular Genetics And Metabolism, vol. 105, pp. 203-211, 2012.

International Search Report & Written Opinion, dated Feb. 21, 2018, in International Patent Application No. PCT/AU2018/050011.

Luksan, O., et al., Disruption of OTC Promoter-enhancer Interaction in a Patient with Symptoms of Ornithine Carbamoyltransferase Deficiency, Human Mutation, Mutation in Brief 31: E1294-E1303, 2010.

Luksan, O., et al., HNF-4alpha Regulates Expression of Human Ornithin Carbamoyltransferase through Interaction with Two Positive Cis-Acting Regulatory Elements Located in the Proximal Promoter, Folia Biologica (Praha), vol. 60, pp. 133-143, 2014.

PGL3 Luciferase Reporter Vectors, Technical Manual, Promega, 2015.

Search Information Sheet, dated Feb. 21, 2018, in International Patent Application No. PCT/AU2018/050011.

Morizono et al., Expression, purification and kinetic characterization of wild-type human ornithine transcarbamylase and a recurrent mutant that produces 'late onset' hyperammonaemia, Biochem J., vol. 322, pp. 625-631, 1997.

Ye et al., Prolonged Metabolic Correction in Adult Ornithine Transcarbamylase-deficient Mice with Adenoviral Vectors, J Biol Chem, vol. 271, No. 7, pp. 3639-3646, 1996.

* cited by examiner pAAV2-hOTCE.hAATp(2232).SV40int.huOTCco.BGHpA pAAV2-hOTCE.hOTCp(2232).SV40int.huOTCco.BGHpA

POLYNUCLEOTIDES AND VECTORS FOR THE EXPRESSION OF TRANSGENES

PRIORITY AND CROSS REFERENCE TO RELATED APPLICATIONS

This application is the U.S. National Phase Application under 35 U.S.C. § 371 of International Application No. PCT/AU2018/050011, filed Jan. 10, 2018, designating the U.S. and published in English as WO 2018/129586 A1 on Jul. 19, 2018, which claims the benefit of Australian Application No. AU 2017900050, filed Jan. 10, 2017. Any and all applications for which a foreign or a domestic priority is claimed is/are identified in the Application Data Sheet filed herewith and is/are hereby incorporated by reference in their entireties under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled DAVI543002APCSEQLIST.txt, created and last saved on Jul. 9, 2019, which is 123,267 bytes in size. The information in the Electronic Sequence Listing is incorporated herein by reference in its entirety.

FIELD

This application claims priority to Australian Provisional Application No. 2017900050, filed 10 Jan. 2017, the content of which is incorporated herein in its entirety. The present invention is directed to polynucleotides and vectors for the expression of a transgene in liver cells. The present invention is also directed to various uses of the polynucleotides and vectors, such as in gene therapy, and methods for expressing the transgene from the polynucleotides and vectors in liver cells.

BACKGROUND

The expression of transgenes is widely used across many fields and industries, in particular the medical and biotechnology industries. In medical applications, for example, the transgene is generally introduced into target cells of a subject for expression in those cells, typically in order to treat a disease or condition. This is referred to as gene therapy.

Gene therapy has been used both experimentally and in the clinic to treat a range of conditions and diseases, including liver disease, heart disease, diabetes, cancer, immunodeficiencies, arthritis, cystic fibrosis, hemophilia, muscular dystrophy, sickle cell anemia, retinal degenerative conditions, and infectious diseases. Gene therapy can be performed using viral vectors or using non-viral methods, such as transfection of naked DNA or formulation in microparticles and nanoparticles (e.g. liposomes) to transfer the transgene into the target cell.

To facilitate expression of the transgene in the host cell, the transgene is typically contained in a construct that also contains various regulatory elements necessary to express the transgene. These elements can include, for example, promoters, enhancers, initiation signals, termination signals, introns and other regulatory elements, which must function together to facilitate not only stable expression of the transgene in the target cell, but also expression at levels that are sufficient to effect therapy. The promoter and other regulatory elements, as well as the vector or delivery characteristics, determine cell type specificity, transduction efficacy, and level and duration of expression. Stable and robust expression of a transgene in a target cell can be difficult to achieve. There is therefore a continued need for alternative polynucleotides and vectors that facilitate stable and robust expression of a transgene in a host cell.

SUMMARY OF THE DISCLOSURE

The present disclosure is directed to polynucleotides and vectors comprising the polynucleotides that are useful for the expression of transgenes in liver cells.

In one aspect, provided is a polynucleotide comprising, from 5' to 3', a human ornithine transcarbamylase (hOTC) enhancer, a liver-specific promoter and a transgene, wherein the hOTC enhancer is operably linked to the liver-specific promoter and the liver-specific promoter is operably linked to the transgene. The polynucleotide may also comprise an intron between the liver-specific promoter and the transgene, such as, for example, a SV40 intron or a beta-globin intron. The polynucleotide may further comprise a polyadenylation signal sequence 3' of the transgene, such as a BGH-poly(A) signal. In some examples, the polynucleotide comprises a Kozac sequence between the liver-specific promoter and the transgene. Thus, in one embodiment, the polynucleotide comprises, from 5' to 3', a hOTC enhancer, a liver-specific promoter, an intron, a Kozac sequence, a transgene, and a polyadenylation signal.

In some examples, the polynucleotide comprises two or more hOTC enhancers operably linked to the liver-specific promoter. The hOTC enhancer may comprise, for example, a sequence of nucleotides set forth in SEQ ID NO:5, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

In particular embodiments, the liver-specific promoter is a hOTC promoter (e.g. an hOTC promoter comprising a sequence of nucleotides set forth in SEQ ID NO:1 or 2 or a sequence having at least or about 81%, 82%, 83%, 84%, 85%, 86%, 87%, 88%, 89%, 90%, 91%, 92%, 93%, 94%, 95%, 96%, 97%, 98% or 99% sequence identity thereto, or a functional fragment thereof), or a human alpha 1-antitrypsin (hAAT) promoter (e.g. an hAAT promoter comprising a sequence of nucleotides set forth in SEQ ID NO:3 or 4, or a sequence having at least or about 81%, 82%, 83%, 84%, 85%, 86%, 87%, 88%, 89%, 90%, 91%, 92%, 93%, 94%, 95%, 96%, 97%, 98% or 99% sequence identity thereto, or a functional fragment thereof).

In one example therefore, provided is a polynucleotide comprising, from 5' to 3', a hOTC enhancer, a hOTC promoter, a SV40 intron, a Kozac sequence, a transgene, and a BGH-poly(A) signal; a polynucleotide comprising, from 5' to 3', two copies of a hOTC enhancer, a hOTC promoter, a SV40 intron, a Kozac sequence, a transgene, and a BGH-poly(A) signal; and a polynucleotide comprising, from 5' to 3', two copies of a hOTC enhancer, a hOTC promoter, a beta-globulin intron, a Kozac sequence, a transgene, and a BGH-poly(A) signal.

In another example, provided is a polynucleotide comprising, from 5' to 3', a hOTC enhancer, a hAAT promoter, a SV40 intron, a Kozac sequence, a transgene, and a BGH-poly(A) signal; a polynucleotide comprising, from 5' to 3', two copies of a hOTC enhancer, a hAAT promoter, a SV40 intron, a Kozac sequence, a transgene, and a BGH-poly(A) signal; and a polynucleotide comprising, from 5' to 3', two copies of a hOTC enhancer, a hAAT promoter, a beta-globulin intron, a Kozac sequence, a transgene, and a BGH-poly(A) signal.

The transgene in the polynucleotides of the present invention may be a therapeutic transgene, and may encode, for example, a peptide or polypeptide. In particular embodiments, the transgene encodes a polypeptide selected from among ornithine transcarbamoylase (OTC), α1-antitrypsin, factor VIII, factor IX, factor VII, factor X, von Willebrand factor, erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C—X—C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), afamin (AFM), α-galactosidase A, α-L-iduronidase, ATP7b, phenylalanine hydroxylase, lipoprotein lipase, apoliproteins, low-density lipoprotein receptor (LDL-R), albumin, glucose-6-phosphatase and an antibody.

In a specific embodiment, the transgene encodes a human OTC (hOTC) polypeptide, such as one that comprises an amino acid sequence set forth in SEQ ID NO:6 or in amino acids 33-354 of SEQ ID NO:6, or a sequence having at least or about 95%, 96%, 97%, 98%, or 99% sequence identity thereto. In one example, the transgene comprises a sequence of nucleotides set forth in SEQ ID NOs:7 or 8, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

In particular embodiments, provided are polynucleotides comprising a sequence set forth in any one of SEQ ID NOs:15, 17, 19, 21, 23 or 25 or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

The polynucleotides of the present disclosure may further comprise an adeno-associated virus (AAV) inverted terminal repeat (ITR) 5' of the hOTC enhancer and an AAV ITR 3' of the transgene. In some embodiments, the AAV ITRs are derived from an AAV serotype selected from among AAV1, AAV2, AAV3, AAV4, AAV5, AAV6, AAV7, AAV8, AAV9, AAV10, AAV11, AAV12 and AAV13. In a particular example, the AAV ITRs comprise a sequence set forth in SEQ ID NO:13 or 14. Thus, in one embodiment, provides are polynucleotides comprising a sequence set forth in any one of SEQ ID NOs:16, 18, 20, 22, 24 or 25 or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

Also provided are vectors comprising a polynucleotide described above and herein. The vector may be, for example, a polynucleotide vector (e.g. a plasmid, cosmid or transposon, e.g. one comprising a sequence set forth in any one of SEQ ID NOs:27-32) or a viral vector (e.g. an AAV, lentiviral, retroviral, adenoviral, herpesviral or hepatitis viral vector).

Further aspects of the invention include a host cell, comprising a polynucleotide or vector described above and herein.

In another aspect, provided is a method for the expression of a transgene, comprising introducing a polynucleotide or vector described above and herein into a host cell to facilitate expression of the transgene present in the polynucleotide or vector in the host cell.

In a further aspect, provided is a method for the treatment of OTC deficiency in a subject, comprising administering to the subject a polynucleotide or a vector described above and herein that contains an OTC transgene. Also provided is a method for the treatment or prevention of hyperammonemia in a subject with OTC deficiency, comprising administering to the subject a polynucleotide or a vector described above and herein that contains an OTC transgene.

Further aspects of the present invention include the use of a polynucleotide or a vector described above and herein that contains an OTC transgene for the manufacture of a medicament for the treatment of OTC deficiency in a subject, and/or for the treatment or prevention of hyperammonemia in a subject with OTC deficiency.

BRIEF DESCRIPTION OF THE DRAWINGS

Embodiments of the disclosure are described herein, by way of non-limiting example only, with reference to the following drawings.

DETAILED DESCRIPTION

Figure 1:
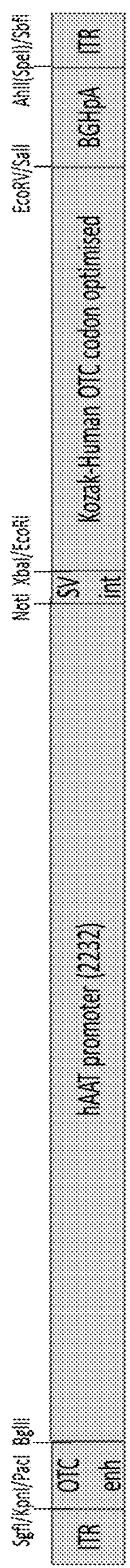
FIG. 1 is a schematic showing the expression constructs in pAAV2-hOTCE.hAATp(2232).SV40int.huOTCco.BGHpA, pAAV2 hOTCE.huOTCp(2232).SV40int.huOTCco.BGHpA, and pAAV2-ApoE.hAATp(251).SV40int.huOTCco.WPRE.
Figure 1:
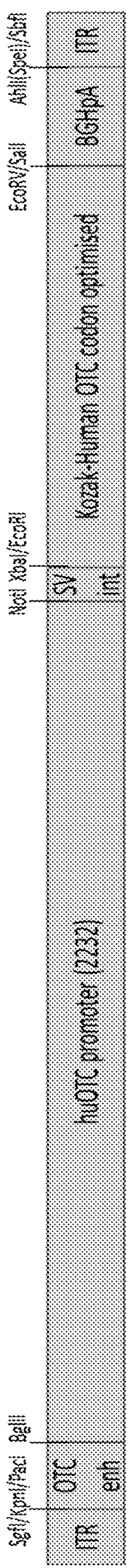

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

As used herein, the singular forms "a", "an" and "the" also include plural aspects (i.e. at least one or more than one) unless the context clearly dictates otherwise. Thus, for example, reference to "a polypeptide" includes a single polypeptide, as well as two or more polypeptides.

In the context of this specification, the term "about," is understood to refer to a range of numbers that a person of skill in the art would consider equivalent to the recited value in the context of achieving the same function or result.

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "promoter" is used herein in its ordinary sense to refer to a nucleotide region comprising a sequence capable of initiating transcription of a downstream (3'-direction) transgene.

A "transgene" as used herein refers to exogenous DNA or cDNA present in a polynucleotide, vector, or host cell that encodes a gene product, such as a peptide or polypeptide, or a polynucleotide that itself has a function or activity, such as an antisense or inhibitory oligonucleotide, including antisense DNA and RNA (e.g. miRNA, siRNA, and shRNA). The transgene may be foreign to the host cell into which it is introduced, or may represent a gene whose expression is otherwise absent or reduced in the host cell in the absence of the introduction of the transgene.

An "enhancer" is used herein in its ordinary sense to refer to a nucleotide region comprising a sequence capable of increasing the level of transcription of a transgene from a promoter as compared to expression of the transgene from the promoter when the enhancer is not present.

As used herein, the term "operably-linked" or "operable-linkage" refers to a functional linkage between two elements, regardless of orientation or distance between the two elements, such that the function of one element is controlled or affected by the other element. For example, operable linkage with reference to a promoter and transgene means that the transcription of the transgene is under the control of, or driven by, the promoter. In another example, operable linkage with reference to an enhancer and promoter means that the enhancer increases the level of transcription of a transgene as driven by a promoter.

As used herein, an "expression construct" or "expression cassette" refers to a polynucleotide or region in a polynucleotide that comprises a transgene operably linked to the necessary elements for expression of the transgene when the cassette or construct is introduced into a suitable host cell. Typically, the cassette or construct will comprise at least the transgene operably linked to a promoter.

As used herein, "corresponding nucleotides" refer to nucleotides that occur at aligned loci. The sequences of related or variant polynucleotides are aligned by any method known to those of skill in the art. Such methods typically maximize matches (e.g. identical nucleotides at positions), and include methods such as using manual alignments and by using the numerous alignment programs available (for example, BLASTN, ClustlW, ClustlW2, EMBOSS, LALIGN, Kalign, etc) and others known to those of skill in the art. By aligning the sequences of polynucleotides, one skilled in the art can identify corresponding nucleotides.

As used herein, a "vector" includes reference to both polynucleotide vectors and viral vectors, each of which are capable of delivering a transgene contained within the vector into a host cell. Vectors can be episomal, i.e., do not integrate into the genome of a host cell, or can integrate into the host cell genome. The vectors may also be replication competent or replication-deficient. Exemplary polynucleotide vectors include, but are not limited to, plasmids, cosmids and transposons. Exemplary viral vectors include, for example, AAV, lentiviral, retroviral, adenoviral, herpesviral and hepatitis viral vectors.

As used herein, "adeno-associated viral vector" or AAV vector refers to a vector derived from an adeno-associated virus, including without limitation, AAV1, AAV2, AAV3, AAV4, AAV5, AAV6, AAV7, AAV8, AAV9, AAV10, AAV11, AAV12 or AAV13, or using synthetic or modified AAV capsid proteins. An AAV vector may also be referred to herein as "recombinant AAV", "rAAV", "recombinant AAV virion", and "rAAV virion," terms which are used interchangeably and refer to a replication-defective virus that includes an AAV capsid shell encapsidating an AAV genome. The AAV genome (also referred to as vector genome, recombinant AAV genome or rAAV genome) comprises a transgene flanked on both sides by functional AAV ITRs. Typically, one or more of the wild-type AAV genes have been deleted from the genome in whole or part, preferably the rep and/or cap genes. Functional ITR sequences are necessary for the rescue, replication and packaging of the vector genome into the rAAV virion.

The term "ITR" refers to an inverted terminal repeat at either end of the AAV genome. This sequence can form hairpin structures and is involved in AAV DNA replication and rescue, or excision, from prokaryotic plasmids. ITRs for use in the present invention need not be the wild-type nucleotide sequences, and may be altered, e.g., by the insertion, deletion or substitution of nucleotides, as long as the sequences provide for functional rescue, replication and packaging. Furthermore, the ITRs may be of any serotype or may be synthetic, and may be the same or different.

The term "host cell" refers to a cell, such as a mammalian cell, that has introduced into it exogenous DNA, such as a vector. The term includes the progeny of the original cell into which the exogenous DNA has been introduced. Thus, a "host cell" as used herein generally refers to a cell that has been transfected or transduced with exogenous DNA.

As used herein, "isolated" with reference to a polynucleotide means that the polynucleotide is substantially free of cellular material or other contaminating proteins from the cells from which the polynucleotide is derived, or substantially free from chemical precursors or other chemicals when chemically synthesized.

It will be appreciated that the above described terms and associated definitions are used for the purpose of explanation only and are not intended to be limiting.

TABLE 1

Brief Description of the Sequences

| SEQ ID NO: | Description |
|---|---|
| 1 | Human ornithine transcarbamylase (hOTC) promoter (2232 bp) |
| 2 | Truncated hOTC promoter (789 bp) |
| 3 | Human alpha 1-antitrypsin (hAAT) promoter (2232 bp) |
| 4 | Truncated hAAT promoter (392 bp) |
| 5 | hOTC enhancer (175 bp) |
| 6 | Wild-type OTC polypeptide |
| 7 | Wild-type hOTC polypeptide |
| 8 | Codon-optimized hOTC transgene |
| 9 | bovine growth hormone (BGH) poly(A) |
| 10 | Kozac sequence |
| 11 | SV40 intron |
| 12 | beta-globulin intron |
| 13 | 5' AAV ITR |
| 14 | 3' AAV ITR |
| 15 | hOTCE.hOTCp.SV40int.hOTCco.BGHpa expression cassette |
| 16 | AAV2-hHOTCE.hOTCp.SV40int.hOTCco.BGHpa expression cassette (incl. ITRs) |
| 17 | hOTCE.hAATp.SV40int.hOTCco.BGHpa expression cassette |
| 18 | AAV2-hOTCE.hAATp.SV40int.hOTCco.BGHpa expression cassette (incl. ITRs) |
| 19 | 2hOTCE.hOTCp.SV40int.hOTCco.BGHpa expression cassette |
| 20 | AAV2-hOTCE.hOTCp.SV40int.hOTCco.BGHpa expression cassette (incl. ITRs) |
| 21 | 2hOTCE.hOTCp.βgint.hOTCco.BGHpa expression cassette |
| 22 | AAV2-2hOTCE.hOTCp.βgint.hOTCco.BGHpa expression cassette (incl. ITRs) |
| 23 | 2hOTCE.hAATp.SV40int.hOTCco.BGHpa expression cassette |
| 24 | AAV2-2hOTCE.hAATp.SV40int.hOTCco.BGHpa expression cassette (incl. ITRs) |
| 25 | 2hOTCE.hAATp.βgint.hOTCco.BGHpa expression cassette |
| 26 | AAV2-2hOTCE.hAATp.βgint.hOTCco.BGHpa expression cassette (incl. ITRs) |
| 27 | pAAV2-hOTCE.hOTCp.SV40int.hOTCco.BGHpa |
| 28 | pAAV2-hOTCE.hAATp.SV40int.hOTCco.BGHpa |
| 29 | pAAV2-2hOTCE.hOTCp.SV40int.hOTCco.BGHpa |
| 30 | pAAV2-2hOTCE.hOTCp.βgint.hOTCco.BGHpa |
| 31 | pAAV2-2hOTCE.hAATp.SV40int.hOTCco.BGHpa |
| 32 | pAAV2-2hOTCE.hAATp.βgint.hOTCco.BGHpa |
| 33 | OTC forward primer |
| 34 | OTC reverse primer |
| 35 | GAPDH forward primer |
| 36 | GAPDH reverse primer |

Polynucleotides

Provided are polynucleotides that comprise expression constructs and that can be used for the expression of a transgene, such as for gene therapy. The polynucleotides therefore include a promoter operably linked to a transgene. The polynucleotides further include an enhancer operably linked to the promoter. Other elements that may be present in the polynucleotides include, but are not limited to, an intron between the promoter the transgene, a transcriptional termination signal downstream of the transgene, such as a polyadenylation signal sequence, and other posttranscriptional elements, such as a posttranscriptional regulatory element and/or a translation initiation enhancer, such as a Kozac sequence. In particular embodiments, the polynucleotide also comprises viral elements to facilitate packaging of the polynucleotide into a viral vector. For example, some polynucleotides of the present disclosure contain AAV inverted terminal repeat regions (ITRs) flanking the transgene and associated regulatory elements to facilitate packaging of the polynucleotide in an AAV vector.

The various polynucleotides described herein, including those comprising, for example, promoter sequences, enhancer sequences, transgene sequences, other regulatory elements, and/or AAV ITRs, may be natural, recombinant or synthetic and may be obtained by purification from a suitable source or produced by standard synthetic or recombinant DNA techniques such as those well known to persons skilled in the art, and described in, for example, Sambrook et al., Molecular Cloning: a Laboratory Manual, Cold Spring Harbor Laboratory Press.

As described herein, the selection or design of the various elements in the polynucleotides, and the particular combination of the elements, is dictated at least in part by the requirements associated with the system used for delivery and/or expression of the operably linked transgene. For example, where a viral vector is used, the polynucleotides will contain the requisite viral elements to facilitate packaging, etc. Furthermore, viral vectors have limitations on the size of the genome that can be packaged, which in turn can dictate the size of each element in the genome. For example, AAV can package a genome slightly larger than the size of a wild-type genome, which is approximately 4.7 kb. Optimal packaging is achieved with genomes having a size of about 4.1-4.9 kb and packaging efficiencies can be adversely affected with genomes smaller or larger than this. For example, packaging may be significantly reduced when very large genomes are packaged. Packaging and transduction efficiency may also be adversely affected when smaller genomes are used. Without being bound by theory, there is the potential for additional DNA to be packaged in these circumstances, which in turn can result in errors in virus titration and dosage, and/or transductions efficiency. Thus, in particular embodiments of the present invention where the polynucleotides are designed for use in AAV vectors and thus represent the AAV genome (i.e. contain 5' and 3' AAV ITRs flanking the transgene and regulatory elements), the size of the polynucleotide is about or at least 85%, 86%, 87%, 88%, 89%, 90%, 91%, 92%, 93%, 94%, 95%, 96%, 97%, 98%, 99% or 100% of the size of a wild-type AAV genome.

Promoters

The polynucleotides of the present invention comprise a liver-specific promoter that is operably linked to a transgene and is capable of driving the expression of the transgene in liver cells. Typically, the liver cells are human liver cells. Exemplary liver-specific promoters that can be utilized in the context of the polynucleotides of the invention include the ornithine transcarbamylase (OTC) promoter and the alpha 1-antitrypsin (AAT) promoter. Other liver-specific promoters include, but are not limited to, the albumin promoter, hepatitis B virus core promoter, thyroxin binding globulin (TGB) promoter and the LSP1 promoter (Cunningham et al. (2008) Molecular Therapy 16:1081-1088).

In particular embodiments, the promoter is a human OTC (hOTC) promoter. The hOTC promoter can comprise the 2232 nucleotide sequence set forth in SEQ ID NO:1, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto. In some examples, the hOTC promoter is a functional fragment (i.e. a fragment that has the ability to drive transcription of an operably linked transgene) of the sequence set forth in SEQ ID NO:1 or a sequence having at least or about 81% sequence identity thereto. Exemplary functional fragments include those comprising at least or about 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050 or 2100 nucleotides of the set forth in SEQ ID NO:1 or of a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1.

Functional fragments of SEQ ID NO:1 are known in the art (see e.g. Luksan et al. (2010) Human Mutation 31: E1294-E1303) and can be readily identified by those skilled in the art using routine methods. Typically, the functional fragment will include the 3' portion of the promoter set forth in SEQ ID NO:1, which includes the transcriptional start site(s) and TATA-boxes. As described in Luksan et al., there are potential TATA boxes at nucleotides 1993-1997, 2079-2083 and 2136-2140 of SEQ ID NO:1, and potential transcription start sites at nucleotides 2109, 2183 and 2159 of SEQ ID NO:1. Thus, in some examples, the hOTC promoter comprises at least or about 300, 350, 400, 450, 500, 550, 600, 650, 700, 750 or 800 nucleotides from the 3' end of the sequence set forth in SEQ ID NO:1 or of a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1, such as at least or about nucleotides 1933-2232, 1833-2232, 1733-2232, 1633-2232, 1533-2232, or 1433-2232 of the sequence set forth in SEQ ID NO:1 or corresponding nucleotides in a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 1. In a particular example, the hOTC promoter comprises the 789 nucleotide sequence set forth in SEQ ID NO:2 and fragments with a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO:2.

In other embodiments, the promoter is the hAAT promoter. An exemplary hAAT comprises the sequence of nucleotides set forth in SEQ ID NO:3, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto. In other examples, the hAAT promoter is a functional fragment (i.e. a fragment that has the ability to drive transcription of an operably linked transgene) of the sequence set forth in SEQ ID NO:3 or a sequence having at least or about 81% sequence identity thereto. Exemplary fragments include those comprising at least or about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050 or 2100 nucleotides of the sequence set forth in SEQ ID NO:3 or of a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3. Thus, in some examples, the hAAT promoter comprises at least or about 200, 250, 300, 350, 400, 450, 500, 550, 600, 650, 700, 750 or 800 nucleotides from the 3' end of the sequence set forth in SEQ ID NO:3 or a sequence having at least or about 81% sequence identity thereto, such as nucleotides 2033-2232, 1933-2232, 1833-2232, 1733-2232, 1633-2232, 1533-2232, or 1433-2232 of the sequence set forth in SEQ ID NO:3 or corresponding nucleotides in a sequence having at least or about 81% sequence identity to SEQ ID NO:3. In one example, the hAAT promoter comprises about 400 nucleotides, such as 392 nucleotides, such as the sequence set forth in SEQ ID NO:4 or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

The size of the promoter can be selected or designed, at least in part, taking into consideration any size limitations, preferences or requirements associated with the system used for delivery and/or expression of the operably linked transgene. For example, as discussed above, viral vectors such as AAV vectors have upper and lower limits on the genome size for efficient packaging and/or transduction. Thus, where the transgene is smaller in length, a larger promoter can be used to ensure that the combined length of the transgene, promoter and other elements is between about 4.1-4.9 kb. Conversely, where the transgene is a large transgene, a smaller promoter can be used.

The importance of selecting and/or designing a promoter of the optimal size for the particular expression construct is demonstrated in Example 3, below. In the exemplified AAV constructs for OTC expression, the hAAT and hOTC promoters were extended 5' so that they were larger than promoters that are typically used in AAV constructs. The use of these relatively large promoters produced an optimal construct for packaging and expression of the OTC transgene, which is relatively small. The overall construct (including ITRs) had a similar size to wild-type AAV (about 90% of the wild-type genome size), with good packaging and transduction efficiencies. In contrast, comparable constructs with more typically-sized (i.e. smaller) promoters had significantly lower transduction efficiencies. Thus, in particular embodiments where the transgene is an OTC gene, the promoter in the polynucleotide of the present invention is about 2230 bp in length, such as about 2180, 2190, 2200, 2210, 2220, 2230, 2240, 2250, 2260, 2270 or 2280 bp in length. In specific embodiments, the promoter is from 2180 to 2280 bp in length, or from 2190 to 2270 bp, 2200-2260 bp, 2210 to 2250 bp, or 2220-2240 bp in length. In a particular embodiment, the promoter is 2232 bp in length (e.g. the hOTC promoter set forth in SEQ ID NO:1 or the hAAT promoter set forth in SEQ ID NO:3).

Enhancers

The polynucleotides of the present invention further comprise an enhancer that is operably linked to the promoter, such that it increases the level of transcription of a transgene from a promoter. The enhancer need not be in any specified position in the polynucleotide in relation to the promoter, transcriptional start site, transcriptional termination site or transgene, provided it is operably linked to the promoter so as to enhance transcription of the transgene from the promoter. Thus, the enhancer may be upstream of the promoter (i.e. 5' of the promoter) or downstream of the promoter (i.e. 3' of the promoter), or upstream or downstream of the transgene, and may be directly adjacent to the promoter or transgene or separated by an intervening sequence. Furthermore, the polynucleotides can comprise 1, 2, 3 or more enhancers, which may be the same or different. In some embodiments, the polynucleotide comprises only one enhancer so as to reduce the potential for enhancement of off-target, endogenous genes (e.g. oncogenes) in the host cell into which the polynucleotide is introduced.

Exemplary polynucleotides of the present disclosure comprise a hOTC enhancer. The hOTC enhancer can comprise a sequence of nucleotides set forth in SEQ ID NO:5, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto. Typically, when the transgene is an OTC gene, the hOTC enhancer is about 150, 155, 160, 165, 170, 175, 180, 185, 190, 195, or 200 bp in length. In some embodiments, the hOTC enhancer is from 150-200, 155-195, 160-190, 165-185 or 170-180 bp in length. In a specific embodiment, the hOTC enhancer is 175 bp in length.

Transgenes

The polynucleotides of the present disclosure comprise a transgene operably linked to the promoter. The promoter and transgene can be immediately adjacent one another or can be separated by an intervening stretch of nucleotides, such as an intervening stretch of 5, 10, 20, 30, 40, 50 or more nucleotides. In particular examples, the promoter and transgene are separated by an intron, such as one described herein. The transgene can encode a peptide or polypeptide, or can encode a polynucleotide or transcript that itself has a function or activity, such as an antisense or inhibitory oligonucleotide, including antisense DNA and RNA (e.g. miRNA, siRNA, and shRNA).

In particular embodiments, the polynucleotide of the invention can be used in gene therapy, wherein the expression of the transgene provides therapy for a disease or condition, i.e. the transgene is a therapeutic transgene that encodes a therapeutic peptide, therapeutic polypeptide or therapeutic polynucleotide. Therapeutic transgenes therefore do not encompass reporter genes (i.e. genes that encode detectable markers), such as genes that encode enzymes that convert a substrate to a luminescent or coloured product (e.g. luciferase, (3-galactosidase etc) and genes that encode fluorescent markers (e.g. green fluorescent protein, red fluorescent protein etc). Expression of a therapeutic peptide or polypeptide may serve to restore or replace the function of the endogenous form of the peptide or polypeptide that is defective (i.e. gene replacement therapy). In other examples, expression of a therapeutic peptide or polypeptide, or polynucleotide, from the transgene serves to alter the levels and/or activity of one or more other peptides, polypeptides or polynucleotides in the host cell. Thus, according to particular embodiments, the expression of a transgene contained within a polynucleotide described herein in a host cell can be used to provide a therapeutic amount of a peptide, polypeptide or polynucleotide to ameliorate the symptoms of a disease or disorder. For the purposes of the present invention, expression is in a liver cell and treatment is for a disease or disorder associated with the liver, including diseases or disorders that affect liver cells, and diseases or disorders that are associated with a polypeptide or polynucleotide expressed in liver cells. In some instances, the product of the transgene may also be secreted into the bloodstream after expression.

In some examples, the therapeutic peptide, polypeptide, or polynucleotide encoded by the therapeutic transgene is involved in or affects cell metabolism, the immune response, hematopoiesis, inflammation, cell growth and proliferation, cell lineage differentiation, and/or the stress response. Non-limiting examples of therapeutic polypeptides include ornithine transcarbamoylase (OTC), α1-antitrypsin, factor VIII, factor IX, factor VII, factor X, von Willebrand factor, erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C—X—C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), afamin (AFM), α-galactosidase A, α-L-iduronidase, ATP7b, phenylalanine hydroxylase, lipoprotein lipase, apoliproteins, low-density lipoprotein receptor (LDL-R), albumin, glucose-6-phosphatase, antibodies, nanobodies, anti-viral dominant-negative proteins, and fragments, subunits or mutants thereof.

In one example, the transgene is a human OTC (hOTC) transgene that encodes the wild-type hOTC polypeptide set forth in SEQ ID NO:6 or the mature form thereof (i.e. amino acids 33-354 of SEQ ID NO:6), or a variant polypeptide comprising at least or about 95%, 96%, 97%, 98%, or 99% sequence identity thereto, wherein the variant polypeptide retains activity of the wild-type hOTC polypeptide. Typically, the variant polypeptide will retain at least or about 50%, 55%, 60%, 65%, 70%, 75%, 80%, 85%, 90% or 95% of the activity of the wild-type OTC. OTC activity can be assessed using any method known in the art, such as using the assay described below in Example 2 or those previously described by Ye et al. (J Biol Chem (1996) 271:3639-3646) and Morizono et al. (Biochem J. (1997) 322:625-631).

Exemplary hOTC transgenes therefore include the wild-type human transgene set forth in SEQ ID NO:7 and variants thereof, including codon-optimised variants thereof. In a particular embodiment the hOTC transgene is codon-optimised and comprises a sequence of nucleotides set forth in SEQ ID NO:8, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the encoded OTC polypeptide retains at least or about 50%, 55%, 60%, 65%, 70%, 75%, 80%, 85%, 90% or 95% of the activity of the wild-type OTC. In other embodiments, the hOTC transgene is a codon-optimized sequence described in WO 2015/138348.

Other Elements

The polynucleotides of the present invention can comprise additional elements to help facilitate stable and strong expression of a transgene from a promoter in a host cell. These additional elements include, but are not limited to, transcriptional and translational termination signals, translational initiation enhancers, posttranscriptional regulatory elements, introns and other elements.

Examples of transcriptional termination signals include, but are not limited to, polyadenylation signal sequences, such as bovine growth hormone (BGH) poly(A), SV40 late poly(A), rabbit beta-globin (RBG) poly(A), thymidine kinase (TK) poly(A) sequences, and any variants thereof. In some embodiments, the polynucleotides of the present disclosure contain a BGH-poly(A) signal, such as one comprising a sequence of nucleotides set forth in SEQ ID NO:9, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto. The polynucleotides may also comprise a translational initiation enhancer, such as a Kozac sequence (such as one set forth in SEQ ID NO:10), between the promoter and transgene.

The polynucleotides can include various posttranscriptional regulatory elements that can function to increase the expression level of a transgene. In some embodiments, the posttranscriptional regulatory element is a viral posttranscriptional regulatory element, such as the hepatitis B virus posttranscriptional regulatory element (HBVPRE), RNA transport element (RTE), and any variants thereof. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

The polynucleotides of the present invention may also include one or more introns, which can serve to enhance mRNA processing and expression of the transgene in the polynucleotide. Typically, the intron is between the promoter and the transgene. Exemplary introns include, but are not limited to, a SV40 intron (such as the SV40 intron set forth in SEQ ID NO: 11), a beta-globin intron (such as the beta-globin intron set forth in SEQ ID NO:12), the minute virus of mice (MVM) intron and the truncated FIX intron 1. The introns may be selected and/or designed to have a particular size, such that when combined in the polynucleotide with other elements and transgene, the resulting construct is optimally sized for viral packaging and transduction. For example, where the transgene is an OTC gene and the polynucleotides are for use in AAV vectors, the size of the intron (e.g. an SV40 intron) may be about 70, 75, 80, 85, 90, 95 or 100 bp. In particular embodiments, the intron is from 70-100, 75-95 or 80-90 bp. In a particular example, the intron is 87 bp in length.

The polynucleotides may also comprise a signal peptide sequence to provide for secretion of a polypeptide encoded by a transgene from a mammalian cell. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. Typically, the nucleotide sequence of the signal peptide is located immediately upstream of the transgene (e.g., fused at the 5' of the coding region of the protein of interest) in the vector.

The polynucleotides may also contain further regulatory sequences, such as one that facilitates translation of multiple proteins from a single mRNA. Non-limiting examples of such regulatory sequences include internal ribosome entry site (IRES) and 2A self-processing sequence, such as a 2A peptide site from foot-and-mouth disease virus (F2A sequence).

In some embodiments, the polynucleotides of the present invention further comprise functional AAV inverted terminal repeats (ITRs) flanking the transgene and regulatory elements (i.e. the polynucleotides comprise a 5' AAV ITR and a 3' AAV ITR flanking the transgene and regulatory elements), so as to facilitate packaging of the transgene and regulatory elements into an AAV vector. AAV ITRs may be derived from any of several AAV serotypes, including without limitation, AAV1, AAV2, AAV3, AAV4, AAV5, AAV6, AAV7, AAV8, AAV9, AAV10, AAV11, AAV12, AAV13, etc., or may be synthetic. AAV ITRs are typically about 145 nucleotides in length, although need not have a wild-type nucleotide sequence, i.e. may be altered by the insertion, deletion and/or substitution of nucleotides, provided they are functional. Furthermore, the ITRs in the polynucleotide need not necessarily be the same or derived from the same AAV serotype or isolate, so long as they function as intended, i.e., assist in the rescue, replication and packaging a transgene. The nucleotide sequences of AAV ITRs are well known in the art. Exemplary AAV ITRs useful for the polynucleotides of the present disclosure include, for example, those set forth in SEQ ID NOs:13 and 14.

Exemplary Polynucleotides

Polynucleotides of the present disclosure include those comprising a hOTC enhancer and a human liver-specific promoter, operably linked to a transgene. The enhancer may be upstream or downstream of the promoter or upstream or downstream of the transgene. For example, provided are polynucleotides comprising, from 5' to 3', a hOTC enhancer, a human liver-specific promoter and a transgene. Typically, the liver-specific promoter is a hOTC promoter or a hAAT promoter.

Exemplary of the polynucleotides of the present disclosure are those comprising a hOTC enhancer and hOTC promoter operably linked to a transgene. In some embodiments, the hOTC enhancer is upstream of the hOTC promoter, i.e. the polynucleotide contains, from 5' to 3', a hOTC enhancer, a hOTC promoter and a transgene. Alternatively, the hOTC enhancer may be downstream of the promoter, such as downstream of the transgene, i.e. the polynucleotide contains, from 5' to 3', the hOTC promoter, transgene and hOTC enhancer.

Other exemplary polynucleotides of the present disclosure comprise a hOTC enhancer and hAAT promoter operably linked to a transgene. In some embodiments, the hOTC enhancer is upstream of the hAAT promoter, i.e. the polynucleotide contains, from 5' to 3', a hOTC enhancer, a hAAT promoter and a transgene. Alternatively, the hOTC enhancer may be downstream of the promoter, such as downstream of the transgene, i.e. the polynucleotide contains, from 5' to 3', the hAAT promoter, transgene and hOTC enhancer.

Polynucleotides of the present disclosure also include those comprising an ApoE enhancer and a hAAT promoter, operably linked to a transgene, e.g., from 5' to 3', an ApoE enhancer, a hAAT promoter and a transgene.

In some examples, these polynucleotides further comprise a BGH-poly(A) signal 3' of the transgene, and an intron (e.g. a SV40 intron or beta-globulin intron) between the promoter and transgene. The polynucleotides may also include a Kozac sequence between the promoter (or intron) and the transgene.

In particular embodiments, the transgene is a hOTC transgene, such as one comprising the sequence set forth in SEQ ID NO:8, or a sequence having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the hOTC gene is a functional hOTC gene (i.e. encodes a functional hOTC polypeptide). The polynucleotides of the present invention thus include polynucleotides that can be used to express a functional OTC polypeptide from an hOTC transgene (i.e. an OTC polypeptide having at least or about 50%, 60%, 70%, 80% or 90% of the activity of a wild-type OTC polypeptide).

Exemplary polynucleotides include those comprising, from 5' to 3':

- a hOTC enhancer, a hOTC promoter, a SV40 intron, a hOTC transgene and a BGH-poly(A) signal. An exemplary polynucleotide comprises the hOTCE.hOTCp.SV40int.hOTCco.BGHpa expression construct having a sequence set forth in SEQ ID NO:15, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the polynucleotide can be used to express a functional OTC polypeptide from the hOTC transgene.

- a hOTC enhancer, a hAAT promoter, a SV40 intron, a hOTC transgene and a BGH-poly(A) signal. An exemplary polynucleotide comprises the hOTCE.hAATp.SV40int.hOTCco.BGHpa expression construct having a sequence set forth in SEQ ID NO:17, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the polynucleotide can be used to express a functional OTC polypeptide from the hOTC transgene.
- 2 hOTC enhancers, a hOTC promoter, a SV40 intron, a hOTC transgene and a BGH-poly(A) signal. An exemplary polynucleotide comprises the 2hOTCE.hOTCp.SV40int.hOTCco.BGHpa expression construct having a sequence set forth in SEQ ID NO: 19, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the polynucleotide can be used to express a functional OTC polypeptide from the hOTC transgene.
- 2 hOTC enhancers, a hOTC promoter, a beta-globulin intron, a hOTC transgene and a BGH-poly(A) signal. An exemplary polynucleotide comprises the 2hOTCE.hOTCp.βgint.hOTCco.BGHpa expression construct having a sequence set forth in SEQ ID NO:21, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the polynucleotide can be used to express a functional OTC polypeptide from the hOTC transgene.
- 2 hOTC enhancers, a hAAT promoter, a SV40 intron, a hOTC transgene and a BGH-poly(A) signal. An exemplary polynucleotide comprises the 2hOTCE.hAATp.SV40int.hOTCco.BGHpa expression construct having a sequence set forth in SEQ ID NO:23, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the polynucleotide can be used to express a functional OTC polypeptide from the hOTC transgene.
- 2 hOTC enhancers, a hAAT promoter, a beta-globulin intron, a hOTC transgene and a BGH-poly(A) signal. An exemplary polynucleotide comprises the 2hOTCE.hAATp.βgint.hOTCco.BGHpa expression construct having a sequence set forth in SEQ ID NO:25, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto, wherein the polynucleotide can be used to express a functional OTC polypeptide from the hOTC transgene.

In further embodiments, the polynucleotides also contain AAV ITRs flanking the expression constructs, i.e. a 5' AAV ITR that is 5' of the enhancer, and a 3' AAV ITR that is 3' of the BGH-poly(A) signal or the 3' UTR. In particular embodiments (e.g. those embodiments in which the polynucleotide comprises AAV ITRs flanking the hOTCE.hOTCp.SV40int.hOTCco.BGHpa or hOTCE.hAATp.SV40int.hOTCco.BGHpa expression constructs), the resulting polynucleotide has a size that is about or at least 90% of the size of a wild-type AAV genome, resulting in efficient packaging and transduction.

Exemplary polynucleotides comprising AAV ITRs include those comprising the AAV2-hOTCE.hOTCp.SV40int.hOTCco.BGHpa expression construct having a sequence set forth in SEQ ID NO:16, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; the AAV2-hOTCE.hAATp.SV40int.hOTCco.BGHpa expression construct having a sequence set forth in SEQ ID NO:18, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; the AAV2-2hOTCE.hOTCp.SV40int.hOTCco.BGHpa expression construct having a sequence set forth in SEQ ID NO:20, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; the AAV2-2hOTCE.hOTCp.βgint.hOTCco.BGHpa expression construct having a sequence set forth in SEQ ID NO:22, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; the AAV2-2hOTCE.hAATp.SV40int.hOTCco.BGHpa expression construct having a sequence set forth in SEQ ID NO:24, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; or the AAV2-2hOTCE.hAATp.βgint.hOTCco.BGHpa expression construct having a sequence set forth in SEQ ID NO:26, or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

Vectors

The present disclosure also provides vectors comprising the polynucleotides described above and herein. The vectors can be polynucleotide vectors (e.g. plasmids, cosmids or transposons) or viral vectors (e.g. AAV, lentiviral, retroviral, adenoviral, herpesviral, or hepatitis viral vectors).

Vectors suitable for use are widely described and well-known in the art. Those skilled in the art would appreciate that vectors of the present invention that comprise a polynucleotide described herein may also contain additional sequences and elements useful for the replication of the vector in prokaryotic and/or eukaryotic cells, and selection of the vector. For example, the vectors of the present disclosure can include a prokaryotic replicon (that is, a sequence having the ability to direct autonomous replication and maintenance of the vector extrachromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein.

Exemplary polynucleotide vectors include pAAV2-hOTCE.hOTCp.SV40int.hOTCco.BGHpa having a sequence set forth in SEQ ID NO:27 (where the ITR1 is at nt 262-406; the hOTC enhancer is at nt 446-620, the hOTC promoter is at nt 627-2858; the SV40 intron is at nt 2867-2953, the Kozak sequence is at 2973-2979, the hOTC gene is at 2980-4044, the BGHpA is at nt 4057-4317, and the ITR2 is at nt 4367-4511), or a vector having at least or about 81%, 82%, 83%, 84%, 85%, 86%, 87%, 88%, 89%, 90%, 91%, 92%, 93%, 94%, 95%, 96%, 97%, 98%, or 99% sequence identity thereto whereby the vector can be introduced into a cell for expression of the hOTC gene at levels that are at least or about 50%, 60%, 70%, 80%, 90% or more of the expression levels observed when pAAV2-hOTCE.hOTCp.SV40int.hOTCco.BGHpa is introduced into the cell.

SEQ ID NO: 27:

GCTAGCGATGACCCTGCTGATTGGTTCGCTGACCATTTCCGGGTGCGGGACGGCGTTA

CCAGAAACTCAGAAGGTTCGTCCAACCAAACCGACTCTGACGGCAGTTTACGAGAGA

GATGATAGGGTCTGCTTCAGTAAGCCAGATGCTACACAATTAGGCTTGTACATATTGT

CGTTAGAACGCGGCTACAATTAATACATAACCTTATGTATCATACACATACGATTTAG

GTGACACTATAGAATACACGGAATTAATTCTTGGCCACTCCCTCTCTGCGCGCTCGCTC

GCTCACTGAGGCCGCCCGGGCAAAGCCCGGGCGTCGGGCGACCTTTGGTCGCCCGGCC

TCAGTGAGCGAGCGAGCGCGCAGAGAGGGAGTGGCCAACTCCATCACTAGGGGTTCC

TTACGTAGCCATGCTCTAGCGATCGCGGTACCTTAATTAATTAGGGCTGATTGTTGAGA

CACTGGTGAACTTTGAACCTCTGTGATTTCCCTGTTTGCTCTGTGCCTGATAGCTTTCA

GTCTGCTAACAAATCTCCTTTATGCAGTTTAACCTCTGTACTTCCAATGGGGAGGAATT

GGAATCAGCCTATGGGAGAAGAGATAGCTCTAGGATTCAGATCTACAAGAAAGTTAA

AATTGAATTAGAGGAATCATGGGGTCAACAAGAGCCCCTGGATGAATTCTGAGGATG

AACATCAAAGCCTGTAAAGTAAAACAGACTCCACATGTGACATAATCAGCAGAAGCT

GGGTAGTTGAAATCTACCCCTCAACAAGTTCATTGAGATGCCCTGCCTTTTGAGATTCA

GTGAAATTGCTTTTAACTTCATCCCACTTGTGATGCAGCTCCCCTTTTCCAATCCCTCTG

GGAGTTATTGGTATCTTAACTTTTTTTTAGTTCCCTCTGGCTTTGAGCTCCTGCATCTGT

AGCATTAGGAGGGTTTGTGAGTTGCTTTGGCATCTCAGAAATGCTGCCTGTACTCTCTA

GCATGGAACTGCAGACACTTCTTGATTTCTCCCCAAGCATTACCAATATGAGTTGTGTG

TATGGCTAGCACAGTTCAGTGAAGATATGGGGTCAAGCTATGGGCTTTATATTAGCCT

GTGGTTTGGCCTCATCTCCCTCAGGCTCCATGCAAACGTTCAATTTCACTCCTGTATTA

TGTGGAGCGCTTTTGCTCTCTGAAACCTATTCAATAACTGGCCTTGTTTGCCTCTTCAA

AGATGCTTTATTATGTTTTTTAAATTCACTCTCTCCCTTCTCACCTCTGTACCTTTGCAA

GCAGTTGCTTCTGCCTGGAATATCCTTTCCAGAATGGAAGATTTGGTAGAGGTTGGGA

AATGTCAGTCTTTCCCCTCACTTTATCTCACATCATTCTCTGTAAGTAGAAGGAAATGG

TGACAATATTTATTTCTCTACTAGTATTAATTATGACATCACAAACATCTCGGCTCCTG

AGGTGGCCATAGTTGGTCTTTAAATAACACTTTTTGGTATTCCACAAACTTCTGGAAAA

TATTTACTTGGGTTTGCTAAAGTCATATAAATTGACCAGAAGAGGCAGCCCTACCCCT

GCCCCTCCTCTCCTTCCTCCTACCCTTCCTACCTTAGAGGGCTCCCGCTTCTTCGAAGCC

AGACAACTTTGTCTGGACCTCTCCTATGGGCTTGTATTATGGATATTTGTTTATAAATC

ATACCACCTTTACTGAACTGTGAACTCTGCAAAGATGATGTCATCTTCCCTCTCTGAAA

CTTCAGTGCAGCTCGGTATCTGATACAGAATTGACTTTGAATCACCTGATTTCTAACTG

AGGATAAATGAATAAATGTGAAGTTGCAGATGGCCCCTTAGTGATCTGAATAGGCTGC

TAGGGGAAGAGCATATGGTATCCCCACTTCCCACTTGTACTGACTGTCAGGTGCTGTT

AGAATCAATAGGCAACTATTTCTTTTCTTTTTCTTTCTTTCTTTCTTTTTTTTGAGACAGT

GTCTCTCTCTGTCACCCAGGCTGGAGTACAGTGGTGCAATCTGGGCTCACTGCAACCTC

TGTCTCCCGGGTTCAAGCGACTCTCATGCCTCAGCCTCCCAAATAGCTGGGATTACAG

-continued

GTGTGCACCACCACGTCTAGCTAATTTTTGTATTTTTAGTGGAGACGGGGATTCACCAT

GTTGGCCAGGCTGGTCTCGAACTCCTGGGCTCAAGTGATCCGCCCGCCTCAGCCTCCC

AAAGTGCTGGGATTACAGGCGTGAGCCACCGTGCCCGGCCAGCAATTATTTCTTTATT

GAAGACTTATGTGCAAGGCACAAAGGGAGCTCCAGGACTGAGATATTTTTACTATACC

TTCTCTATCATCTTGCACCCCCAAAATAGCTTCCAGGGCACTTCTTTCTATTTGTTTTTG

TGGAAAGACTGGCAATTAGAGGTAGAAAAGTGAAATAAATGGAAATAGTACTACTCA

GGACTGTCACATCTACATCTGTGTTTTTGCAGTGCCAATTTGCATTTTCTGAGTGAGTT

ACTTCTACTCACCTTCACAGCAGCCGGTACCGCAGTGCCTTGCATATATTATATCCTCA

ATGAGTACTTGTCAATTGATTTTGTACATGCGTGTGACAGTATAAATATATTATGAAAA

ATGAGGAGGCCAGGCAATAAAAGAGTCAGGATTTCTTCCAAAAAAAATACACAGCGG

TGGAGCTTGGCATAAAGTTCAAATGCTCCTACACCCTGCCCTGCAGTATCTCTAACCA

GGGGACTTTGATAAGGAAGCTGAAGGGTGATATTACCTTTGCTCCCTCACTGCAACTG

AACACATTTCTTAGTTTTTAGGTGGCCCCCGCTGGCTAACTTGCTGTGGCGGCCGCTCT

AAGGTAAATATAAAATTTTTAAGTGTATAATGTGTTAAACTACTGATTCTAATTGTTTC

TCTCTTTTAGATTCCAACCTTTGGAACTGATCTAGAGAATTCGCCGCCACCATGCTGTT

TAACCTGAGAATCCTGCTGAATAACGCTGCCTTTAGGAACGGACATAACTTCATGGTC

CGCAACTTTCGCTGTGGCCAGCCTCTCCAGAACAAAGTGCAGCTGAAGGGGAGGGAC

CTGCTGACCCTGAAAAATTTCACAGGAGAGGAAATCAAGTACATGCTGTGGCTGTCTG

CCGATCTGAAGTTCCGGATCAAGCAGAAGGGCGAATATCTGCCACTGCTCCAGGGCAA

AAGTCTGGGGATGATCTTCGAAAAGAGGAGTACTCGGACCAGACTGTCAACAGAGAC

TGGATTCGCTCTGCTGGGAGGACACCCATGCTTTCTGACCACACAGGACATTCATCTG

GGCGTGAACGAGTCACTGACCGACACAGCCCGGGTGCTGAGCAGCATGGCCGATGCC

GTGCTGGCACGGGTCTACAAACAGAGCGACCTGGATACCCTGGCTAAGGAAGCAAGC

ATCCCCATCATTAATGGGCTGTCCGACCTGTATCACCCTATCCAGATTCTGGCCGATTA

CCTGACCCTCCAGGAGCATTATTCTAGTCTGAAAGGCCTGACACTGAGCTGGATTGGG

GACGGAAACAATATCCTGCACTCCATTATGATGTCTGCCGCTAAGTTTGGGATGCACC

TCCAGGCAGCCACACCAAAAGGCTACGAACCCGATGCCAGTGTGACTAAGCTGGCCG

AACAGTATGCTAAAGAGAACGGCACTAAGCTGCTGCTGACCAATGACCCCCTGGAGG

CTGCACACGGAGGCAACGTCCTGATCACTGATACCTGGATCAGCATGGGCCAGGAGG

AAGAGAAGAAGAAGCGGCTCCAGGCCTTCCAGGGCTACCAGGTGACAATGAAAACTG

CCAAGGTCGCCGCTTCTGATTGGACTTTTCTGCATTGTCTGCCCCGAAAACCTGAAGAG

GTGGACGATGAGGTCTTCTATTCACCTAGGAGCCTGGTGTTTCCAGAAGCCGAGAATC

GCAAGTGGACAATCATGGCCGTGATGGTGTCCCTGCTGACTGACTATTCCCCACAGCT

GCAGAAGCCTAAGTTTTGAGATATCGTCGACTCGCTGATCAGCCTCGACTGTGCCTTCT

AGTTGCCAGCCATCTGTTGTTTGCCCCTCCCCCGTGCCTTCCTTGACCCTGGAAGGTGC

CACTCCCACTGTCCTTTCCTAATAAAATGAGGAAATTGCATCGCATTGTCTGAGTAGGT

GTCATTCTATTCTGGGGGGTGGGGTGGGGCAGGACAGCAAGGGGGAGGATTGGGAAG

ACAATAGCAGGCATGCTGGGGATGCGGTGGGCTCTATGGCTTCTGAGGCGGAAAGAA

CCAGCTGGGGCTCGACTAGACTAGTCCTGCAGGTAGAGCATGGCTACGTAAGGAACCC

CTAGTGATGGAGTTGGCCACTCCCTCTCTGCGCGCTCGCTCGCTCACTGAGGCCGGGC

GACCAAAGGTCGCCCGACGCCCGGGCTTTGCCCGGGCGGCCTCAGTGAGCGAGCGAG

-continued

CGCGCAGAGAGGGAGTGGCCAACTTTTTGCAAAAGCCTAGGCCTCCAAAAAAGCCTC

CTCACTACTTCTGGAATAGCTCAGAGGCCGAGGCGGCCTCGGCCTCTGCATAAATAAA

AAAAATTAGTCAGCCATGGGGCGGAGAATGGGCGGAACTGGGCGGAGTTAGGGGCGG

GATGGGCGGAGTTAGGGGCGGGACTATGGTTGCTGACTAATTGAGATGCATGCTTTGC

ATACTTCTGCCTGCTGGGGAGCCTGGGGACTTTCCACACCTGGTTGCTGACTAATTGAG

ATGCATGCTTTGCATACTTCTGCCTGCTGGGGAGCCTGGGGACTTTCCACACCCTAACT

GACACACATTCCACAGCTGCATTAATGAATCGGCCAACGCGCGGGGAGAGGCGGTTT

GCGTATTGGGCGCTCTTCCGCTTCCTCGCTCACTGACTCGCTGCGCTCGGTCGTTCGGC

TGCGGCGAGCGGTATCAGCTCACTCAAAGGCGGTAATACGGTTATCCACAGAATCAGG

GGATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCGGAT

ACCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCCGT

TCAGCCCGACCGCTGCGCCTTATCCGGTAACTATCGTCTTGAGTCCAACCCGGTAAGA

CACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAGAA

CAGTATTTGGTATCTGCGCTCTGCTGAAGCCAGTTACCTTCGGAAAAAGAGTTGGTAG

CTCTTGATCCGGCAAACAAACCACCGCTGGTAGCGGTGGTTTTTTTGTTTGCAAGCAGC

AGATTACGCGCAGAAAAAAAGGATCTCAAGAAGATCCTTTGATCTTTTCTACGGGGTC

TGACGCTCAGTGGAACGAAAACTCACGTTAAGGGATTTTGGTCATGAGATTATCAAAA

AGGATCTTCACCTAGATCCTTTTAAATTAAAAATGAAGTTTTAAATCAAGCCCAATCTG

AATAATGTTACAACCAATTAACCAATTCTGATTAGAAAAACTCATCGAGCATCAAATG

AAACTGCAATTTATTCATATCAGGATTATCAATACCATATTTTTGAAAAAGCCGTTTCT

GTAATGAAGGAGAAAACTCACCGAGGCAGTTCCATAGGATGGCAAGATCCTGGTATC

GGTCTGCGATTCCGACTCGTCCAACATCAATACAACCTATTAATTTCCCCTCGTCAAAA

ATAAGGTTATCAAGTGAGAAATCACCATGAGTGACGACTGAATCCGGTGAGAATGGC

AAAAGTTTATGCATTTCTTTCCAGACTTGTTCAACAGGCCAGCCATTACGCTCGTCATC

AAAATCACTCGCATCAACCAAACCGTTATTCATTCGTGATTGCGCCTGAGCGAGACGA

AATACGCGATCGCTGTTAAAAGGACAATTACAAACAGGAATCGAATGCAACCGGCGC

AGGAACACTGCCAGCGCATCAACAATATTTTCACCTGAATCAGGATATTCTTCTAATA

CCTGGAATGCTGTTTTTCCGGGGATCGCAGTGGTGAGTAACCATGCATCATCAGGAGT

ACGGATAAAATGCTTGATGGTCGGAAGAGGCATAAATTCCGTCAGCCAGTTTAGTCTG

ACCATCTCATCTGTAACATCATTGGCAACGCTACCTTTGCCATGTTTCAGAAACAACTC

TGGCGCATCGGGCTTCCCATACAAGCGATAGATTGTCGCACCTGATTGCCCGACATTA

TCGCGAGCCCATTTATACCCATATAAATCAGCATCCATGTTGGAATTTAATCGCGGCCT

CGACGTTTCCCGTTGAATATGGCTCATACCGGTACTCTTCCTTTTTCAATATTATTGAA

GCATTTATCAGGGTTATTGTCTCATGAGCGGATACATATTTGAATGTATTTAGAAAAAT

AAACAAATAGGGGTTCCGCGCACATTTCCCCGAAAAGTGCCACCTGACGTCTAAGAAA

-continued

```
CCATTATTATCATGACATTAACCTATAAAAATAGGCGTATCACGAGGCCCTTTCGTCTC

GCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGG

GTGTTGGCGGGTGTCGGGGCTGGCTTAACTATGCGGCATCAGAGCAGATTGTACTGAG

AGTGCACCATTCGACGCTCTCCCTTATGCGACTCCTGCATTAGGAAGCAGCCCAGTAG

TAGGTTGAGGCCGTTGAGCACCGCCGCCGCAAGGAATGGTGCATGCAAGGAGATGGC

GCCCAACAGTCCCCCGGCCACGGGGCCTGCCACCATACCCACGCCGAAACAAGCGCTC

ATGAGCCCGAAGTGGCGAGCCCGATCTTCCCCATCGGTGATGTCGGCGATATAGGCGC

CAGCAACCGCACCTGTGGCGCCGGTGATGCCGGCCACGATGCGTCCGGCGTAGAGGA

TCTG
```

Exemplary vectors also include pAAV2-hOTCE.hAATp.SV40int.hOTCco.BGHpa having a sequence set forth in SEQ ID NO:28 (where the ITR1 is at nt 262-406, the hOTC enhancer is at nt 446-620, the hAAT promoter is at nt 627-2858, the SV40 intron is at nt 2867-2953, the Kozak sequence is at nt 2973-2979, the huOTC gene is at nt 2980-4044, the BGHpA is at nt 4057-4317, and the ITR2 is at nt 4367-4511), or a vector having at least or about 81%, 82%, 83%, 84%, 85%, 86%, 87%, 88%, 89%, 90%, 91%, 92%, 93%, 94%, 95%, 96%, 97%, 98% or 99% sequence identity thereto whereby the vector can be introduced into a cell for expression of the hOTC gene at levels that are at least or about 50%, 60%, 70%, 80%, 90% or more of the expression levels observed when pAAV2-hOTCE.hAATp.SV40int.hOTCco.BGHpa is introduced into the cell.

```
SEQ ID NO: 28:
GCTAGCGATGACCCTGCTGATTGGTTCGCTGACCATTTCCGGGTGCGGGACGGCGTTA

CCAGAAACTCAGAAGGTTCGTCCAACCAAACCGACTCTGACGGCAGTTTACGAGAGA

GATGATAGGGTCTGCTTCAGTAAGCCAGATGCTACACAATTAGGCTTGTACATATTGT

CGTTAGAACGCGGCTACAATTAATACATAACCTTATGTATCATACACATACGATTTAG

GTGACACTATAGAATACACGGAATTAATTCTTGGCCACTCCCTCTCTGCGCGCTCGCTC

GCTCACTGAGGCCGCCCGGGCAAAGCCCGGGCGTCGGGCGACCTTTGGTCGCCCGGCC

TCAGTGAGCGAGCGAGCGCGCAGAGAGGGAGTGGCCAACTCCATCACTAGGGGTTCC

TTACGTAGCCATGCTCTAGCGATCGCGGTACCTTAATTAATTAGGGCTGATTGTTGAGA

CACTGGTGAACTTTGAACCTCTGTGATTTCCCTGTTTGCTCTGTGCCTGATAGCTTTCA

GTCTGCTAACAAATCTCCTTTATGCAGTTTAACCTCTGTACTTCCAATGGGGAGGAATT

GGAATCAGCCTATGGGAGAAGAGATAGCTCTAGGATTCAGATCTCCCAGTCTTGTGTC

TGCCGGGCAATGAGCAAGGCTCCTTCCTGTCCAAGCTCCCCGCCCCTCCCCAGCCTACT

GCCTCCACCCGAAGTCTACTTCCTGGGTGGGCAGGAACTGGGCACTGTGCCCAGGGCA

TGCACTGCCTCCACGCAGCAACCCTCAGAGTCCTGAGCTGAACCAAGAAGGAGGAGG

GGGTCGGGCCTCCGAGGAAGGCCTAGCCGCTGCTGCTGCCAGGAATTCCAGGTTGGAG

GGGCGGCAACCTCCTGCCAGCCTTCAGGCCACTCTCCTGTGCCTGCCAGAAGAGACAG

AGCTTGAGGAGAGCTTGAGGAGAGCAGGAAAGGTGGGACATTGCTGCTGCTGCTCAC

TCAGTTCCACAGGTGGGAGGGACAGCAGGGCTTAGAGTGGGGGTCATTGTGCAGATG

GGAAAACAAAGGCCCAGAGAGGGGAAGAAATGCCCAGGAGCTACCGAGGGCAGGCG

ACCTCAACCACAGCCCAGTGCTGGAGCTGTGAGTGGATGTAGAGCAGCGGAATATCC

ATTCAGCCAGCTCAGGGGAAGGACAGGGGCCCTGAAGCCAGGGGATGGAGCTGCAGG

GAAGGGAGCTCAGAGAGAAGGGGAGGGGAGTCTGAGCTCAGTTTCCCGCTGCCTGAA

AGGAGGGTGGTACCTACTCCCTTCACAGGGTAACTGAATGAGAGACTGCCTGGAGGA

AAGCTCTTCAAGTGTGGCCCACCCCACCCCAGTGACACCAGCCCCTGACACGGGGGAG
```

-continued

GGAGGGCAGCATCAGGAGGGGCTTTCTGGGCACACCCAGTACCCGTCTCTGAGCTTTC

CTTGAACTGTTGCATTTTAATCCTCACAGCAGCTCAACAAGGTACATACCGTCACCATC

CCCATTTTACAGATAGGGAAATTGAGGCTCGGAGCGGTTAAACAACTCACCTGAGGCC

TCACAGCCAGTAAGTGGGTTCCCTGGTCTGAATGTGTGTGCTGGAGGATCCTGTGGGT

CACTCGCCTGGTAGAGCCCCAAGGTGGAGGCATAAATGGGACTGGTGAATGACAGAA

GGGGCAAAAATGCACTCATCCATTCACTCTGCAAGTATCTACGGCACGTACGCCAGCT

CCCAAGCAGGTTTGCGGGTTGCACAGCGGGCGATGCAATCTGATTTAGGCTTTTAAAG

GGATTGCAATCAAGTGGGGCCCCACTAGCCTCAACCCTGTACCTCCCCTCCCCTCCACC

CCCAGCAGTCTCCAAAGGCCTCCAACAACCCCAGAGTGGGGGCCATGTATCCAAAGA

AACTCCAAGCTGTATACGGATCACACTGGTTTTCCAGGAGCAAAAACAGAAACAGGC

CTGAGGCTGGTCAAAATTGAACCTCCTCCTGCTCTGAGCAGCCTGGGGGGCAGACTAA

GCAGAGGGCTGTGCAGACCCACATAAAGAGCCTACTGTGTGCCAGGCACTTCACCCGA

GGCACTTCACAAGCATGCTTGGGAATGAAACTTCCAACTCTTTGGGATGCAGGTGAAA

CAGTTCCTGGTTCAGAGAGGTGAAGCGGCCTGCCTGAGGCAGCACAGCTCTTCTTTAC

AGATGTGCTTCCCCACCTCTACCCTGTCTCACGGCCCCCCATGCCAGCCTGACGGTTGT

GTCTGCCTCAGTCATGCTCCATTTTTCCATCGGGACCATCAAGAGGGTGTTTGTGTCTA

AGGCTGACTGGGTAACTTTGGATGAGCGGTCTCTCCGCTCTGAGCCTGTTTCCTCATCT

GTCAAATGGGCTCTAACCCACTCTGATCTCCCAGGGCGGCAGTAAGTCTTCAGCATCA

GGCATTTTGGGGTGACTCAGTAAATGGTAGATCTTGCTACCAGTGGAACAGCCACTAA

GGATTCTGCAGTGAGAGCAGAGGGCCAGCTAAGTGGTACTCTCCCAGAGACTGTCTGA

CTCACGCCACCCCCTCCACCTTGGACACAGGACGCTGTGGTTTCTGAGCCAGGTACAA

TGACTCCTTTCGGTAAGTGCAGTGGAAGCTGTACACTGCCCAGGCAAAGCGTCCGGGC

AGCGTAGGCGGGCGACTCAGATCCCAGCCAGTGGACTTAGCCCCTGTTTGCTCCTCCG

ATAACTGGGGTGACCTTGGTTAATATTCACCAGCAGCCTCCCCCGTTGCCCCTCTGGAT

CCACTGCTTAAATACGGACGAGGACAGGGCCCTGTCTCCTCAGCTTCAGGCACCACCA

CTGACCTGGGACAGTGAATGCGGCCGCTCTAAGGTAAATATAAAATTTTTAAGTGTAT

AATGTGTTAAACTACTGATTCTAATTGTTTCTCTCTTTTAGATTCCAACCTTTGGAACTG

ATCTAGAGAATTCGCCGCCACCATGCTGTTTAACCTGAGAATCCTGCTGAATAACGCT

GCCTTTAGGAACGGACATAACTTCATGGTCCGCAACTTTCGCTGTGGCCAGCCTCTCCA

GAACAAAGTGCAGCTGAAGGGGAGGGACCTGCTGACCCTGAAAAATTTCACAGGAGA

GGAAATCAAGTACATGCTGTGGCTGTCTGCCGATCTGAAGTTCCGGATCAAGCAGAAG

GGCGAATATCTGCCACTGCTCCAGGGCAAAAGTCTGGGGATGATCTTCGAAAAGAGG

AGTACTCGGACCAGACTGTCAACAGAGACTGGATTCGCTCTGCTGGGAGGACACCCAT

GCTTTCTGACCACACAGGACATTCATCTGGGCGTGAACGAGTCACTGACCGACACAGC

CCGGGTGCTGAGCAGCATGGCCGATGCCGTGCTGGCACGGGTCTACAAACAGAGCGA

CCTGGATACCCTGGCTAAGGAAGCAAGCATCCCCATCATTAATGGGCTGTCCGACCTG

TATCACCCTATCCAGATTCTGGCCGATTACCTGACCCTCCAGGAGCATTATTCTAGTCT

GAAAGGCCTGACACTGAGCTGGATTGGGGACGGAAACAATATCCTGCACTCCATTATG

ATGTCTGCCGCTAAGTTTGGGATGCACCTCCAGGCAGCCACACCAAAAGGCTACGAAC

CCGATGCCAGTGTGACTAAGCTGGCCGAACAGTATGCTAAAGAGAACGGCACTAAGC

-continued

```
TGCTGCTGACCAATGACCCCCTGGAGGCTGCACACGGAGGCAACGTCCTGATCACTGA

TACCTGGATCAGCATGGGCCAGGAGGAAGAGAAGAAGAAGCGGCTCCAGGCCTTCCA

GGGCTACCAGGTGACAATGAAAACTGCCAAGGTCGCCGCTTCTGATTGGACTTTTCTG

CATTGTCTGCCCCGAAAACCTGAAGAGGTGGACGATGAGGTCTTCTATTCACCTAGGA

GCCTGGTGTTTCCAGAAGCCGAGAATCGCAAGTGGACAATCATGGCCGTGATGGTGTC

CCTGCTGACTGACTATTCCCCACAGCTGCAGAAGCCTAAGTTTTGAGATATCGTCGACT

CGCTGATCAGCCTCGACTGTGCCTTCTAGTTGCCAGCCATCTGTTGTTTGCCCCTCCCC

CGTGCCTTCCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGGTGGGGCA

GGACAGCAAGGGGGAGGATTGGGAAGACAATAGCAGGCATGCTGGGGATGCGGTGG

GCTCTATGGCTTCTGAGGCGGAAAGAACCAGCTGGGGCTCGACTAGACTAGTCCTGCA

GGTAGAGCATGGCTACGTAAGGAACCCCTAGTGATGGAGTTGGCCACTCCCTCTCTGC

GCGCTCGCTCGCTCACTGAGGCCGGGCGACCAAAGGTCGCCCGACGCCCGGGCTTTGC

CCGGGCGGCCTCAGTGAGCGAGCGAGCGCGCAGAGAGGGAGTGGCCAACTTTTTGCA

AAAGCCTAGGCCTCCAAAAAAGCCTCCTCACTACTTCTGGAATAGCTCAGAGGCCGAG

GCGGCCTCGGCCTCTGCATAAATAAAAAAAATTAGTCAGCCATGGGGCGGAGAATGG

GCGGAACTGGGCGGAGTTAGGGGCGGGATGGGCGGAGTTAGGGGCGGGACTATGGTT

GCTGACTAATTGAGATGCATGCTTTGCATACTTCTGCCTGCTGGGGAGCCTGGGGACTT

TCCACACCTGGTTGCTGACTAATTGAGATGCATGCTTTGCATACTTCTGCCTGCTGGGG

AGCCTGGGGACTTTCCACACCCTAACTGACACACATTCCACAGCTGCATTAATGAATC

GGCCAACGCGCGGGGAGAGGCGGTTTGCGTATTGGGCGCTCTTCCGCTTCCTCGCTCA

CTGACTCGCTGCGCTCGGTCGTTCGGCTGCGGCGAGCGGTATCAGCTCACTCAAAGGC

GGTAATACGGTTATCCACAGAATCAGGGGATAACGCAGGAAAGAACATGTGAGCAAA

AGGCCAGCAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCT

CCTGTTCCGACCCTGCCGCTTACCGGATACCTGTCCGCCTTTCTCCCTTCGGGAAGCGT

GGCGCTTTCTCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTATCCGGTAA

CTATCGTCTTGAGTCCAACCCGGTAAGACACGACTTATCGCCACTGGCAGCAGCCACT

GGTAACAGGATTAGCAGAGCGAGGTATGTAGGCGGTGCTACAGAGTTCTTGAAGTGG

TGGCCTAACTACGGCTACACTAGAAGAACAGTATTTGGTATCTGCGCTCTGCTGAAGC

CAGTTACCTTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAACTCACGTT

AAGGGATTTTGGTCATGAGATTATCAAAAAGGATCTTCACCTAGATCCTTTTAAATTA

AAAATGAAGTTTTAAATCAAGCCCAATCTGAATAATGTTACAACCAATTAACCAATTC

TGATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGGC

AGTTCCATAGGATGGCAAGATCCTGGTATCGGTCTGCGATTCCGACTCGTCCAACATC

AATACAACCTATTAATTTCCCCTCGTCAAAAATAAGGTTATCAAGTGAGAAATCACCA
```

-continued

```
TGAGTGACGACTGAATCCGGTGAGAATGGCAAAAGTTTATGCATTTCTTTCCAGACTT

GTTCAACAGGCCAGCCATTACGCTCGTCATCAAAATCACTCGCATCAACCAAACCGTT

ATTCATTCGTGATTGCGCCTGAGCGAGACGAAATACGCGATCGCTGTTAAAAGGACAA

TTACAAACAGGAATCGAATGCAACCGGCGCAGGAACACTGCCAGCGCATCAACAATA

TTTTCACCTGAATCAGGATATTCTTCTAATACCTGGAATGCTGTTTTTCCGGGGATCGC

AGTGGTGAGTAACCATGCATCATCAGGAGTACGGATAAAATGCTTGATGGTCGGAAG

AGGCATAAATTCCGTCAGCCAGTTTAGTCTGACCATCTCATCTGTAACATCATTGGCAA

CGCTACCTTTGCCATGTTTCAGAAACAACTCTGGCGCATCGGGCTTCCCATACAAGCG

ATAGATTGTCGCACCTGATTGCCCGACATTATCGCGAGCCCATTTATACCCATATAAAT

CAGCATCCATGTTGGAATTTAATCGCGGCCTCGACGTTTCCCGTTGAATATGGCTCATA

CCGGTACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTTC

CCCGAAAAGTGCCACCTGACGTCTAAGAAACCATTATTATCATGACATTAACCTATAA

AAATAGGCGTATCACGAGGCCCTTTCGTCTCGCGCGTTTCGGTGATGACGGTGAAAAC

CTCTGACACATGCAGCTCCCGGAGACGGTCACAGCTTGTCTGTAAGCGGATGCCGGGA

GCAGACAAGCCCGTCAGGGCGCGTCAGCGGGTGTTGGCGGGTGTCGGGGCTGGCTTA

ACTATGCGGCATCAGAGCAGATTGTACTGAGAGTGCACCATTCGACGCTCTCCCTTAT

GCGACTCCTGCATTAGGAAGCAGCCCAGTAGTAGGTTGAGGCCGTTGAGCACCGCCGC

CGCAAGGAATGGTGCATGCAAGGAGATGGCGCCCAACAGTCCCCCGGCCACGGGGCC

TGCCACCATACCCACGCCGAAACAAGCGCTCATGAGCCCGAAGTGGCGAGCCCGATCT

TCCCCATCGGTGATGTCGGCGATATAGGCGCCAGCAACCGCACCTGTGGCGCCGGTGA

TGCCGGCCACGATGCGTCCGGCGTAGAGGATCTG
```

Additional vectors include pAAV2-2hOTCE.hOTCp.SV40int.hOTCco.BGHpa having a sequence set forth in SEQ ID NO:29 (where the ITR1 is at nt 262-406, the first copy of the hOTC enhancer is at nt 446-620 and the second copy at nt 621-795, the OTC promoter is at nt 802-1590, the SV40 intron is at nt 1599-1685, the Kozak sequence is at nt 1703-1711, the huOTC gene is at nt 1712-2776, the BGHpA is at nt 2789-3049, and the ITR2 is at nt 3099-3243), or a vector having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; pAAV2-2hOTCE.hOTCp.βgint.hOTCco.BGHpa having a sequence set forth in SEQ ID NO:30 (where the ITR1 is at nt 262-406, the first copy of the hOTC enhancer is at nt 446-620 and the second copy at nt 621-795, the OTC promoter is at nt 802-1590, the betaglobin intron is at nt 1599-2142, the Kozak sequence is at nt 2149-2157, the huOTC gene is at nt 2158-3222, the BGHpA is at nt 3235-3495, and the ITR2 is at nt 3545-3689), or a vector having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; pAAV2-2hOTCE.hAATp.SV40int.hOTCco.BGHpa having a sequence set forth in SEQ ID NO:31 (where the ITR1 is at nt 262-406, the first copy of the hOTC enhancer is at nt 446-620 and the second copy at nt 621-795, the hAAT promoter is at nt 802-1193, the SV40 intron is at nt 1202-1288, the Kozak sequence is at nt 130-1314, the huOTC gene is at nt 1315-2379, the BGHpA is at nt 2392-2652, and the ITR2 is at nt 2702-2846), or a vector having at least or about 81%, 82%, 83%, 84%, 85%, 86%, 87%, 88%, 89%, 90%, 91%, 92%, 93%, 94%, 95%, 96%, 97%, 98%, or 99% sequence identity thereto; or pAAV2-2hOTCE.hAATp.βgint.hOTCco.BGHpa having a sequence set forth in SEQ ID NO:32 (where the ITR1 is at nt 262-406, the first copy of the hOTC enhancer is at nt 446-620 and the second copy at nt 621-795, the hAAT promoter is at nt 802-1193, the betaglobin intron is at nt 1202-1751, the Kozak sequence is at nt 1758-1766, the huOTC gene is at nt 1767-2831, the BGHpA is at nt 2844-3104, and the ITR2 is at nt 3154-3298), or a polynucleotide having at least or about 81%, 82%, 83%, 84%, 85%, 86%, 87%, 88%, 89%, 90%, 91%, 92%, 93%, 94%, 95%, 96%, 97%, 98%, or 99% sequence identity thereto.

In particular embodiments, the vectors are viral vectors, e.g. recombinant AAV, lentiviral, retroviral, adenoviral, herpesviral and hepatitis viral virions. Methods for producing viral vectors that comprise a polynucleotide, such as a polynucleotide of the present disclosure, as part of the vector genome are well known in the art and can be performed by the skilled person without undue experimentation. In particular examples, the vector is a recombinant AAV virion produced by packaging a polynucleotide described herein. Methods for producing a recombinant AAV can include introducing into a packaging cell line a polynucleotide vector or polynucleotide described herein, helper functions for generating a productive AAV infection, and AAV cap and rep genes, and recovering a recombinant AAV from the supernatant of the packaging cell line. Various types of cells can be used as the packaging cell line. For example, packaging cell lines that can be used include, but are not limited to, HEK 293 cells, HeLa cells, and Vero cells, for example as disclosed in US20110201088.

The helper functions may be provided by one or more helper plasmids or helper viruses comprising adenoviral helper genes. Non-limiting examples of the adenoviral helper genes include E1A, E1B, E2A, E4 and VA, which can provide helper functions to AAV packaging. In some embodiments, the AAV cap genes are present in a plasmid. The plasmid can further comprise an AAV rep gene. It is contemplated that the cap genes and/or rep gene from any AAV serotype (including, but not limited to, AAV1, AAV2, AAV4, AAV5, AAV6, AAV7, AAV8, AAV9, and any variants thereof) can be used to produce the recombinant AAV disclosed herein. However, typically the encoded AAV capsids are liver-tropic, such as, for example, capsids from AAV serotype 2, 3 and 8.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

In some instances, recombinant AAV is produced by using a cell line that stably expresses some of the necessary components for AAV virion production. For example, a plasmid (or multiple plasmids) comprising AAV rep and cap genes, and a selectable marker, such as a neomycin resistance gene, can be integrated into the genome of a cell (the packaging cells). The packaging cell line can then be co-infected with a helper virus (e.g., adenovirus providing the helper functions) and an AAV vector described herein. The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the AAV vector and the rep-cap genes can be stably integrated into the DNA of producer cells, and the helper functions can be provided by a wild-type adenovirus to produce the recombinant AAV.

As will be appreciated by a skilled artisan, any method suitable for purifying AAV can be used in the embodiments described herein to purify AAV vectors comprising a polynucleotide described herein, and such methods are well known in the art. For example, the recombinant AAV can be isolated and purified from packaging cells and/or the supernatant of the packaging cells. In some embodiments, the AAV is purified by separation method using a CsCl gradient. In other embodiments, AAV is purified as described in US20020136710 using a solid support that includes a matrix to which an artificial receptor or receptor-like molecule that mediates AAV attachment is immobilized.

Host Cells and Transgene Expression Therein

Also provided herein are host cells comprising a polynucleotide or vector of the present disclosure. In some instances, the host cells are used to amplify, replicate, package and/or purify a polynucleotide or vector. In other examples, the host cells are used to express a transgene contained in the polynucleotide or vector. Thus, the present disclosure also contemplates methods for the expression of a transgene, in which a polynucleotide or vector of the present invention is introduced into a host cell, typically, a liver cell. Those skilled in the art would appreciate the conditions under which the polynucleotide or vector can be introduced into a host cell and the conditions that support or facilitate expression of the transgene within the cell. Furthermore, the methods may be in vitro, ex vivo or in vivo.

Exemplary host cells include prokaryotic and eukaryotic cells. In some instances, the host cell is a mammalian host cell. In instances where the cells are used to package a viral vector described herein, the cells may also be transfected with one or more plasmids or infected with one or more viruses that provide the necessary helper and accessory molecules for packaging. In further examples, the host cells may stably express, such as from the genome, one or more helper and accessory molecules. It is well within the skill of a skilled artisan to select an appropriate host cell for the amplification, replication, packaging and/or purification of a vector or recombinant virion of the present invention. Exemplary mammalian host cells include, but are not limited to, HEK-293 cells, HeLa cells, Vero cells, HUH7 cells, and HepG2 cells. In particular examples, for expression of a transgene from a polynucleotide or vector described herein, the host cell is a liver-derived cell, such as, for example, HUH7 and HepG2 cells, or a liver cell isolated from a subject.

Pharmaceutical Compositions and Methods of Administration

Also provided are pharmaceutical compositions comprising the polynucleotides or vectors disclosed herein and a pharmaceutically acceptable carrier. The compositions can also comprise additional ingredients such as diluents, stabilizers, excipients, and adjuvants.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

In instances where the compositions comprise polynucleotides or polynucleotide vectors (e.g. plasmids), the polynucleotides or polynucleotide vectors may be present as "naked DNA" or formulated in a delivery vehicle, such as, for example microparticles or nanoparticles, including liposomes, micelles, lipidic particles, ceramic/inorganic particles, and virus-like particles.

The polynucleotides or vectors disclosed herein can be administered to a subject (e.g., a human) in need thereof, such as a subject with a disease or condition amendable to treatment with a protein, peptide or polynucleotide encoded by the transgene present in the polynucleotides and vectors. Diseases or conditions that may be treated by administration of the polynucleotides and vectors include liver-associated diseases, such as, for example, ornithine transcarbamylase (OTC) deficiency, alpha 1-antitrypsin deficiency, type I tyrosinemia, Progressive Familial Intrahepatic Cholestasis type III, Wilsons' disease, Crigler-Najjar syndrome type I, type IIa familial hypercholesterolemia, coagulation disorders (e.g. hemophilia A and B, afibrogenemiahemophilia, von Willebrand's disease), viral infections of the liver (e.g. hepatitis virus infections, including hepatitis C virus), and liver cancers.

In particular embodiments, the polynucleotides and vectors comprise a hOTC gene and are administered to a subject for the treatment of OTC deficiency. OTC deficiency is an X-linked recessive genetic disorder and the most common urea cycle disorder in humans. OTC deficiency can be caused by a range of mutations in the OTC gene that result in reduced protein expression, activity and/or stability, which in turn result in varying degrees of hyperammonemia. Typically, mutations that essentially eliminate OTC activity result in the severe, neonatal-onset form of OTC deficiency while mutations leading to decreased OTC activity result in the late-onset phenotypes. The polynucleotides and vectors described herein can be administered to subjects with OTC deficiency to treat OTC deficiency, and to treat or prevent hyperammonemia associated with OTC deficiency.

Where the pharmaceutical compositions comprise a viral vector of the present disclosure, such as an AAV vector, titers of recombinant virions to be administered will vary depending on, for example, the particular recombinant virus, the disease or disorder to be treated, the mode of administration, the treatment goal, and the individual to be treated, and can be determined by methods well known to those skilled in the art. Although the exact dosage will be determined on an individual basis, typically recombinant viruses of the present invention are administered to a subject at a dose of between $1\times10^{10}$ genome copies of the recombinant virus per kg of the subject and $1\times10^{14}$ genome copies per kg.

Where the compositions comprise a polynucleotide or polynucleotide vector of the present disclosure, such as a plasmid, the amount of DNA to be administered will vary depending on, for example, the additional use of delivery vehicle and the type of delivery vehicle, the disease or disorder to be treated, the mode of administration, the treatment goal, and the individual to be treated, and can be determined by methods well known to those skilled in the art. Although the exact dosage will be determined on an individual basis, typically compositions of the present invention that comprise a polynucleotide or polynucleotide vector are administered to a subject at a dose of between 10 ng to 500 μg DNA per kg of the subject.

The route of the administration is not particularly limited. For example, a therapeutically effective amount of the polynucleotide or vector can be administered to the subject by via, for example, intramuscular, intravaginal, intravenous, intraperitoneal, subcutaneous, epicutaneous, intradermal, rectal, intraocular, pulmonary, intracranial, intraosseous, oral, buccal, or nasal routes. The polynucleotide or vector can be administered as a single dose or multiple doses, and at varying intervals.

The present invention also contemplates combination therapies, wherein polynucleotides and vectors described herein are coadministered with other suitable agents that may facilitate the desired therapeutic or prophylactic outcome. By "coadministered" is meant simultaneous administration in the same formulation or in two different formulations via the same or different routes or sequential administration by the same or different routes. By "sequential" administration is meant a time difference of from seconds, minutes, hours or days between the administration of the agents. Administration may be in any order.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1. Production of rAAV

AAv Vector Plasmids

A series of plasmids containing a hOTC transgene were produced using standard molecular biology techniques for subsequent production of rAAV vectors and expression of human OTC. Each plasmid was constructed by inserting a codon-optimised human ornithine transcarbamylase (hOTC) coding sequence into a rAAV2 genome under the transcriptional control of a liver-specific promoter. In most instances, either one or two copies of a hOTC enhancer were placed 5' of either a hOTC promoter or a hAAT promoter, which was operably linked to the codon-optimized hOTC gene. The promoter and hOTC gene were separated by either a SV40 intron or beta-globulin intron, and a Kozac sequence was incorporated 5' of the hOTC gene to enhance translation. A (BGH) poly(A) termination signal was also included downstream of the hOTC gene. The hOTC promoters used in the plasmids were either a truncated 789 bp hOTC promoter (SEQ ID NO:2) or a longer 2232 bp hOTC promoter (SEQ ID NO: 1). The hAAT promoters used in the plasmids were either a truncated 392 bp hAAT promoter (SEQ ID NO:4) or a longer 2232 bp hAAT promoter (SEQ ID NO:3). Table 2 sets forth the elements contained within each plasmid and FIG. 1 provides a schematic of pAAV2-OTCE.hAATp.SV40int.huOTCco.BGHpA and pAAV2-OTCE.huOTCp.SV40int. huOTCco.BGHpA.

TABLE 2

| Plasmid | Elements (from 5'-3') |
| --- | --- |
| pAAV2-hOTCE.hOTCp.SV40int.hOTCco.BGHpa (SEQ ID NO: 27) | 5'AAV ITR (SEQ ID NO: 13)<br>hOTC enhancer (SEQ ID NO: 5)<br>hOTC promoter (2232 bp; SEQ ID NO: 1)<br>SV40 intron (SEQ ID NO: 11)<br>Kozac sequence (SEQ ID NO: 10)<br>hOTC gene (SEQ ID NO: 8)<br>(BGH) poly(A) (SEQ ID NO: 9)<br>3'AAV ITR (SEQ ID NO: 14)<br>Sequence of the construct encompassing the 5' AAV ITR through the 3'AAV ITR: SEQ ID NO: 16 (4250 bp) |

TABLE 2-continued

| Plasmid | Elements (from 5'-3') |
|---|---|
| pAAV2-hOTCE.hAATp.SV40int.hOTCco.BGHpa (SEQ ID NO: 28) | 5'AAV ITR (SEQ ID NO: 13)<br>hOTC enhancer (SEQ ID NO: 5)<br>hAAT promoter (2232 bp; SEQ ID NO: 3)<br>SV40 intron (SEQ ID NO: 11)<br>Kozac sequence (SEQ ID NO: 10)<br>hOTC gene (SEQ ID NO: 8)<br>(BGH) poly(A) (SEQ ID NO: 9)<br>3'AAV ITR (SEQ ID NO: 14)<br>Sequence of the construct encompassing the 5' AAV ITR through the 3'AAV ITR: SEQ ID NO: 18 (4250 bp) |
| pAAV2-2hOTCE.hOTCp.SV40int.hOTCco.BGHpa (SEQ ID NO: 29) | 5'AAV ITR (SEQ ID NO: 13)<br>2 x hOTC enhancer (SEQ ID NO: 5)<br>hOTC promoter (789 bp; SEQ ID NO: 2)<br>SV40 intron (SEQ ID NO: 11)<br>Kozac sequence (SEQ ID NO: 10)<br>hOTC gene (SEQ ID NO: 8)<br>(BGH) poly(A) (SEQ ID NO: 9)<br>3'AAV ITR (SEQ ID NO: 14)<br>Sequence of the construct encompassing the 5' AAV ITR through the 3'AAV ITR: SEQ ID NO: 20 (2982 bp) |
| pAAV2-2hOTCE.hOTCp.βgint.hOTCco.BGHpa (SEQ ID NO: 30) | 5'AAV ITR (SEQ ID NO: 13)<br>2 x hOTC enhancer (SEQ ID NO: 5)<br>hOTC promoter (789 bp; SEQ ID NO: 2)<br>beta globulin intron (SEQ ID NO: 12)<br>Kozac sequence (SEQ ID NO: 10)<br>hOTC gene (SEQ ID NO: 8)<br>(BGH) poly(A) (SEQ ID NO: 9)<br>3'AAV ITR (SEQ ID NO: 14)<br>Sequence of the construct encompassing the 5' AAV ITR through the 3'AAV ITR: SEQ ID NO: 22 (3428 bp) |
| pAAV2-2hOTCE.hAATp.SV40int.hOTCco.BGHpa (SEQ ID NO: 31) | 5'AAV ITR (SEQ ID NO: 13)<br>2 x hOTC enhancer (SEQ ID NO: 5)<br>hAAT promoter (392 bp; SEQ ID NO: 4)<br>SV40 intron (SEQ ID NO: 11)<br>Kozac sequence (SEQ ID NO: 10)<br>hOTC gene (SEQ ID NO: 8)<br>(BGH) poly(A) (SEQ ID NO: 9)<br>3'AAV ITR (SEQ ID NO: 14)<br>Sequence of the construct encompassing the 5' AAV ITR through the 3'AAV ITR: SEQ ID NO: 24 (2585 bp) |
| pAAV2-2hOTCE.hAATp.βgint.hOTCco.BGHpa (SEQ ID NO: 32) | 5'AAV ITR (SEQ ID NO: 13)<br>2 x hOTC enhancer (SEQ ID NO: 5)<br>hAAT promoter (392 bp; SEQ ID NO: 4)<br>beta-globulin intron (SEQ ID NO: 12)<br>Kozac sequence (SEQ ID NO: 10)<br>hOTC gene (SEQ ID NO: 8)<br>(BGH) poly(A) (SEQ ID NO: 9)<br>3'AAV ITR (SEQ ID NO: 14)<br>Sequence of the construct encompassing the 5' AAV ITR through the 3'AAV ITR: SEQ ID NO: 26 (3037 bp) |

Packaging of AAV Vector Plasmids

Vector constructs were pseudoserotyped with liver-tropic vector capsids, and human embryonic kidney (HEK) 293 cells were used to produce viral particles having vector genomes of different sizes, as shown in Table 3. The different genome sizes were due predominantly to the different sizes of the hAAT and hOTC promoters used in the constructs, as described above, but also to the specific intronic sequences used.

TABLE 3

| rAAV | Vector genome size (% wild-type) |
|---|---|
| rAAV2/8-hOTCE.hOTCp.SV40int.hOTCco.BGHpa | 90% |
| rAAV2/8-hOTCE.hAATp.SV40int.hOTCco.BGHpa | 90% |
| rAAV2/8-2hOTCE.hOTCp.SV40int.hOTCco.BGHpa | 73% |
| rAAV2/8-2hOTCE.hOTCp.βgint.hOTCco.BGHpa | 83% |
| rAAV2/8-2hOTCE.hAATp.SV40int.hOTCco.BGHpa | 55% |
| rAAV2/8-2hOTCE.hAATp.βgint.hOTCco.BGHpa | 65% |

Briefly, HEK-293 were plated in Dulbecco's modified DMEM supplemented with 10% FBS (complete DMEM) at $4\times10^6$ cells per 100 mm diameter plate and incubated at 37° C. overnight in a humidified 5% $CO_2$ environment. The next day, the media in each dish was replaced with fresh media. A calcium phosphate transfection mix was prepared containing plasmids encoding adenovirus helper functions (pXX6, 6 μg), AAV capsid proteins, the plasmid (1 μg), and either p5E18-VD2/8 (serotype 8; courtesy of James M. Wilson, University of Pennsylvania) or pLK03. The transfection mix was dispensed to plates, which were then incubated overnight at 37° C. in a humidified 5% $CO_2$ environment. After a medium change with DMEM supplemented with 2% FBS at 18 to 24 hours post-transfection, cells were harvested 48 hours post-transfection. The cells were pelleted at 400×g for 10 minutes, resuspended at 1 mL per plate in buffer (100 mM NaCl, 2 mM $MgCl_2$, 10 mM Tris.HCl, pH8) and stored at −80° C. before purification.

Purification of AAV Vectors (rAAV) for In Vivo Delivery

HEK-293 cells containing rAAV were subjected to three freeze-thaw cycles. Cellular debris was pelleted by centrifugation at 3000×g for 10 minutes and supernatant was treated with Benzonase (Sigma) at 50 U/mL at 37° C. for 30 minutes to remove unencapsulated DNA. Centrifugation at 3000×g for 10 minutes was followed by two precipitation steps, the first using a one-third volume of ice-cold saturated $(NH_4)_2SO_4$ in PBS (pH 7.0) and incubation on ice for 10 minutes. After centrifugation at 3000×g for 15 minutes, the supernatant was retained and subjected to a second precipitation with two-third volume of ice-cold saturated $(NH_4)_2SO_4$ in PBS (pH 7.0) and incubation on ice for 20 minutes. The final precipitation step was followed by centrifugation at 12,000×g for 15 minutes. The rAAV-containing pellet was resuspended in CsCl solution in PBS (d=1.37, pH7.5), 20 mL for every 40 plates, and divided into two 10 mL centrifuge tubes. Using a pasteur pipette, 1 mL of CsCl (d=1.5) was added beneath each suspension, which were then subjected to 150,000×g in a Beckman SW41 rotor at 16° C. for 36-48 hours.

Fractions (1 mL) were collected from the bottom of each tube after piercing with a 19 gauge needle. Virus containing fractions were identified by PCR, pooled and dialysed against PBS (with calcium and magnesium) using a Slide-A-Lyzer Dialysis Cassette (10,000 MWCO, Pierce). A final dialysis was performed at 4° C. against 20 mM Tris (pH8.0)/1 mM $MgCl_2$/150 mM NaCl/5% glycerol for 4 hours to overnight.

The purified rAAV was subjected to a final concentration step using a Vivaspin-20 column (100,000 MWCO, Sartorius) which was centrifuged at 3000×g/4° C. until the volume was reduced to less than 1 mL. The titre of the virus stock was determined using quantitative PCR.

Quantitation of Vector Genomes

AAV vector genomes were quantitated by quantitative PCR (qPCR) using the Takara SYBR Premix Ex Taq kit according to manufacturer's instruction and with the following primers: OTC-specific forward primer (5'-CGATGCCAGTGTGACTAAGC-3': SEQ ID NO: 33); OTC-specific reverse primer (5'-GGAGCCGCTTCTTCTTCTCT-3': SEQ ID NO: 34). Known quantities of linearised plasmid DNA containing the OTC gene were included in each run to generate a standard curve and permit quantitation of vector genomes. Tubes were cycled in a Rotorgene 2000 or Rotor GENE-Q thermal cycler (QIAGEN) at 95° C.-30 seconds followed by 40 cycles of 95° C.-5 sec, 58° C.-15 sec, 72° C.-20 sec, and 86° C.-15 sec. Melt curves (60-99° C.) were determined at completion of the reaction to ensure a single PCR product was specifically synthesised. All samples were analysed in duplicate. Averages were determined and the number of vector genomes per mL was calculated from the standard curve.

Figure 2:
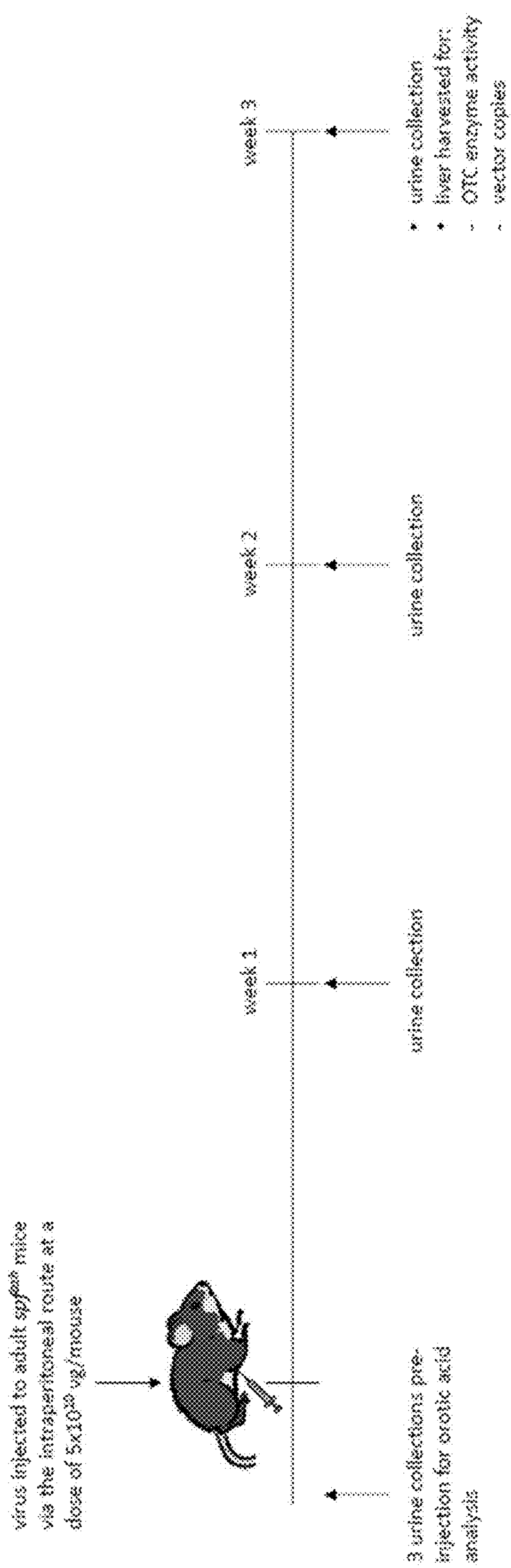
FIG. 2 shows the experimental design of a study to assess rAAV for their ability to correct the phenotype in a mouse model of OTC deficiency (the $spf^{ash}$ mouse model).

Example 2. Gene Therapy in a Mouse Model of OTC Deficiency rAAV were assessed for their ability to correct the phenotype in a mouse model of OTC deficiency (the $spf^{ash}$ mouse model, using strain B6EiC3Sn a/A-$Otc^{spf-ash}$/J). rAAV diluted in PBS were administered to young adult mice by injection via the intraperitoneal route at a dose of $5\times10^{10}$ vg/mouse in 100 μL. The experimental design is outlined in FIG. 2. Urine was collected prior to injection and then at weeks 1, 2 and 3 for orotic acid analysis. Mice were sacrificed at week 3 and the liver was harvested and analysed for OTC activity and vector copies.

Orotic Acid Assay

Urine was collected over a 24 hour period on Whatman filter paper, eluted, and analyzed for orotic acid levels using Liquid Chromatography/Tandem Mass Spectrometry. Results were standardized against creatinine levels, measured by the modified Jaffe reaction.

OTC Activity Assay

OTC enzyme activity was determined based on the methods described in (Ye et al. (1996) J Biol Chem 271: 3639-3646). In brief, liver was homogenised in Mitochondrial Lysis Buffer (0.5% v/v TritonX-100, 10 mM HEPES pH7.4, 2 mM DTT, with protease inhibitors added). The homogenate was frozen and thawed three times in liquid nitrogen, centrifuged at 12,000×g for 10 min at 4° C., and the supernatant removed, aliquoted and stored at −80° C.

Protein was quantitated using the BioRad DC Protein Assay Kit. Samples were diluted appropriately and added (0.5 to 40 μg, in 5 μL) to the ornithine reaction mixture (270 mM Triethanolamine, 5 mM Ornithine, 15 mM Carbamyl Phosphate, in a final volume of 700 μL), and incubated for 30 min at 37° C. The reaction was stopped with 250 μL of 3:1 phosphoric acid:sulfuric acid. Enzyme activity was determined based on citrulline production which was detected by the addition of 50 μL of 3% 2,3-butanedione monoxime followed by incubation at 95-100° C. in the dark for 15 min. Absorbance was measured at 490 nm. One unit of OTC activity equals the amount of enzyme catalysing the formation of 1 μmole of citrulline per min at 37° C.

Vector Copy Analysis

Vector copies were detected in extracted DNA from liver lysates by quantitative PCR as described above. DNA concentration was normalized by quantitation of GAPDH using the Quantitect SYBR Green Kit (Qiagen) and the following primer set (which binds in exon 3): forward primer 5'-ACGGCAAATTCAACGGCAC-3' (SEQ ID NO:35); reverse primer 5'-TAGTGGGGTCTCGCTCCTGG-3' (SEQ ID NO:36). A standard curve was established using two-fold dilutions of genomic DNA.

Results

Figure 3:
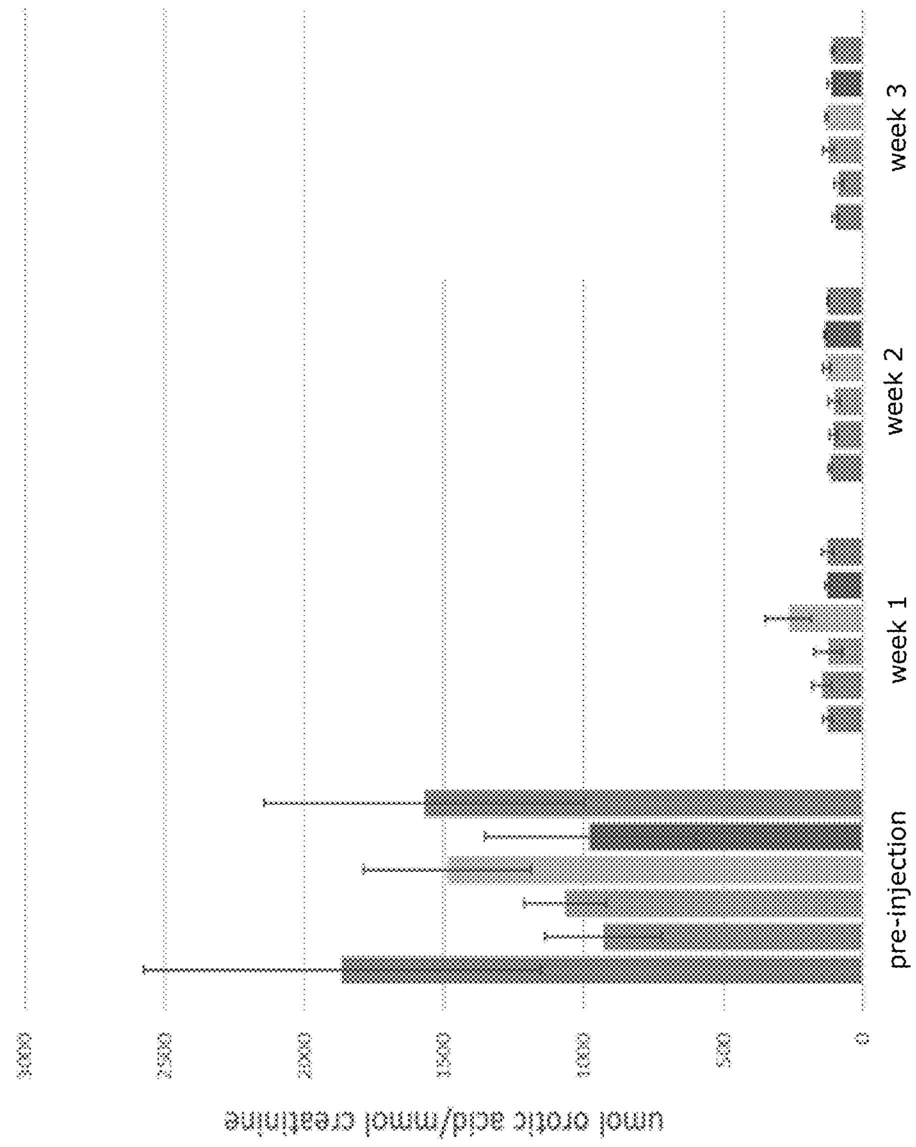
FIG. 3 presents the results of an analysis of the levels of orotic acid in the urine of $spf^{ash}$ mice before and after administration of $5\times10^{10}$ vg of the various rAAV. For each time point in the graph, the bars represent, from left to right, levels of orotic acid in mice that were to receive, or that received, rAAV2/8-2hOTCE.hAATp.SV40int.hOTCco.BGHpa, rAAV2/8-2hOTCE.hAATp.βgint.hOTCco. BGHpa, rAAV2/8-2hOTCE.hOTCp.SV40int.hOTCco.BGHpa, rAAV2/8-2hOTCE. hOTCp.βgint.hOTCco.BGHpa, rAAV2/8-hOTCE.hAATp.SV40int.hOTCco.BGHpa or rAAV2/8-hOTCE.hOTCp.SV40int.hOTCco.BGHpa.
Figure 4:
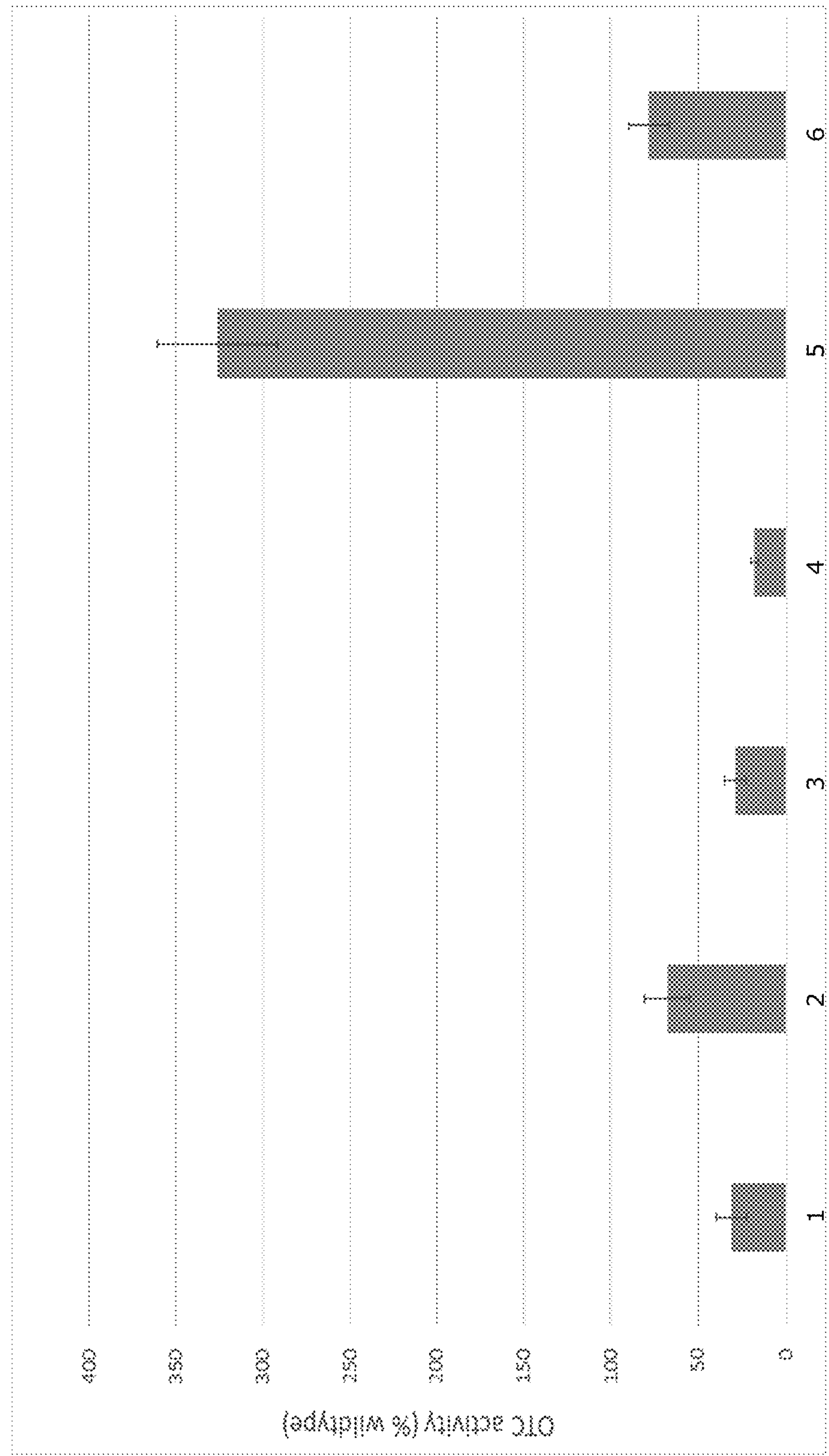
FIG. 4 presents the results of an analysis of the levels of OTC activity (expressed as a percentage of wild-type levels) in the liver lysate of $spf^{ash}$ mice following administration of $5\times10^{10}$ vg of the various rAAV: (1) rAAV2/8-2hOTCE.hAATp.SV40int.hOTCco.BGHpa, (2) rAAV2/8-2hOTCE.hAATp. 3gint.hOTCco.BGHpa, (3) rAAV2/8-2hOTCE.hOTCp.SV40int. hOTCco.BGHpa, (4) rAAV2/8-2hOTCE.hOTCp.βgint.hOTCco.BGHpa, (5) rAAV2/8-hOTCE.hAATp(2232).SV40int.hOTCco.BGHpa and (6) rAAV2/8-hOTCE.hOTCp(2232).SV40int.hOTCco.BGHpa.

As shown in FIG. 3, all of the AAV vectors that were assessed (and which contained the hOTC gene under transcriptional control of the hOTC or hAAT promoter and hOTC enhancer) reduced urinary orotic acid to wild type levels within one week of administration. This is despite there being varying levels of OTC activity. As shown in FIG. 4, administration of rAAV2/8-hOTCE.hAATp.SV40int.hOTCco.BGHpa resulted in over 326% of wild-type OTC activity in the liver, while administration of rAAV2/8-hOTCE.hOTCp.SV40int.hOTCco.BGHpa resulted in 78% of wild-type OTC activity in the liver. The vectors that contained two copies of the hOTC enhancer with the truncated hOTC or hAAT vectors resulted in even lower OTC activity in the liver, as low as 31% for rAAV2/8-2hOTCE.hOTCp.βgint.hOTCco.BGHpa.

Figure 5:
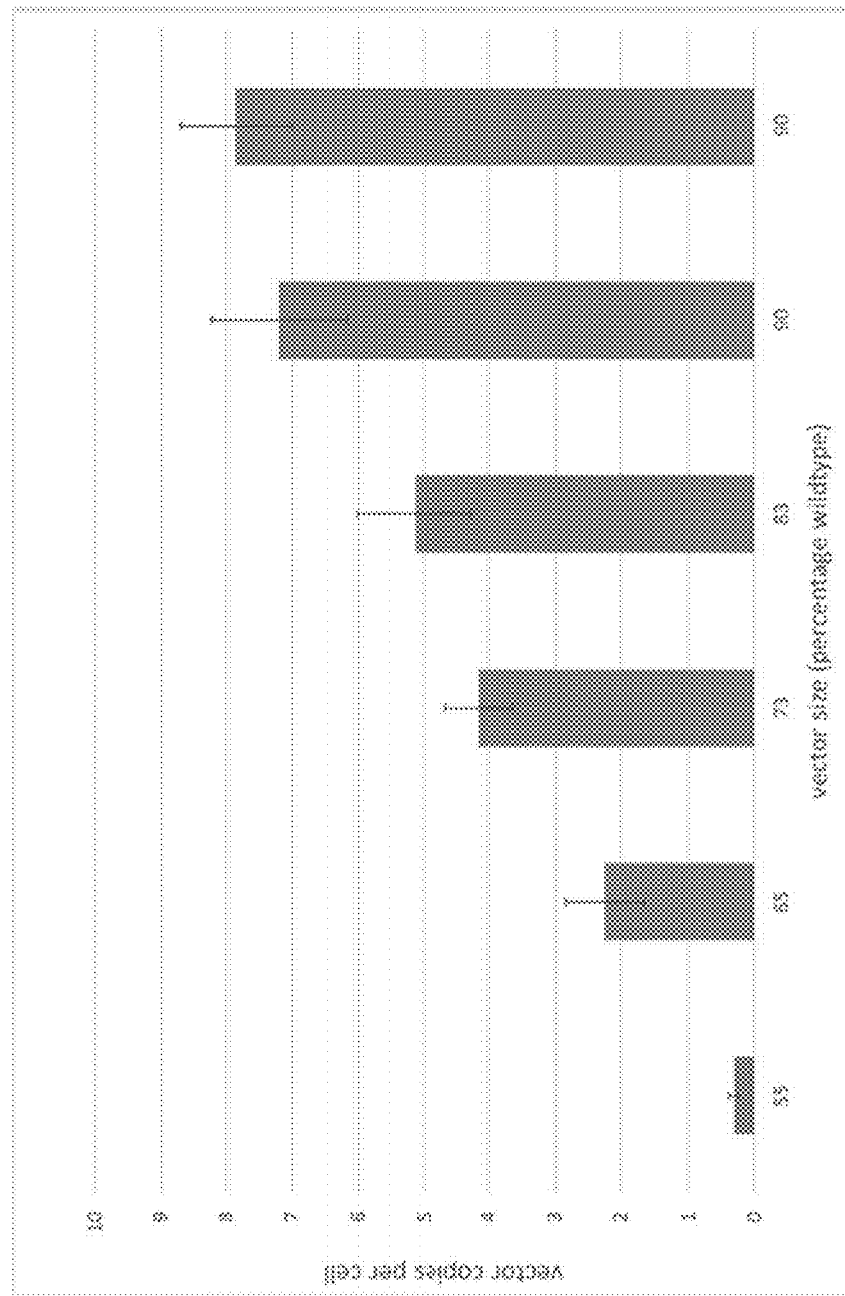
FIG. 5 presents an analysis of the number of vector copies per cell in the liver of $spf^{ash}$ mice following administration of rAAV. The results are shown as vector copies per cell for each of the different sized rAAV (with vector size expressed as a % of wild-type, from left to right of the graph): 55% (rAAV2/8-2hOTCE.hAATp.SV40int.hOTCco.BGHpa), 65% (rAAV2/8-2hOTCE.hAATp.βgint. hOTCco.BGHpa), 73% (rAAV2/8-2hOTCE.hOTCp.SV40int.hOTCco.BGHpa), 83% (rAAV2/8-2hOTCE.hOTCp.βgint.hOTCco.BGHpa), 90% (rAAV2/8-hOTCE. hAATp(2232).SV40int.hOTCco.BGHpa) or 90% (rAAV2/8-hOTCE.hOTCp.SV40int. hOTCco.BGHpa).

The transduction efficiency of the vectors was assessed by analyzing the number of vector copies per cell in the liver samples at 3 weeks post injection. As shown in FIG. 5, this varied quite significantly and correlated with the size of the vector genome. rAAV having a smaller vector genome (as a percentage of wild-type) had a much lower number of vector copies per cell than those rAAV with larger genomes. It is possible that this result reflects incorrect dosing resulting from errors in the titration of the rAAV having smaller genomes. This could be due to inefficient packaging as a result of the small genome size, whereby rAAV with smaller genomes package additional DNA to "fill" the virion. This additional DNA may then be misidentified during the titration assay as an additional virion, resulting in a calculated titre that is higher than the actual titre. This in turn results in rAAV doses that are lower than intended, and a resulting low "observed" transduction efficiency. In contrast, rAAV having vector genomes that are close to the wild-type vector size (i.e. rAAV2/8-hOTCE.hOTCp.SV40int.hOTCco.BGHpa and rAAV2/8-hOTCE.hAATp.SV40int.hOTCco.BGHpa) exhibited much higher vector copies per cell, possibly as a result of more efficient packaging and thus more accurate titration and dosing.

Figure 6:
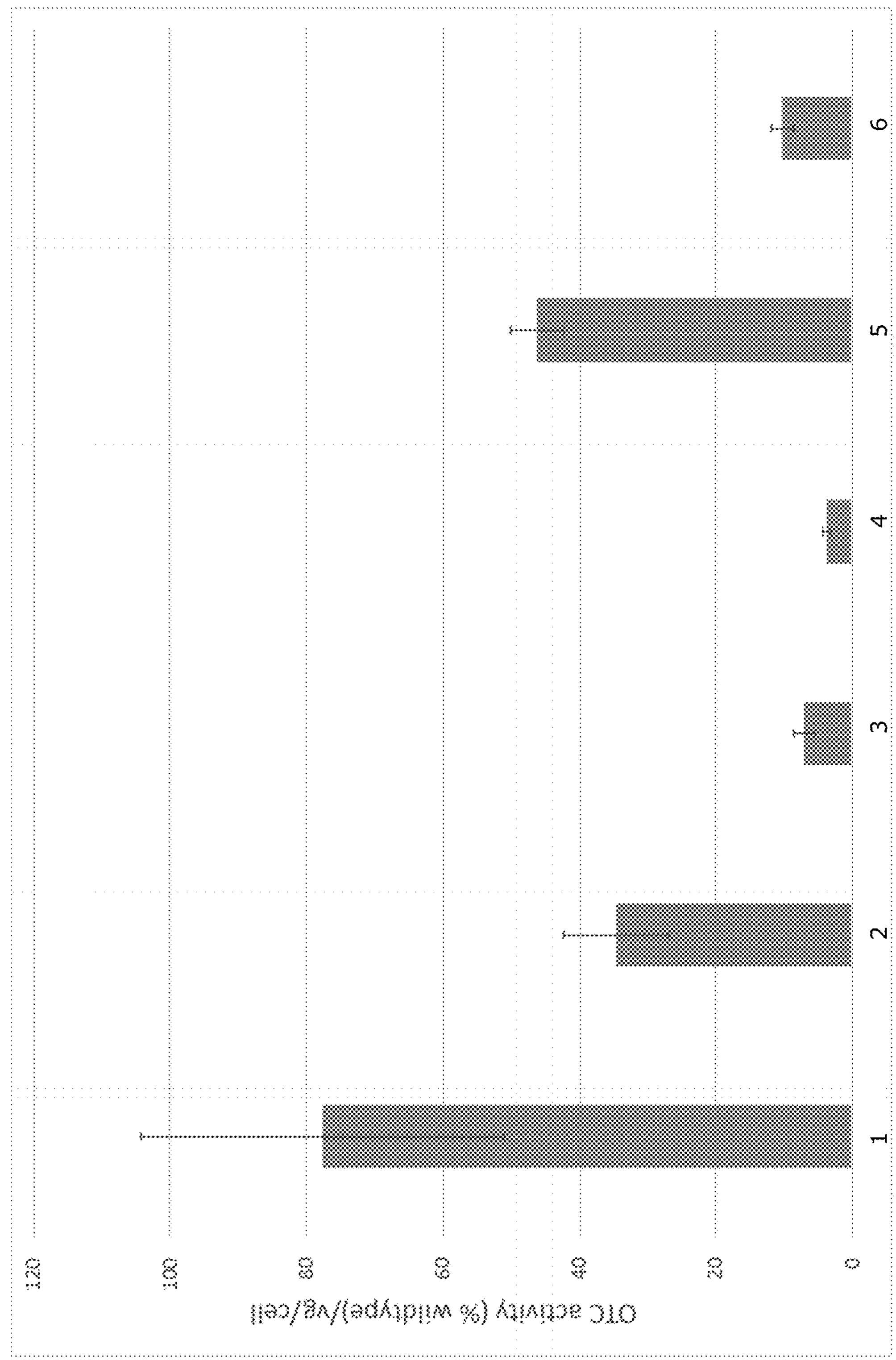
FIG. 6 presents the results of an analysis of the levels of OTC activity per vector copy (expressed as a percentage of wild-type levels) in the liver of spf$^{ash}$ mice following administration of $5\times10^{10}$ vg of the various rAAV: (1) rAAV2/8-2hOTCE.hAATp.SV40int.hOTCco.BGHpa, (2) rAAV2/8-2hOTCE.hAATp.βgint.hOTCco.BGHpa, (3) rAAV2/8-2hOTCE.hOTCp.SV40int.hOTCco.BGHpa, (4) rAAV2/8-2hOTCE. hOTCp.βgint.hOTCco.BGHpa, (5) rAAV2/8-hOTCE.hAATp.SV40int.hOTCco.BGHpa and (6) rAAV2/8-hOTCE. hOTCp.SV40int.hOTCco.BGHpa.

When the OTC activity per vector copy was analysed, it was observed that vectors with the hAAT promoter generally exhibited stronger hOTC expression than vectors with the hOTC promoter, and the SV40 intron generally resulted in greater expression of the hOTC gene than the beta-globulin intron (FIG. 6). While the inclusion of two OTC enhancers produced the greatest amount of OTC activity, the use of particularly strong enhancers can have drawbacks for gene therapy in humans, with the potential for enhancement of non-target, oncogenes in the subject.

The invention claimed is:

1. A polynucleotide comprising the sequence of SEQ ID NO: 17 or a sequence having at least or about 99% sequence identity thereto, wherein the polynucleotide can express a functional ornithine transcarbamylase (OTC) polypeptide.

2. A vector, comprising the polynucleotide of claim 1.

3. The vector of claim 2, wherein the vector is selected from the group consisting of an AAV, lentiviral, retroviral, adenoviral, herpesviral, and hepatitis viral vector.

4. A method for expressing a human ornithine transcarbamylase (hOTC) transgene in a host cell, the method comprising introducing the polynucleotide of claim 1 into the host cell to thereby facilitate expression of the hOTC transgene present in the polynucleotide in the host cell.

5. A method of treating ornithine transcarbamylase (OTC) deficiency in a subject, the method comprising administering to the subject the polynucleotide of claim 1.

6. The method of claim 4, wherein the polynucleotide is in an AAV vector.

7. The method of claim 5, wherein the polynucleotide is in an AAV vector.

* * * * *

SEQUENCE LISTING

```
<160> NUMBER OF SEQ ID NOS: 36

<210> SEQ ID NO 1
<211> LENGTH: 2232
<212> TYPE: DNA
<213> ORGANISM: Homo sapiens

<400> SEQUENCE: 1

acaagaaagt taaaattgaa ttagaggaat catggggtca acaagagccc ctggatgaat     60

tctgaggatg aacatcaaag cctgtaaagt aaaacagact ccacatgtga cataatcagc    120

agaagctggg tagttgaaat ctacccctca acaagttcat tgagatgccc tgccttttga    180

gattcagtga aattgctttt aacttcatcc cacttgtgat gcagctcccc ttttccaatc    240

cctctgggag ttattggtat cttaactttt ttttagttcc ctctggcttt gagctcctgc    300

atctgtagca ttaggagggt ttgtgagttg ctttggcatc tcagaaatgc tgcctgtact    360

ctctagcatg gaactgcaga cacttcttga tttctcccca agcattacca atatgagttg    420

tgtgtatggc tagcacagtt cagtgaagat atggggtcaa gctatgggct ttatattagc    480

ctgtggtttg gcctcatctc cctcaggctc catgcaaacg ttcaatttca ctcctgtatt    540

atgtggagcg cttttgctct ctgaaaccta ttcaataact ggccttgttt gcctcttcaa    600

agatgcttta ttatgttttt taaattcact ctctcccttc tcacctctgt acctttgcaa    660

gcagttgctt ctgcctggaa tatcctttcc agaatggaag atttggtaga ggttgggaaa    720

tgtcagtctt tcccctcact ttatctcaca tcattctctg taagtagaag gaaatggtga    780

caatatttat ttctctacta gtattaatta tgacatcaca aacatctcgg ctcctgaggt    840
```

```
ggccatagtt ggtctttaaa taacactttt tggtattcca caaacttctg gaaaatattt    900
acttgggttt gctaaagtca tataaattga ccagaagagg cagccctacc cctgcccctc    960
ctctccttcc tcctaccctt cctaccttag agggctcccg cttcttcgaa gccagacaac   1020
tttgtctgga cctctcctat gggcttgtat tatggatatt tgtttataaa tcataccacc   1080
tttactgaac tgtgaactct gcaaagatga tgtcatcttc cctctctgaa acttcagtgc   1140
agctcggtat ctgatacaga attgactttg aatcacctga tttctaactg aggataaatg   1200
aataaatgtg aagttgcaga tggcccctta gtgatctgaa taggctgcta ggggaagagc   1260
atatggtatc cccacttccc acttgtactg actgtcaggt gctgttagaa tcaataggca   1320
actatttctt ttctttttct ttctttcttt cttttttttg agacagtgtc tctctctgtc   1380
acccaggctg gagtacagtg gtgcaatctg ggctcactgc aacctctgtc tcccgggttc   1440
aagcgactct catgcctcag cctcccaaat agctgggatt acaggtgtgc accaccacgt   1500
ctagctaatt tttgtatttt tagtggagac ggggattcac catgttggcc aggctggtct   1560
cgaactcctg ggctcaagtg atccgcccgc ctcagcctcc caaagtgctg ggattacagg   1620
cgtgagccac cgtgcccggc cagcaattat ttctttattg aagacttatg tgcaaggcac   1680
aaagggagct ccaggactga gatattttta ctataccttc tctatcatct tgcacccccca  1740
aaatagcttc cagggcactt ctttctattt gtttttgtgg aaagactggc aattagaggt   1800
agaaaagtga aataaatgga aatagtacta ctcaggactg tcacatctac atctgtgttt   1860
ttgcagtgcc aatttgcatt ttctgagtga gttacttcta ctcaccttca cagcagccgg   1920
taccgcagtg ccttgcatat attatatcct caatgagtac ttgtcaattg attttgtaca   1980
tgcgtgtgac agtataaata tattatgaaa aatgaggagg ccaggcaata aaagagtcag   2040
gatttcttcc aaaaaaaata cacagcggtg gagcttggca taaagttcaa atgctcctac   2100
accctgccct gcagtatctc taaccagggg actttgataa ggaagctgaa gggtgatatt   2160
acctttgctc cctcactgca actgaacaca tttcttagtt tttaggtggc cccgctggc    2220
taacttgctg tg                                                       2232
```

<210> SEQ ID NO 2
<211> LENGTH: 789
<212> TYPE: DNA
<213> ORGANISM: Homo sapiens

<400> SEQUENCE: 2

```
caagcgactc tcatgcctca gcctcccaaa tagctgggat tacaggtgtg caccaccacg     60
tctagctaat ttttgtattt ttagtggaga cggggattca tcatgttggc caggctggtc    120
tcgaactcct gggctcaagt gatccgcccg cctcagcctc ccaaagtgct gggattatag    180
gcgtgagcca ccatgcccgg ccagcaatta tttctttatt gaagacttat gtgcaaggca    240
caaagggagc tccaggactg agatattttt actatacctt ctctatcatc ttgcaccccc    300
aaaatagctt ccagggcact tctatttgtt tttgtggaaa gactggcaat tagaggtaga    360
aaagtgaaat aaatggaaat agtactactc agggctgtca catctacatc tgtgtttttg    420
cagtgccaat ttgcattttc tgagtgagtt acttctactc accttcacag cagccagtac    480
cgcagtgcct tgcatatatt atatcctcaa tgagtacttg tcaattgatt ttgtacatgc    540
gtgtgacagt ataaatatat tatgaaaaat gaggaggcca ggcaataaaa gagtcaggat    600
ttcttccaaa aaaaatacac agcggtggag cttggcataa agttcaaatg ctcctacacc    660
ctgccctgca gtatctctaa ccaggggact ttgataagga agctgaaggg tgatattacc    720
```

```
tttgctccct cactgcaact gaacacattt cttagttttt aggtggcccc cgctggctaa    780

cttgctgtg                                                            789


<210> SEQ ID NO 3
<211> LENGTH: 2232
<212> TYPE: DNA
<213> ORGANISM: Homo sapiens

<400> SEQUENCE: 3

cccagtcttg tgtctgccgg gcaatgagca aggctccttc ctgtccaagc tccccgcccc     60

tccccagcct actgcctcca cccgaagtct acttcctggg tgggcaggaa ctgggcactg    120

tgcccagggc atgcactgcc tccacgcagc aaccctcaga gtcctgagct gaaccaagaa    180

ggaggagggg gtcgggcctc cgaggaaggc ctagccgctg ctgctgccag gaattccagg    240

ttggaggggc ggcaacctcc tgccagcctt caggccactc tcctgtgcct gccagaagag    300

acagagcttg aggagagctt gaggagagca ggaaaggtgg gacattgctg ctgctgctca    360

ctcagttcca caggtgggag ggacagcagg gcttagagtg ggggtcattg tgcagatggg    420

aaaacaaagg cccagagagg ggaagaaatg cccaggagct accgagggca ggcgacctca    480

accacagccc agtgctggag ctgtgagtgg atgtagagca gcggaatatc cattcagcca    540

gctcagggga aggacagggg ccctgaagcc aggggatgga gctgcaggga agggagctca    600

gagagaaggg gaggggagtc tgagctcagt ttcccgctgc ctgaaaggag ggtggtacct    660

actcccttca cagggtaact gaatgagaga ctgcctggag gaaagctctt caagtgtggc    720

ccaccccacc ccagtgacac cagcccctga cacgggggag ggagggcagc atcaggaggg    780

gctttctggg cacacccagt acccgtctct gagctttcct tgaactgttg cattttaatc    840

ctcacagcag ctcaacaagg tacataccgt caccatcccc attttacaga tagggaaatt    900

gaggctcgga gcggttaaac aactcacctg aggcctcaca gccagtaagt gggttccctg    960

gtctgaatgt gtgtgctgga ggatcctgtg ggtcactcgc ctggtagagc cccaaggtgg   1020

aggcataaat gggactggtg aatgacagaa ggggcaaaaa tgcactcatc cattcactct   1080

gcaagtatct acggcacgta cgccagctcc caagcaggtt tgcgggttgc acagcgggcg   1140

atgcaatctg atttaggctt ttaaagggat tgcaatcaag tggggcccca ctagcctcaa   1200

ccctgtacct cccctcccct ccacccccag cagtctccaa aggcctccaa caaccccaga   1260

gtgggggcca tgtatccaaa gaaactccaa gctgtatacg gatcacactg gttttccagg   1320

agcaaaaaca gaaacaggcc tgaggctggt caaaattgaa cctcctcctg ctctgagcag   1380

cctgggggc agactaagca gagggctgtg cagacccaca taaagagcct actgtgtgcc   1440

aggcacttca cccgaggcac ttcacaagca tgcttgggaa tgaaacttcc aactctttgg   1500

gatgcaggtg aaacagttcc tggttcagag aggtgaagcg gcctgcctga ggcagcacag   1560

ctcttcttta cagatgtgct tccccacctc taccctgtct cacggccccc catgccagcc   1620

tgacggttgt gtctgcctca gtcatgctcc atttttccat cgggaccatc aagagggtgt   1680

ttgtgtctaa ggctgactgg gtaactttgg atgagcggtc tctccgctct gagcctgttt   1740

cctcatctgt caaatgggct ctaacccact ctgatctccc agggcggcag taagtcttca   1800

gcatcaggca ttttggggtg actcagtaaa tggtagatct tgctaccagt ggaacagcca   1860

ctaaggattc tgcagtgaga gcagagggcc agctaagtgg tactctccca gagactgtct   1920

gactcacgcc accccctcca ccttggacac aggacgctgt ggtttctgag ccaggtacaa   1980
```

-continued

```
tgactccttt cggtaagtgc agtggaagct gtacactgcc caggcaaagc gtccgggcag   2040

cgtaggcggg cgactcagat cccagccagt ggacttagcc cctgtttgct cctccgataa   2100

ctggggtgac cttggttaat attcaccagc agcctccccc gttgcccctc tggatccact   2160

gcttaaatac ggacgaggac agggccctgt ctcctcagct tcaggcacca ccactgacct   2220

gggacagtga at                                                       2232


<210> SEQ ID NO 4
<211> LENGTH: 392
<212> TYPE: DNA
<213> ORGANISM: Homo sapiens

<400> SEQUENCE: 4

tgctaccagt ggaacagcca ctaaggattc tgcagtgaga gcagagggcc agctaagtgg     60

tactctccca gagactgtct gactcacgcc accccctcca ccttggacac aggacgctgt    120

ggtttctgag ccaggtacaa tgactccttt cggtaagtgc agtggaagct gtacactgcc    180

caggcaaagc gtccgggcag cgtaggcggg cgactcagat cccagccagt ggacttagcc    240

cctgtttgct cctccgataa ctggggtgac cttggttaat attcaccagc agcctccccc    300

gttgcccctc tggatccact gcttaaatac ggacgaggac agggccctgt ctcctcagct    360

tcaggcacca ccactgacct gggacagtga at                                  392


<210> SEQ ID NO 5
<211> LENGTH: 175
<212> TYPE: DNA
<213> ORGANISM: Homo sapiens

<400> SEQUENCE: 5

ttagggctga ttgttgagac actggtgaac tttgaacctc tgtgatttcc ctgtttgctc     60

tgtgcctgat agctttcagt ctgctaacaa atctccttta tgcagtttaa cctctgtact    120

tccaatgggg aggaattgga atcagcctat gggagaagag atagctctag gattc         175


<210> SEQ ID NO 6
<211> LENGTH: 354
<212> TYPE: PRT
<213> ORGANISM: Homo sapiens

<400> SEQUENCE: 6

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
```

```
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe


<210> SEQ ID NO 7
<211> LENGTH: 1464
<212> TYPE: DNA
<213> ORGANISM: Homo sapiens

<400> SEQUENCE: 7

aagctgaagg gtgatattac ctttgctccc tcactgcaac tgaacacatt tcttagtttt      60

taggtggccc ccgctggcta acttgctgtg gagttttcaa gggcatagaa tcgtccttta     120

cacaattaaa agaagatgct gtttaatctg aggatcctgt taaacaatgc agcttttaga     180

aatggtcaca acttcatggt tcgaaatttt cggtgtggac aaccactaca aaataaagtg     240

cagctgaagg gccgtgacct tctcactcta aaaaacttta ccggagaaga aattaaatat     300

atgctatggc tatcagcaga tctgaaattt aggataaaac agaaaggaga gtatttgcct     360

ttattgcagg ggaagtcctt aggcatgatt tttgagaaaa gaagtactcg aacaagattg     420

tctacagaaa caggctttgc acttctggga ggacatcctt gttttcctac cacacaagat     480

attcatttgg gtgtgaatga aagtctcacg gacacggccc gtgtattgtc tagcatggca     540

gatgcagtat tggctcgagt gtataaacaa tcagatttgg acacccttgc taaagaagca     600

tccatcccaa ttatcaatgg gctgtcagat ttgtaccatc ctatccagat cctggctgat     660

tacctcacgc tccaggaaca ctatagctct ctgaaaggtc ttaccctcag ctgtttcggg     720

gatgggaaca atatcctgca ctccatcatg atgagcgcag cgaaattcgg aatgcacctt     780

caggcagcta ctccaaaggg ttatgagccg gatgctagtg taaccaagtt ggcagagcag     840
```

```
tatgccaaag agaatggtac caagctgttg ctgacaaatg atccattgga agcagcgcat    900

ggaggcaatg tattaattac agacacttgg ataagcatgg gacgagaaga ggagaagaaa    960

aagcggctcc aagctttcca aggttaccaa gttacaatga agactgctaa agttgctgcc   1020

tctgactgga catttttaca ctgcttgccc agaaagccag aagaagtgga tgatgaagtc   1080

ttttattctc ctcgatcact agtgttccca gaggcagaaa acagaaagtg gacaatcatg   1140

gctgtcatgg tgtccctgct gacagattac tcacctcagc tccagaagcc taaattttga   1200

tgttgtgtta cttgtcaaga aagaagcaat gttggtcagt aacagaatga gttggtttat   1260

ggggaaaaga gaagagaatc taaaaaaataa accaatccct aacacgtggt atgggcgaat   1320

cgtacgatat gctttgccat tgtgaaactt tccttaagcc ttcaatttaa gtgctgatgc   1380

actgtaatac gtgcttaact ttgcttaaac tctctaattc ccaatttctg agttacattt   1440

agatatcata ttaactatca tata                                          1464
```

```
<210> SEQ ID NO 8
<211> LENGTH: 1065
<212> TYPE: DNA
<213> ORGANISM: Artificial Sequence
<220> FEATURE:
<223> OTHER INFORMATION: Codon-optimized human OTC coding sequence

<400> SEQUENCE: 8

atgctgttta acctgagaat cctgctgaat aacgctgcct ttaggaacgg acataacttc     60

atggtccgca actttcgctg tggccagcct ctccagaaca aagtgcagct gaaggggagg    120

gacctgctga ccctgaaaaa tttcacagga gaggaaatca agtacatgct gtggctgtct    180

gccgatctga agttccggat caagcagaag ggcgaatatc tgccactgct ccagggcaaa    240

agtctgggga tgatcttcga aaagaggagt actcggacca gactgtcaac agagactgga    300

ttcgctctgc tgggaggaca cccatgcttt ctgaccacac aggacattca tctgggcgtg    360

aacgagtcac tgaccgacac agcccgggtg ctgagcagca tggccgatgc cgtgctggca    420

cgggtctaca aacagagcga cctggatacc ctggctaagg aagcaagcat ccccatcatt    480

aatgggctgt ccgacctgta tcaccctatc cagattctgg ccgattacct gaccctccag    540

gagcattatt ctagtctgaa aggcctgaca ctgagctgga ttggggacgg aaacaatatc    600

ctgcactcca ttatgatgtc tgccgctaag tttgggatgc acctccaggc agccacacca    660

aaaggctacg aacccgatgc cagtgtgact aagctggccg aacagtatgc taaagagaac    720

ggcactaagc tgctgctgac caatgacccc ctggaggctg cacacggagg caacgtcctg    780

atcactgata cctggatcag catgggccag gaggaagaga agaagaagcg gctccaggcc    840

ttccagggct accaggtgac aatgaaaact gccaaggtcg ccgcttctga ttggactttt    900

ctgcattgtc tgccccgaaa acctgaagag gtggacgatg aggtcttcta ttcacctagg    960

agcctggtgt ttccagaagc cgagaatcgc aagtggacaa tcatggccgt gatggtgtcc   1020

ctgctgactg actattcccc acagctgcag aagcctaagt tttga                   1065
```

```
<210> SEQ ID NO 9
<211> LENGTH: 261
<212> TYPE: DNA
<213> ORGANISM: Bos taurus

<400> SEQUENCE: 9

tcgctgatca gcctcgactg tgccttctag ttgccagcca tctgttgttt gcccctcccc     60

cgtgccttcc ttgaccctgg aaggtgccac tcccactgtc ctttcctaat aaaatgagga    120
```

aattgcatcg cattgtctga gtaggtgtca ttctattctg gggggtgggg tggggcagga 180
cagcaagggg gaggattggg aagacaatag caggcatgct ggggatgcgg tgggctctat 240
ggcttctgag gcggaaagaa c 261

<210> SEQ ID NO 10
<211> LENGTH: 7
<212> TYPE: DNA
<213> ORGANISM: Artificial Sequence
<220> FEATURE:
<223> OTHER INFORMATION: Kozac sequence

<400> SEQUENCE: 10 cgccacc 7

<210> SEQ ID NO 11
<211> LENGTH: 87
<212> TYPE: DNA
<213> ORGANISM: Artificial sequence
<220> FEATURE:
<223> OTHER INFORMATION: Simian virus 40

<400> SEQUENCE: 11
tctaaggtaa atataaaatt tttaagtgta taatgtgtta aactactgat tctaattgtt 60
tctctctttt agattccaac ctttgga 87

<210> SEQ ID NO 12
<211> LENGTH: 550
<212> TYPE: DNA
<213> ORGANISM: Homo sapiens

<400> SEQUENCE: 12
tgagaacttc agggtgagtc tatgggaccc ttgatgtttt ctttcccctt cttttctatg 60
gttaagttca tgtcatagga aggggagaag taacagggta cacatattga ccaaatcagg 120
gtaattttgc atttgtaatt ttaaaaaatg ctttcttctt ttaatatact tttttgttta 180
tcttatttct aatactttcc ctaatctctt tctttcaggg caataatgat acaatgtatc 240
atgcctcttt gcaccattct aaagaataac agtgataatt tctgggttaa ggcaatagca 300
atatttctgc atataaatat ttctgcatat aaattgtaac tgatgtaaga ggtttcatat 360
tgctaatagc agctacaatc cagctaccat tctgctttta ttttatggtt gggataaggc 420
tggattattc tgagtccaag ctaggccctt ttgctaatca tgttcatacc tcttatcttc 480
ctcccacagc tcctgggcaa cgtgctggtc tgtgtgctgg cccatcactt tggcaaagca 540
cgtgagatct 550

<210> SEQ ID NO 13
<211> LENGTH: 145
<212> TYPE: DNA
<213> ORGANISM: adeno-associated virus

<400> SEQUENCE: 13
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcct 145

<210> SEQ ID NO 14
<211> LENGTH: 145
<212> TYPE: DNA

<213> ORGANISM: adeno-associated virus

<400> SEQUENCE: 14

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145
```

<210> SEQ ID NO 15
<211> LENGTH: 3872
<212> TYPE: DNA
<213> ORGANISM: Artificial sequence
<220> FEATURE:
<223> OTHER INFORMATION: hOTCenh.hOTCprom.SV40int.hOTCco.BGHpa expression cassette

<400> SEQUENCE: 15

```
ttagggctga ttgttgagac actggtgaac tttgaacctc tgtgatttcc ctgtttgctc     60

tgtgcctgat agctttcagt ctgctaacaa atctccttta tgcagtttaa cctctgtact    120

tccaatgggg aggaattgga atcagcctat gggagaagag atagctctag gattcagatc    180

tacaagaaag ttaaaattga attagaggaa tcatggggtc aacaagagcc cctggatgaa    240

ttctgaggat gaacatcaaa gcctgtaaag taaaacagac tccacatgtg acataatcag    300

cagaagctgg gtagttgaaa tctacccctc aacaagttca ttgagatgcc ctgccttttg    360

agattcagtg aaattgcttt taacttcatc ccacttgtga tgcagctccc cttttccaat    420

ccctctggga gttattggta tcttaacttt tttttagttc cctctggctt tgagctcctg    480

catctgtagc attaggaggg tttgtgagtt gctttggcat ctcagaaatg ctgcctgtac    540

tctctagcat ggaactgcag acacttcttg atttctcccc aagcattacc aatatgagtt    600

gtgtgtatgg ctagcacagt tcagtgaaga tatggggtca agctatgggc tttatattag    660

cctgtggttt ggcctcatct ccctcaggct ccatgcaaac gttcaatttc actcctgtat    720

tatgtggagc gcttttgctc tctgaaacct attcaataac tggccttgtt tgcctcttca    780

aagatgcttt attatgtttt ttaaattcac tctctccctt ctcacctctg tacctttgca    840

agcagttgct tctgcctgga atatcctttc cagaatggaa gatttggtag aggttgggaa    900

atgtcagtct ttcccctcac tttatctcac atcattctct gtaagtagaa ggaaatggtg    960

acaatattta tttctctact agtattaatt atgacatcac aaacatctcg gctcctgagg   1020

tggccatagt tggtctttaa ataacacttt ttggtattcc acaaacttct ggaaaatatt   1080

tacttgggtt tgctaaagtc atataaattg accagaagag gcagccctac ccctgcccct   1140

cctctccttc ctcctaccct tcctacctta gagggctccc gcttcttcga agccagacaa   1200

ctttgtctgg acctctccta tggcttgta ttatggatat ttgtttataa atcataccac   1260

ctttactgaa ctgtgaactc tgcaaagatg atgtcatctt ccctctctga aacttcagtg   1320

cagctcggta tctgatacag aattgacttt gaatcacctg atttctaact gaggataaat   1380

gaataaatgt gaagttgcag atggcccctt agtgatctga ataggctgct aggggaagag   1440

catatggtat ccccacttcc cacttgtact gactgtcagg tgctgttaga atcaataggc   1500

aactatttct tttctttttc tttctttctt tctttttttt gagacagtgt ctctctctgt   1560

cacccaggct ggagtacagt ggtgcaatct gggctcactg caacctctgt ctcccgggtt   1620

caagcgactc tcatgcctca gcctcccaaa tagctgggat tacaggtgtg caccaccacg   1680

tctagctaat tttgtatttt ttagtggaga cggggattca ccatgttggc caggctggtc   1740
```

```
tcgaactcct gggctcaagt gatccgcccg cctcagcctc ccaaagtgct gggattacag   1800
gcgtgagcca ccgtgcccgg ccagcaatta tttctttatt gaagacttat gtgcaaggca   1860
caaagggagc tccaggactg agatattttt actatacctt ctctatcatc ttgcaccccc   1920
aaaatagctt ccagggcact tctttctatt tgtttttgtg gaaagactgg caattagagg   1980
tagaaaagtg aaataaatgg aaatagtact actcaggact gtcacatcta catctgtgtt   2040
tttgcagtgc caatttgcat ttctgagtg agttacttct actcaccttc acagcagccg    2100
gtaccgcagt gccttgcata tattatatcc tcaatgagta cttgtcaatt gattttgtac   2160
atgcgtgtga cagtataaat atattatgaa aaatgaggag gccaggcaat aaaagagtca   2220
ggatttcttc caaaaaaaat acacagcggt ggagcttggc ataaagttca aatgctccta   2280
caccctgccc tgcagtatct ctaaccaggg gactttgata aggaagctga agggtgatat   2340
tacctttgct ccctcactgc aactgaacac atttcttagt ttttaggtgg cccccgctgg   2400
ctaacttgct gtggcggccg ctctaaggta aatataaaat ttttaagtgt ataatgtgtt   2460
aaactactga ttctaattgt ttctctcttt tagattccaa cctttggaac tgatctagag   2520
aattcgccgc caccatgctg tttaacctga gaatcctgct gaataacgct gcctttagga   2580
acggacataa cttcatggtc cgcaactttc gctgtggcca gcctctccag aacaaagtgc   2640
agctgaaggg gagggacctg ctgaccctga aaaatttcac aggagaggaa atcaagtaca   2700
tgctgtggct gtctgccgat ctgaagttcc ggatcaagca gaagggcgaa tatctgccac   2760
tgctccaggg caaaagtctg ggatgatct tcgaaaagag gagtactcgg accagactgt    2820
caacagagac tggattcgct ctgctgggag gacacccatg ctttctgacc acacaggaca   2880
ttcatctggg cgtgaacgag tcactgaccg acacagcccg ggtgctgagc agcatggccg   2940
atgccgtgct ggcacgggtc tacaaacaga gcgacctgga taccctggct aaggaagcaa   3000
gcatccccat cattaatggg ctgtccgacc tgtatcaccc tatccagatt ctggccgatt   3060
acctgaccct ccaggagcat tattctagtc tgaaaggcct gacactgagc tggattgggg   3120
acggaaacaa tatcctgcac tccattatga tgtctgccgc taagtttggg atgcacctcc   3180
aggcagccac accaaaaggc tacgaacccg atgccagtgt gactaagctg gccgaacagt   3240
atgctaaaga gaacggcact aagctgctgc tgaccaatga cccccctggag gctgcacacg  3300
gaggcaacgt cctgatcact gatacctgga tcagcatggg ccaggaggaa gagaagaaga   3360
agcggctcca ggccttccag ggctaccagg tgacaatgaa aactgccaag gtcgccgctt   3420
ctgattggac ttttctgcat tgtctgcccc gaaaacctga agaggtggac gatgaggtct   3480
tctattcacc taggagcctg gtgtttccag aagccgagaa tcgcaagtgg acaatcatgg   3540
ccgtgatggt gtccctgctg actgactatt ccccacagct gcagaagcct aagttttgag   3600
atatcgtcga ctcgctgatc agcctcgact gtgccttcta gttgccagcc atctgttgtt   3660
tgcccctccc ccgtgccttc cttgaccctg gaaggtgcca ctcccactgt cctttcctaa   3720
taaaatgagg aaattgcatc gcattgtctg agtaggtgtc attctattct ggggggtggg   3780
gtggggcagg acagcaaggg ggaggattgg gaagacaata gcaggcatgc tggggatgcg   3840
gtgggctcta tggcttctga ggcggaaaga ac                                 3872
```

```
<210> SEQ ID NO 16
<211> LENGTH: 4250
<212> TYPE: DNA
<213> ORGANISM: Artificial sequence
<220> FEATURE:
<223> OTHER INFORMATION: AAV2-hOTCenh.hOTCprom.SV40int.hOTCco.BGHpa
```

expression cassette

<400> SEQUENCE: 16

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttccttacgt agccatgctc tagcgatcgc ggtaccttaa    180
ttaattaggg ctgattgttg agacactggt gaactttgaa cctctgtgat ttccctgttt    240
gctctgtgcc tgatagcttt cagtctgcta acaaatctcc tttatgcagt ttaacctctg    300
tacttccaat ggggaggaat tggaatcagc ctatgggaga agagatagct ctaggattca    360
gatctacaag aaagttaaaa ttgaattaga ggaatcatgg ggtcaacaag agcccctgga    420
tgaattctga ggatgaacat caaagcctgt aaagtaaaac agactccaca tgtgacataa    480
tcagcagaag ctgggtagtt gaaatctacc cctcaacaag ttcattgaga tgccctgcct    540
tttgagattc agtgaaattg cttttaactt catcccactt gtgatgcagc tccccttttc    600
caatccctct gggagttatt ggtatcttaa cttttttta gttccctctg gctttgagct    660
cctgcatctg tagcattagg agggtttgtg agttgctttg gcatctcaga aatgctgcct    720
gtactctcta gcatggaact gcagacactt cttgatttct ccccaagcat taccaatatg    780
agttgtgtgt atggctagca cagttcagtg aagatatggg gtcaagctat gggctttata    840
ttagcctgtg gtttggcctc atctccctca ggctccatgc aaacgttcaa tttcactcct    900
gtattatgtg gagcgctttt gctctctgaa acctattcaa taactggcct tgtttgcctc    960
ttcaaagatg ctttattatg ttttttaaat tcactctctc ccttctcacc tctgtacctt   1020
tgcaagcagt tgcttctgcc tggaatatcc tttccagaat ggaagatttg gtagaggttg   1080
ggaaatgtca gtctttcccc tcactttatc tcacatcatt ctctgtaagt agaaggaaat   1140
ggtgacaata tttatttctc tactagtatt aattatgaca tcacaaacat ctcggctcct   1200
gaggtggcca tagttggtct ttaaataaca ctttttggta ttccacaaac ttctggaaaa   1260
tatttacttg ggtttgctaa agtcatataa attgaccaga agaggcagcc ctacccctgc   1320
ccctcctctc cttcctccta cccttcctac cttagagggc tcccgcttct tcgaagccag   1380
acaactttgt ctggacctct cctatgggct tgtattatgg atatttgttt ataaatcata   1440
ccacctttac tgaactgtga actctgcaaa gatgatgtca tcttccctct ctgaaacttc   1500
agtgcagctc ggtatctgat acagaattga ctttgaatca cctgatttct aactgaggat   1560
aaatgaataa atgtgaagtt gcagatggcc ccttagtgat ctgaataggc tgctagggga   1620
agagcatatg gtatccccac ttcccacttg tactgactgt caggtgctgt tagaatcaat   1680
aggcaactat ttcttttctt tttctttctt tctttctttt ttttgagaca gtgtctctct   1740
ctgtcaccca ggctggagta cagtggtgca atctgggctc actgcaacct ctgtctcccg   1800
ggttcaagcg actctcatgc ctcagcctcc caaatagctg ggattacagg tgtgcaccac   1860
cacgtctagc taatttttgt atttttagtg gagacgggga ttcaccatgt tggccaggct   1920
ggtctcgaac tcctgggctc aagtgatccg cccgcctcag cctcccaaag tgctgggatt   1980
acaggcgtga gccaccgtgc ccggccagca attatttctt tattgaagac ttatgtgcaa   2040
ggcacaaagg gagctccagg actgagatat ttttactata ccttctctat catcttgcac   2100
ccccaaaata gcttccaggg cacttctttc tatttgtttt tgtggaaaga ctggcaatta   2160
gaggtagaaa agtgaaataa atggaaatag tactactcag gactgtcaca tctacatctg   2220
tgtttttgca gtgccaattt gcattttctg agtgagttac ttctactcac cttcacagca   2280
```

```
gccggtaccg cagtgccttg catatattat atcctcaatg agtacttgtc aattgatttt   2340

gtacatgcgt gtgacagtat aaatatatta tgaaaaatga ggaggccagg caataaaaga   2400

gtcaggattt cttccaaaaa aaatacacag cggtggagct tggcataaag ttcaaatgct   2460

cctacaccct gccctgcagt atctctaacc aggggacttt gataaggaag ctgaagggtg   2520

atattacctt tgctccctca ctgcaactga acacatttct tagtttttag gtggcccccg   2580

ctggctaact tgctgtggcg gccgctctaa ggtaaatata aaatttttaa gtgtataatg   2640

tgttaaacta ctgattctaa ttgtttctct cttttagatt ccaacctttg gaactgatct   2700

agagaattcg ccgccaccat gctgtttaac ctgagaatcc tgctgaataa cgctgccttt   2760

aggaacggac ataacttcat ggtccgcaac tttcgctgtg gccagcctct ccagaacaaa   2820

gtgcagctga aggggaggga cctgctgacc ctgaaaaatt tcacaggaga ggaaatcaag   2880

tacatgctgt ggctgtctgc cgatctgaag ttccggatca agcagaaggg cgaatatctg   2940

ccactgctcc agggcaaaag tctggggatg atcttcgaaa agaggagtac tcggaccaga   3000

ctgtcaacag agactggatt cgctctgctg ggaggacacc catgctttct gaccacacag   3060

gacattcatc tgggcgtgaa cgagtcactg accgacacag cccgggtgct gagcagcatg   3120

gccgatgccg tgctggcacg ggtctacaaa cagagcgacc tggataccct ggctaaggaa   3180

gcaagcatcc ccatcattaa tgggctgtcc gacctgtatc accctatcca gattctggcc   3240

gattacctga ccctccagga gcattattct agtctgaaag gcctgacact gagctggatt   3300

ggggacggaa acaatatcct gcactccatt atgatgtctg ccgctaagtt tgggatgcac   3360

ctccaggcag ccacaccaaa aggctacgaa cccgatgcca gtgtgactaa gctggccgaa   3420

cagtatgcta aagagaacgg cactaagctg ctgctgacca atgaccccct ggaggctgca   3480

cacggaggca acgtcctgat cactgatacc tggatcagca tgggccagga ggaagagaag   3540

aagaagcggc tccaggcctt ccagggctac caggtgacaa tgaaaactgc caaggtcgcc   3600

gcttctgatt ggacttttct gcattgtctg ccccgaaaac ctgaagaggt ggacgatgag   3660

gtcttctatt cacctaggag cctggtgttt ccagaagccg agaatcgcaa gtggacaatc   3720

atggccgtga tggtgtccct gctgactgac tattccccac agctgcagaa gcctaagttt   3780

tgagatatcg tcgactcgct gatcagcctc gactgtgcct tctagttgcc agccatctgt   3840

tgtttgcccc tcccccgtgc cttccttgac cctggaaggt gccactccca ctgtcctttc   3900

ctaataaaat gaggaaattg catcgcattg tctgagtagg tgtcattcta ttctgggggg   3960

tggggtgggg caggacagca agggggagga ttgggaagac aatagcaggc atgctgggga   4020

tgcggtgggc tctatggctt ctgaggcgga aagaaccagc tggggctcga ctagactagt   4080

cctgcaggta gagcatggct acgtaaggaa cccctagtga tggagttggc cactccctct   4140

ctgcgcgctc gctcgctcac tgaggccggg cgaccaaagg tcgcccgacg cccgggcttt   4200

gcccgggcgg cctcagtgag cgagcgagcg cgcagagagg gagtggccaa               4250
```

<210> SEQ ID NO 17
<211> LENGTH: 3872
<212> TYPE: DNA
<213> ORGANISM: Artificial sequence
<220> FEATURE:
<223> OTHER INFORMATION: hOTCenh.hAATprom.SV40int.hOTCco.BGHpa
      expression cassette

<400> SEQUENCE: 17

```
ttagggctga ttgttgagac actggtgaac tttgaacctc tgtgatttcc ctgtttgctc     60
```

```
tgtgcctgat agctttcagt ctgctaacaa atctccttta tgcagtttaa cctctgtact    120
tccaatgggg aggaattgga atcagcctat gggagaagag atagctctag gattcagatc    180
tcccagtctt gtgtctgccg ggcaatgagc aaggctcctt cctgtccaag ctccccgccc    240
ctccccagcc tactgcctcc acccgaagtc tacttcctgg gtgggcagga actgggcact    300
gtgcccaggg catgcactgc ctccacgcag caaccctcag agtcctgagc tgaaccaaga    360
aggaggaggg ggtcgggcct ccgaggaagg cctagccgct gctgctgcca ggaattccag    420
gttggagggg cggcaacctc ctgccagcct tcaggccact ctcctgtgcc tgccagaaga    480
gacagagctt gaggagagct tgaggagagc aggaaaggtg ggacattgct gctgctgctc    540
actcagttcc acaggtggga gggacagcag ggcttagagt gggggtcatt gtgcagatgg    600
gaaaacaaag gcccagagag gggaagaaat gcccaggagc taccgagggc aggcgacctc    660
aaccacagcc cagtgctgga gctgtgagtg gatgtagagc agcggaatat ccattcagcc    720
agctcagggg aaggacaggg gccctgaagc caggggatgg agctgcaggg aagggagctc    780
agagagaagg ggaggggagt ctgagctcag tttcccgctg cctgaaagga gggtggtacc    840
tactcccttc acagggtaac tgaatgagag actgcctgga ggaaagctct tcaagtgtgg    900
cccaccccac cccagtgaca ccagcccctg acacggggga gggagggcag catcaggagg    960
ggctttctgg gcacacccag tacccgtctc tgagctttcc ttgaactgtt gcattttaat   1020
cctcacagca gctcaacaag gtacataccg tcaccatccc cattttacag atagggaaat   1080
tgaggctcgg agcggttaaa caactcacct gaggcctcac agccagtaag tgggttccct   1140
ggtctgaatg tgtgtgctgg aggatcctgt gggtcactcg cctggtagag ccccaaggtg   1200
gaggcataaa tgggactggt gaatgacaga aggggcaaaa atgcactcat ccattcactc   1260
tgcaagtatc tacggcacgt acgccagctc ccaagcaggt ttgcgggttg cacagcgggc   1320
gatgcaatct gatttaggct tttaaaggga ttgcaatcaa gtggggcccc actagcctca   1380
accctgtacc tcccctcccc tccaccccca gcagtctcca aaggcctcca acaaccccag   1440
agtgggggcc atgtatccaa agaaactcca agctgtatac ggatcacact ggttttccag   1500
gagcaaaaac agaaacaggc ctgaggctgg tcaaaattga acctcctcct gctctgagca   1560
gcctgggggg cagactaagc agagggctgt gcagacccac ataaagagcc tactgtgtgc   1620
caggcacttc acccgaggca cttcacaagc atgcttggga atgaaacttc caactctttg   1680
ggatgcaggt gaaacagttc ctggttcaga gaggtgaagc ggcctgcctg aggcagcaca   1740
gctcttcttt acagatgtgc ttccccacct ctaccctgtc tcacggcccc ccatgccagc   1800
ctgacggttg tgtctgcctc agtcatgctc catttttcca tcgggaccat caagagggtg   1860
tttgtgtcta aggctgactg ggtaactttg gatgagcggt ctctccgctc tgagcctgtt   1920
tcctcatctg tcaaatgggc tctaacccac tctgatctcc cagggcggca gtaagtcttc   1980
agcatcaggc attttggggt gactcagtaa atggtagatc ttgctaccag tggaacagcc   2040
actaaggatt ctgcagtgag agcagagggc cagctaagtg gtactctccc agagactgtc   2100
tgactcacgc caccccctcc accttggaca caggacgctg tggtttctga gccaggtaca   2160
atgactcctt tcggtaagtg cagtggaagc tgtacactgc ccaggcaaag cgtccgggca   2220
gcgtaggcgg gcgactcaga tcccagccag tggacttagc ccctgtttgc tcctccgata   2280
actggggtga ccttggttaa tattcaccag cagcctcccc cgttgcccct ctggatccac   2340
tgcttaaata cggacgagga cagggccctg tctcctcagc ttcaggcacc accactgacc   2400
```

```
tgggacagtg aatgcggccg ctctaaggta aatataaaat ttttaagtgt ataatgtgtt   2460

aaactactga ttctaattgt ttctctcttt tagattccaa cctttggaac tgatctagag   2520

aattcgccgc caccatgctg tttaacctga gaatcctgct gaataacgct gcctttagga   2580

acggacataa cttcatggtc cgcaactttc gctgtggcca gcctctccag aacaaagtgc   2640

agctgaaggg gagggacctg ctgaccctga aaaatttcac aggagaggaa atcaagtaca   2700

tgctgtggct gtctgccgat ctgaagttcc ggatcaagca gaagggcgaa tatctgccac   2760

tgctccaggg caaaagtctg ggatgatct tcgaaaagag gagtactcgg accagactgt   2820

caacagagac tggattcgct ctgctgggag gacacccatg ctttctgacc acacaggaca   2880

ttcatctggg cgtgaacgag tcactgaccg acacagcccg ggtgctgagc agcatggccg   2940

atgccgtgct ggcacgggtc tacaaacaga gcgacctgga taccctggct aaggaagcaa   3000

gcatccccat cattaatggg ctgtccgacc tgtatcaccc tatccagatt ctggccgatt   3060

acctgaccct ccaggagcat tattctagtc tgaaaggcct gacactgagc tggattgggg   3120

acggaaacaa tatcctgcac tccattatga tgtctgccgc taagtttggg atgcacctcc   3180

aggcagccac accaaaaggc tacgaacccg atgccagtgt gactaagctg gccgaacagt   3240

atgctaaaga gaacggcact aagctgctgc tgaccaatga cccccctggag gctgcacacg   3300

gaggcaacgt cctgatcact gatacctgga tcagcatggg ccaggaggaa gagaagaaga   3360

agcggctcca ggccttccag ggctaccagg tgacaatgaa aactgccaag gtcgccgctt   3420

ctgattggac ttttctgcat tgtctgcccc gaaaacctga agaggtggac gatgaggtct   3480

tctattcacc taggagcctg gtgtttccag aagccgagaa tcgcaagtgg acaatcatgg   3540

ccgtgatggt gtccctgctg actgactatt ccccacagct gcagaagcct aagttttgag   3600

atatcgtcga ctcgctgatc agcctcgact gtgccttcta gttgccagcc atctgttgtt   3660

tgcccctccc ccgtgccttc cttgaccctg gaaggtgcca ctcccactgt cctttcctaa   3720

taaaatgagg aaattgcatc gcattgtctg agtaggtgtc attctattct ggggggtggg   3780

gtggggcagg acagcaaggg ggaggattgg gaagacaata gcaggcatgc tggggatgcg   3840

gtgggctcta tggcttctga ggcggaaaga ac                                 3872
```

```
<210> SEQ ID NO 18
<211> LENGTH: 4250
<212> TYPE: DNA
<213> ORGANISM: Artificial sequence
<220> FEATURE:
<223> OTHER INFORMATION: AAV2-hOTCenh.hAATprom.SV40int.hOTCco.BGHpa
      expression cassette

<400> SEQUENCE: 18

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttccttacgt agccatgctc tagcgatcgc ggtaccttaa    180

ttaattaggg ctgattgttg agacactggt gaactttgaa cctctgtgat ttccctgttt    240

gctctgtgcc tgatagcttt cagtctgcta acaaatctcc tttatgcagt ttaacctctg    300

tacttccaat ggggaggaat tggaatcagc ctatgggaga agagatagct ctaggattca    360

gatctcccag tcttgtgtct gccgggcaat gagcaaggct ccttcctgtc caagctcccc    420

gcccctcccc agcctactgc ctccacccga agtctacttc ctgggtgggc aggaactggg    480

cactgtgccc agggcatgca ctgcctccac gcagcaaccc tcagagtcct gagctgaacc    540
```

```
aagaaggagg agggggtcgg gcctccgagg aaggcctagc cgctgctgct gccaggaatt    600
ccaggttgga ggggcggcaa cctcctgcca gccttcaggc cactctcctg tgcctgccag    660
aagagacaga gcttgaggag agcttgagga gagcaggaaa ggtgggacat tgctgctgct    720
gctcactcag ttccacaggt gggagggaca gcagggctta gagtgggggt cattgtgcag    780
atgggaaaac aaaggcccag agaggggaag aaatgcccag gagctaccga gggcaggcga    840
cctcaaccac agcccagtgc tggagctgtg agtggatgta gagcagcgga atatccattc    900
agccagctca ggggaaggac aggggccctg aagccagggg atggagctgc agggaaggga    960
gctcagagag aaggggaggg gagtctgagc tcagtttccc gctgcctgaa aggagggtgg   1020
tacctactcc cttcacaggg taactgaatg agagactgcc tggaggaaag ctcttcaagt   1080
gtggcccacc ccaccccagt gacaccagcc cctgacacgg gggagggagg gcagcatcag   1140
gaggggcttt ctgggcacac ccagtacccg tctctgagct ttccttgaac tgttgcattt   1200
taatcctcac agcagctcaa caaggtacat accgtcacca tccccatttt acagataggg   1260
aaattgaggc tcggagcggt taaacaactc acctgaggcc tcacagccag taagtgggtt   1320
ccctggtctg aatgtgtgtg ctggaggatc ctgtgggtca ctcgcctggt agagccccaa   1380
ggtggaggca taaatgggac tggtgaatga cagaaggggc aaaaatgcac tcatccattc   1440
actctgcaag tatctacggc acgtacgcca gctcccaagc aggtttgcgg gttgcacagc   1500
gggcgatgca atctgattta ggcttttaaa gggattgcaa tcaagtgggg ccccactagc   1560
ctcaaccctg tacctcccct cccctccacc cccagcagtc tccaaaggcc tccaacaacc   1620
ccagagtggg ggccatgtat ccaaagaaac tccaagctgt atacggatca cactggtttt   1680
ccaggagcaa aaacagaaac aggcctgagg ctggtcaaaa ttgaacctcc tcctgctctg   1740
agcagcctgg ggggcagact aagcagaggg ctgtgcagac ccacataaag agcctactgt   1800
gtgccaggca cttcacccga ggcacttcac aagcatgctt gggaatgaaa cttccaactc   1860
tttgggatgc aggtgaaaca gttcctggtt cagagaggtg aagcggcctg cctgaggcag   1920
cacagctctt ctttacagat gtgcttcccc acctctaccc tgtctcacgg ccccccatgc   1980
cagcctgacg gttgtgtctg cctcagtcat gctccatttt tccatcggga ccatcaagag   2040
ggtgtttgtg tctaaggctg actgggtaac tttggatgag cggtctctcc gctctgagcc   2100
tgtttcctca tctgtcaaat gggctctaac ccactctgat ctcccagggc ggcagtaagt   2160
cttcagcatc aggcattttg gggtgactca gtaaatggta gatcttgcta ccagtggaac   2220
agccactaag gattctgcag tgagagcaga gggccagcta agtggtactc tcccagagac   2280
tgtctgactc acgccacccc ctccaccttg gacacaggac gctgtggttt ctgagccagg   2340
tacaatgact cctttcggta agtgcagtgg aagctgtaca ctgcccaggc aaagcgtccg   2400
ggcagcgtag gcgggcgact cagatcccag ccagtggact tagcccctgt ttgctcctcc   2460
gataactggg gtgaccttgg ttaatattca ccagcagcct cccccgttgc cctctggat   2520
ccactgctta aatacggacg aggacagggc cctgtctcct cagcttcagg caccaccact   2580
gacctgggac agtgaatgcg gccgctctaa ggtaaatata aaatttttaa gtgtataatg   2640
tgttaaacta ctgattctaa ttgtttctct cttttagatt ccaacctttg gaactgatct   2700
agagaattcg ccgccaccat gctgtttaac ctgagaatcc tgctgaataa cgctgccttt   2760
aggaacggac ataacttcat ggtccgcaac tttcgctgtg gccagcctct ccagaacaaa   2820
gtgcagctga aggggaggga cctgctgacc ctgaaaaatt tcacaggaga ggaaatcaag   2880
tacatgctgt ggctgtctgc cgatctgaag ttccggatca agcagaaggg cgaatatctg   2940
```

ccactgctcc agggcaaaag tctggggatg atcttcgaaa agaggagtac tcggaccaga 3000
ctgtcaacag agactggatt cgctctgctg ggaggacacc catgctttct gaccacacag 3060
gacattcatc tgggcgtgaa cgagtcactg accgacacag cccgggtgct gagcagcatg 3120
gccgatgccg tgctggcacg ggtctacaaa cagagcgacc tggataccct ggctaaggaa 3180
gcaagcatcc ccatcattaa tggctgtcc gacctgtatc accctatcca gattctggcc 3240
gattacctga ccctccagga gcattattct agtctgaaag gcctgacact gagctggatt 3300
ggggacggaa acaatatcct gcactccatt atgatgtctg ccgctaagtt tgggatgcac 3360
ctccaggcag ccacaccaaa aggctacgaa cccgatgcca gtgtgactaa gctggccgaa 3420
cagtatgcta aagagaacgg cactaagctg ctgctgacca atgacccct ggaggctgca 3480 cacggaggca acgtcctgat cactgatacc tggatcagca tgggccagga ggaagagaag 3540
aagaagcggc tccaggcctt ccagggctac caggtgacaa tgaaaactgc caaggtcgcc 3600
gcttctgatt ggacttttct gcattgtctg ccccgaaaac ctgaagaggt ggacgatgag 3660
gtcttctatt cacctaggag cctggtgttt ccagaagccg agaatcgcaa gtggacaatc 3720
atggccgtga tggtgtccct gctgactgac tattccccac agctgcagaa gcctaagttt 3780
tgagatatcg tcgactcgct gatcagcctc gactgtgcct tctagttgcc agccatctgt 3840
tgtttgcccc tcccccgtgc cttccttgac cctggaaggt gccactccca ctgtcctttc 3900
ctaataaaat gaggaaattg catcgcattg tctgagtagg tgtcattcta ttctgggggg 3960
tggggtgggg caggacagca agggggagga ttgggaagac aatagcaggc atgctgggga 4020
tgcggtgggc tctatggctt ctgaggcgga aagaaccagc tggggctcga ctagactagt 4080
cctgcaggta gagcatggct acgtaaggaa cccctagtga tggagttggc cactccctct 4140
ctgcgcgctc gctcgctcac tgaggccggg cgaccaaagg tcgcccgacg cccgggcttt 4200
gcccgggcgg cctcagtgag cgagcgagcg cgcagagagg gagtggccaa 4250

<210> SEQ ID NO 19
<211> LENGTH: 2604
<212> TYPE: DNA
<213> ORGANISM: Artificial sequence
<220> FEATURE:
<223> OTHER INFORMATION: 2hOTCenh.hOTCprom.SV40int.hOTCco.BGHpa
      expression cassette

<400> SEQUENCE: 19
ttagggctga ttgttgagac actggtgaac tttgaacctc tgtgatttcc ctgtttgctc 60
tgtgcctgat agctttcagt ctgctaacaa atctccttta tgcagtttaa cctctgtact 120
tccaatgggg aggaattgga atcagcctat gggagaagag atagctctag gattcttagg 180
gctgattgtt gagacactgg tgaactttga acctctgtga tttccctgtt tgctctgtgc 240
ctgatagctt tcagtctgct aacaaatctc ctttatgcag tttaacctct gtacttccaa 300
tggggaggaa ttggaatcag cctatgggag aagagatagc tctaggattc agatctcaag 360
cgactctcat gcctcagcct cccaaatagc tgggattaca ggtgtgcacc accacgtcta 420
gctaattttt gtatttttag tggagacggg gattcatcat gttggccagg ctggtctcga 480
actcctgggc tcaagtgatc cgcccgcctc agcctcccaa agtgctggga ttataggcgt 540
gagccaccat gcccggccag caattatttc tttattgaag acttatgtgc aaggcacaaa 600
gggagctcca ggactgagat atttttacta taccttctct atcatcttgc acccccaaaa 660
tagcttccag ggcacttcta tttgtttttg tggaaagact ggcaattaga ggtagaaaag 720

```
tgaaataaat ggaaatagta ctactcaggg ctgtcacatc tacatctgtg tttttgcagt    780

gccaatttgc attttctgag tgagttactt ctactcacct tcacagcagc cagtaccgca    840

gtgccttgca tatattatat cctcaatgag tacttgtcaa ttgattttgt acatgcgtgt    900

gacagtataa atatattatg aaaaatgagg aggccaggca ataaaagagt caggatttct    960

tccaaaaaaa atacacagcg gtggagcttg gcataaagtt caaatgctcc tacaccctgc   1020

cctgcagtat ctctaaccag gggactttga taaggaagct gaagggtgat attacctttg   1080

ctccctcact gcaactgaac acatttctta gtttttaggt ggcccccgct ggctaacttg   1140

ctgtggcggc cgctctaagg taaatataaa atttttaagt gtataatgtg ttaaactact   1200

gattctaatt gtttctctct tttagattcc aacctttgga actgatctag agaattcgcc   1260

gccaccatgc tgtttaacct gagaatcctg ctgaataacg ctgcctttag gaacggacat   1320

aacttcatgg tccgcaactt tcgctgtggc cagcctctcc agaacaaagt gcagctgaag   1380

gggagggacc tgctgaccct gaaaaatttc acaggagagg aaatcaagta catgctgtgg   1440

ctgtctgccg atctgaagtt ccggatcaag cagaagggcg aatatctgcc actgctccag   1500

ggcaaaagtc tggggatgat cttcgaaaag aggagtactc ggaccagact gtcaacagag   1560

actggattcg ctctgctggg aggacaccca tgctttctga ccacacagga cattcatctg   1620

ggcgtgaacg agtcactgac cgacacagcc cgggtgctga gcagcatggc cgatgccgtg   1680

ctggcacggg tctacaaaca gagcgacctg gataccctgg ctaaggaagc aagcatcccc   1740

atcattaatg ggctgtccga cctgtatcac cctatccaga ttctggccga ttacctgacc   1800

ctccaggagc attattctag tctgaaaggc ctgacactga gctggattgg ggacggaaac   1860

aatatcctgc actccattat gatgtctgcc gctaagtttg ggatgcacct ccaggcagcc   1920

acaccaaaag gctacgaacc cgatgccagt gtgactaagc tggccgaaca gtatgctaaa   1980

gagaacggca ctaagctgct gctgaccaat gacccccctgg aggctgcaca cggaggcaac   2040

gtcctgatca ctgatacctg gatcagcatg ggccaggagg aagagaagaa gaagcggctc   2100

caggccttcc agggctacca ggtgacaatg aaaactgcca aggtcgccgc ttctgattgg   2160

acttttctgc attgtctgcc ccgaaaacct gaagaggtgg acgatgaggt cttctattca   2220

cctaggagcc tggtgtttcc agaagccgag aatcgcaagt ggacaatcat ggccgtgatg   2280

gtgtccctgc tgactgacta ttccccacag ctgcagaagc ctaagttttg agatatcgtc   2340

gactcgctga tcagcctcga ctgtgccttc tagttgccag ccatctgttg tttgcccctc   2400

ccccgtgcct tccttgaccc tggaaggtgc cactcccact gtcctttcct aataaaatga   2460

ggaaattgca tcgcattgtc tgagtaggtg tcattctatt ctggggggtg gggtggggca   2520

ggacagcaag ggggaggatt gggaagacaa tagcaggcat gctggggatg cggtgggctc   2580

tatggcttct gaggcggaaa gaac                                          2604
```

<210> SEQ ID NO 20
<211> LENGTH: 2982
<212> TYPE: DNA
<213> ORGANISM: Artificial sequence
<220> FEATURE:
<223> OTHER INFORMATION: AAV2-2hOTCenh.hOTCprom.SV40int.hOTCco.BGHpa expression cassette

<400> SEQUENCE: 20

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120
```

```
gccaactcca tcactagggg ttccttacgt agccatgctc tagcgatcgc ggtaccttaa    180
ttaattaggg ctgattgttg agacactggt gaactttgaa cctctgtgat ttccctgttt    240
gctctgtgcc tgatagcttt cagtctgcta acaaatctcc tttatgcagt ttaacctctg    300
tacttccaat ggggaggaat tggaatcagc ctatgggaga agagatagct ctaggattct    360
tagggctgat tgttgagaca ctggtgaact ttgaacctct gtgatttccc tgtttgctct    420
gtgcctgata gctttcagtc tgctaacaaa tctcctttat gcagtttaac ctctgtactt    480
ccaatgggga ggaattggaa tcagcctatg ggagaagaga tagctctagg attcagatct    540
caagcgactc tcatgcctca gcctcccaaa tagctgggat tacaggtgtg caccaccacg    600
tctagctaat ttttgtattt ttagtggaga cggggattca tcatgttggc caggctggtc    660
tcgaactcct gggctcaagt gatccgcccg cctcagcctc ccaaagtgct gggattatag    720
gcgtgagcca ccatgcccgg ccagcaatta tttctttatt gaagacttat gtgcaaggca    780
caaagggagc tccaggactg agatattttt actatacctt ctctatcatc ttgcaccccc    840
aaaatagctt ccagggcact tctatttgtt tttgtggaaa gactggcaat tagaggtaga    900
aaagtgaaat aaatggaaat agtactactc agggctgtca catctacatc tgtgtttttg    960
cagtgccaat ttgcattttc tgagtgagtt acttctactc accttcacag cagccagtac   1020
cgcagtgcct tgcatatatt atatcctcaa tgagtacttg tcaattgatt ttgtacatgc   1080
gtgtgacagt ataaatatat tatgaaaaat gaggaggcca ggcaataaaa gagtcaggat   1140
ttcttccaaa aaaaatacac agcggtggag cttggcataa agttcaaatg ctcctacacc   1200
ctgccctgca gtatctctaa ccaggggact ttgataagga agctgaaggg tgatattacc   1260
tttgctccct cactgcaact gaacacattt cttagttttt aggtggcccc cgctggctaa   1320
cttgctgtgg cggccgctct aaggtaaata taaaattttt aagtgtataa tgtgttaaac   1380
tactgattct aattgtttct ctcttttaga ttccaacctt tggaactgat ctagagaatt   1440
cgccgccacc atgctgttta acctgagaat cctgctgaat aacgctgcct ttaggaacgg   1500
acataacttc atggtccgca actttcgctg tggccagcct ctccagaaca aagtgcagct   1560
gaaggggagg gacctgctga ccctgaaaaa tttcacagga gaggaaatca agtacatgct   1620
gtggctgtct gccgatctga agttccggat caagcagaag ggcgaatatc tgccactgct   1680
ccagggcaaa agtctgggga tgatcttcga aaagaggagt actcggacca gactgtcaac   1740
agagactgga ttcgctctgc tgggaggaca cccatgcttt ctgaccacac aggacattca   1800
tctgggcgtg aacgagtcac tgaccgacac agcccgggtg ctgagcagca tggccgatgc   1860
cgtgctggca cgggtctaca aacagagcga cctggatacc ctggctaagg aagcaagcat   1920
ccccatcatt aatgggctgt ccgacctgta tcaccctatc cagattctgg ccgattacct   1980
gaccctccag gagcattatt ctagtctgaa aggcctgaca ctgagctgga ttggggacgg   2040
aaacaatatc ctgcactcca ttatgatgtc tgccgctaag tttgggatgc acctccaggc   2100
agccacacca aaaggctacg aacccgatgc cagtgtgact aagctggccg aacagtatgc   2160
taaagagaac ggcactaagc tgctgctgac caatgacccc ctggaggctg cacacggagg   2220
caacgtcctg atcactgata cctggatcag catgggccag gaggaagaga agaagaagcg   2280
gctccaggcc ttccagggct accaggtgac aatgaaaact gccaaggtcg ccgcttctga   2340
ttggactttt ctgcattgtc tgccccgaaa acctgaagag gtggacgatg aggtcttcta   2400
ttcacctagg agcctggtgt ttccagaagc cgagaatcgc aagtggacaa tcatggccgt   2460
```

```
gatggtgtcc ctgctgactg actattcccc acagctgcag aagcctaagt tttgagatat   2520
cgtcgactcg ctgatcagcc tcgactgtgc cttctagttg ccagccatct gttgtttgcc   2580
cctcccccgt gccttccttg accctggaag gtgccactcc cactgtcctt tcctaataaa   2640
atgaggaaat tgcatcgcat tgtctgagta ggtgtcattc tattctgggg ggtggggtgg   2700
ggcaggacag caagggggag gattgggaag acaatagcag gcatgctggg gatgcggtgg   2760
gctctatggc ttctgaggcg gaaagaacca gctggggctc gactagacta gtcctgcagg   2820
tagagcatgg ctacgtaagg aacccctagt gatggagttg gccactccct ctctgcgcgc   2880
tcgctcgctc actgaggccg ggcgaccaaa ggtcgcccga cgcccgggct ttgcccgggc   2940
ggcctcagtg agcgagcgag cgcgcagaga gggagtggcc aa                      2982
```

```
<210> SEQ ID NO 21
<211> LENGTH: 3050
<212> TYPE: DNA
<213> ORGANISM: Artificial sequence
<220> FEATURE:
<223> OTHER INFORMATION: 2hOTCenh.hOTCprom.betagint.hOTCco.BGHpa
      expression cassette

<400> SEQUENCE: 21

ttagggctga ttgttgagac actggtgaac tttgaacctc tgtgatttcc ctgtttgctc     60
tgtgcctgat agctttcagt ctgctaacaa atctccttta tgcagtttaa cctctgtact    120
tccaatgggg aggaattgga atcagcctat gggagaagag atagctctag gattcttagg    180
gctgattgtt gagacactgg tgaactttga acctctgtga tttccctgtt tgctctgtgc    240
ctgatagctt tcagtctgct aacaaatctc ctttatgcag tttaacctct gtacttccaa    300
tggggaggaa ttggaatcag cctatgggag aagagatagc tctaggattc agatctcaag    360
cgactctcat gcctcagcct cccaaatagc tgggattaca ggtgtgcacc accacgtcta    420
gctaattttt gtatttttag tggagacggg gattcatcat gttggccagg ctggtctcga    480
actcctgggc tcaagtgatc cgcccgcctc agcctcccaa agtgctggga ttataggcgt    540
gagccaccat gcccggccag caattatttc tttattgaag acttatgtgc aaggcacaaa    600
gggagctcca ggactgagat atttttacta taccttctct atcatcttgc acccccaaaa    660
tagcttccag ggcacttcta tttgtttttg tggaaagact ggcaattaga ggtagaaaag    720
tgaaataaat ggaaatagta ctactcaggg ctgtcacatc tacatctgtg tttttgcagt    780
gccaatttgc attttctgag tgagttactt ctactcacct tcacagcagc cagtaccgca    840
gtgccttgca tatattatat cctcaatgag tacttgtcaa ttgattttgt acatgcgtgt    900
gacagtataa atatattatg aaaaatgagg aggccaggca ataaaagagt caggatttct    960
tccaaaaaaa atacacagcg gtggagcttg gcataaagtt caaatgctcc tacaccctgc   1020
cctgcagtat ctctaaccag ggactttga taaggaagct gaagggtgat attacctttg   1080
ctccctcact gcaactgaac acatttctta gtttttaggt ggcccccgct ggctaacttg   1140
ctgtggcggc cgctgagaac ttcagggtga gtctatggga cccttgatgt tttctttccc   1200
cttcttttct atggttaagt tcatgtcata ggaaggggag aagtaacagg gtacacatat   1260
tgaccaaatc agggtaattt tgcatttgta attttaaaaa atgctttctt cttttaatat   1320
actttttgt ttatcttatt tctaatactt tccctaatct ctttctttca gggcaataat   1380
gatacaatgt atcatgcctc tttgcaccat tctaaagaat aacagtgata atttctgggt   1440
taaggcaata gcaatatttc tgcatataaa tatttctgca tataaattgt aactgatgta   1500
```

```
agaggtttca tattgctaat agcagctaca atccagctac cattctgctt ttattttatg   1560

gttgggataa ggctggatta ttctgagtcc aagctaggcc cttttgctaa tcatgttcat   1620

acctcttatc ttcctcccac agctcctggg caacgtgctg gtctgtgtgc tggcccatca   1680

ctttggcaaa gcacgtggaa ttcgccgcca ccatgctgtt taacctgaga atcctgctga   1740

ataacgctgc ctttaggaac ggacataact tcatggtccg caactttcgc tgtggccagc   1800

ctctccagaa caaagtgcag ctgaagggga gggacctgct gaccctgaaa aatttcacag   1860

gagaggaaat caagtacatg ctgtggctgt ctgccgatct gaagttccgg atcaagcaga   1920

agggcgaata tctgccactg ctccagggca aaagtctggg gatgatcttc gaaaagagga   1980

gtactcggac cagactgtca acagagactg gattcgctct gctgggagga cacccatgct   2040

ttctgaccac acaggacatt catctgggcg tgaacgagtc actgaccgac acagcccggg   2100

tgctgagcag catggccgat gccgtgctgg cacgggtcta caaacagagc gacctggata   2160

ccctggctaa ggaagcaagc atccccatca ttaatgggct gtccgacctg tatcacccta   2220

tccagattct ggccgattac ctgaccctcc aggagcatta ttctagtctg aaaggcctga   2280

cactgagctg gattggggac ggaaacaata tcctgcactc cattatgatg tctgccgcta   2340

agtttgggat gcacctccag gcagccacac caaaaggcta cgaacccgat gccagtgtga   2400

ctaagctggc cgaacagtat gctaaagaga acggcactaa gctgctgctg accaatgacc   2460

ccctggaggc tgcacacgga ggcaacgtcc tgatcactga tacctggatc agcatgggcc   2520

aggaggaaga gaagaagaag cggctccagg ccttccaggg ctaccaggtg acaatgaaaa   2580

ctgccaaggt cgccgcttct gattggactt ttctgcattg tctgccccga aaacctgaag   2640

aggtggacga tgaggtcttc tattcaccta ggagcctggt gtttccagaa gccgagaatc   2700

gcaagtggac aatcatggcc gtgatggtgt ccctgctgac tgactattcc ccacagctgc   2760

agaagcctaa gttttgagat atcgtcgact cgctgatcag cctcgactgt gccttctagt   2820

tgccagccat ctgttgtttg cccctccccc gtgccttcct tgaccctgga aggtgccact   2880

cccactgtcc tttcctaata aaatgaggaa attgcatcgc attgtctgag taggtgtcat   2940

tctattctgg ggggtggggt ggggcaggac agcaaggggg aggattggga agacaatagc   3000

aggcatgctg gggatgcggt gggctctatg gcttctgagg cggaaagaac             3050
```

<210> SEQ ID NO 22
<211> LENGTH: 3428
<212> TYPE: DNA
<213> ORGANISM: Artificial sequence
<220> FEATURE:
<223> OTHER INFORMATION: AAV2-2hOTCenh.hOTCprom.beta gint.hOTCco.BGHpa expression cassette

<400> SEQUENCE: 22

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttccttacgt agccatgctc tagcgatcgc ggtaccttaa    180

ttaattaggg ctgattgttg agacactggt gaactttgaa cctctgtgat ttccctgttt    240

gctctgtgcc tgatagcttt cagtctgcta acaaatctcc tttatgcagt ttaacctctg    300

tacttccaat ggggaggaat tggaatcagc ctatgggaga agagatagct ctaggattct    360

tagggctgat tgttgagaca ctggtgaact ttgaacctct gtgatttccc tgtttgctct    420

gtgcctgata gctttcagtc tgctaacaaa tctcctttat gcagtttaac ctctgtactt    480
```

```
ccaatgggga ggaattggaa tcagcctatg ggagaagaga tagctctagg attcagatct    540
caagcgactc tcatgcctca gcctcccaaa tagctgggat tacaggtgtg caccaccacg    600
tctagctaat ttttgtattt ttagtggaga cggggattca tcatgttggc caggctggtc    660
tcgaactcct gggctcaagt gatccgcccg cctcagcctc ccaaagtgct gggattatag    720
gcgtgagcca ccatgcccgg ccagcaatta tttctttatt gaagacttat gtgcaaggca    780
caaagggagc tccaggactg agatattttt actatacctt ctctatcatc ttgcaccccc    840
aaaatagctt ccagggcact tctatttgtt tttgtggaaa gactggcaat tagaggtaga    900
aaagtgaaat aaatggaaat agtactactc agggctgtca catctacatc tgtgtttttg    960
cagtgccaat ttgcattttc tgagtgagtt acttctactc accttcacag cagccagtac   1020
cgcagtgcct tgcatatatt atatcctcaa tgagtacttg tcaattgatt ttgtacatgc   1080
gtgtgacagt ataaatatat tatgaaaaat gaggaggcca ggcaataaaa gagtcaggat   1140
ttcttccaaa aaaaatacac agcggtggag cttggcataa agttcaaatg ctcctacacc   1200
ctgccctgca gtatctctaa ccaggggact ttgataagga agctgaaggg tgatattacc   1260
tttgctccct cactgcaact gaacacattt cttagttttt aggtggcccc cgctggctaa   1320
cttgctgtgg cggccgctga gaacttcagg gtgagtctat gggacccttg atgttttctt   1380
tccccttctt ttctatggtt aagttcatgt cataggaagg ggagaagtaa cagggtacac   1440
atattgacca aatcagggta attttgcatt tgtaatttta aaaaatgctt tcttctttta   1500
atatactttt ttgtttatct tatttctaat actttcccta atctctttct ttcagggcaa   1560
taatgataca atgtatcatg cctctttgca ccattctaaa gaataacagt gataatttct   1620
gggttaaggc aatagcaata tttctgcata taaatatttc tgcatataaa ttgtaactga   1680
tgtaagaggt ttcatattgc taatagcagc tacaatccag ctaccattct gcttttattt   1740
tatggttggg ataaggctgg attattctga gtccaagcta ggcccttttg ctaatcatgt   1800
tcatacctct tatcttcctc ccacagctcc tgggcaacgt gctggtctgt gtgctggccc   1860
atcactttgg caaagcacgt ggaattcgcc gccaccatgc tgtttaacct gagaatcctg   1920
ctgaataacg ctgcctttag gaacggacat aacttcatgg tccgcaactt tcgctgtggc   1980
cagcctctcc agaacaaagt gcagctgaag ggagagggacc tgctgaccct gaaaaatttc   2040
acaggagagg aaatcaagta catgctgtgg ctgtctgccg atctgaagtt ccggatcaag   2100
cagaagggcg aatatctgcc actgctccag ggcaaaagtc tggggatgat cttcgaaaag   2160
aggagtactc ggaccagact gtcaacagag actggattcg ctctgctggg aggacaccca   2220
tgctttctga ccacacagga cattcatctg ggcgtgaacg agtcactgac cgacacagcc   2280
cgggtgctga gcagcatggc cgatgccgtg ctggcacggg tctacaaaca gagcgacctg   2340
gataccctgg ctaaggaagc aagcatcccc atcattaatg ggctgtccga cctgtatcac   2400
cctatccaga ttctggccga ttacctgacc ctccaggagc attattctag tctgaaaggc   2460
ctgacactga gctggattgg ggacggaaac aatatcctgc actccattat gatgtctgcc   2520
gctaagtttg ggatgcacct ccaggcagcc acaccaaaag gctacgaacc cgatgccagt   2580
gtgactaagc tggccgaaca gtatgctaaa gagaacggca ctaagctgct gctgaccaat   2640
gacccccctgg aggctgcaca cggaggcaac gtcctgatca ctgatacctg gatcagcatg   2700
ggccaggagg aagagaagaa gaagcggctc caggccttcc agggctacca ggtgacaatg   2760
aaaactgcca aggtcgccgc ttctgattgg acttttctgc attgtctgcc ccgaaaacct   2820
gaagaggtgg acgatgaggt cttctattca cctaggagcc tggtgtttcc agaagccgag   2880
```

```
aatcgcaagt ggacaatcat ggccgtgatg gtgtccctgc tgactgacta ttccccacag   2940

ctgcagaagc ctaagttttg agatatcgtc gactcgctga tcagcctcga ctgtgccttc   3000

tagttgccag ccatctgttg tttgcccctc ccccgtgcct tccttgaccc tggaaggtgc   3060

cactcccact gtcctttcct aataaaatga ggaaattgca tcgcattgtc tgagtaggtg   3120

tcattctatt ctggggggtg gggtggggca ggacagcaag ggggaggatt gggaagacaa   3180

tagcaggcat gctggggatg cggtgggctc tatggcttct gaggcggaaa gaaccagctg   3240

gggctcgact agactagtcc tgcaggtaga gcatggctac gtaaggaacc cctagtgatg   3300

gagttggcca ctccctctct gcgcgctcgc tcgctcactg aggccgggcg accaaaggtc   3360

gcccgacgcc cgggctttgc ccgggcggcc tcagtgagcg agcgagcgcg cagagaggga   3420

gtggccaa                                                            3428
```

<210> SEQ ID NO 23
<211> LENGTH: 2207
<212> TYPE: DNA
<213> ORGANISM: Artificial sequence
<220> FEATURE:
<223> OTHER INFORMATION: 2hOTCenh.hAATprom.SV40int.hOTCco.BGHpa expression cassette

<400> SEQUENCE: 23

```
ttagggctga ttgttgagac actggtgaac tttgaacctc tgtgatttcc ctgtttgctc     60

tgtgcctgat agctttcagt ctgctaacaa atctccttta tgcagtttaa cctctgtact    120

tccaatgggg aggaattgga atcagcctat gggagaagag atagctctag gattcttagg    180

gctgattgtt gagacactgg tgaactttga acctctgtga tttccctgtt tgctctgtgc    240

ctgatagctt tcagtctgct aacaaatctc ctttatgcag tttaacctct gtacttccaa    300

tggggaggaa ttggaatcag cctatgggag aagagatagc tctaggattc agatcttgct    360

accagtggaa cagccactaa ggattctgca gtgagagcag agggccagct aagtggtact    420

ctcccagaga ctgtctgact cacgccaccc cctccacctt ggacacagga cgctgtggtt    480

tctgagccag gtacaatgac tcctttcggt aagtgcagtg gaagctgtac actgcccagg    540

caaagcgtcc gggcagcgta ggcgggcgac tcagatccca gccagtggac ttagcccctg    600

tttgctcctc cgataactgg ggtgaccttg gttaatattc accagcagcc tcccccgttg    660

cccctctgga tccactgctt aaatacggac gaggacaggg ccctgtctcc tcagcttcag    720

gcaccaccac tgacctggga cagtgaatgc ggccgctcta aggtaaatat aaaattttta    780

agtgtataat gtgttaaact actgattcta attgtttctc tcttttagat tccaaccttt    840

ggaactgatc tagagaattc gccgccacca tgctgtttaa cctgagaatc ctgctgaata    900

acgctgcctt taggaacgga cataacttca tggtccgcaa ctttcgctgt ggccagcctc    960

tccagaacaa agtgcagctg aaggggaggg acctgctgac cctgaaaaat ttcacaggag   1020

aggaaatcaa gtacatgctg tggctgtctg ccgatctgaa gttccggatc aagcagaagg   1080

gcgaatatct gccactgctc cagggcaaaa gtctggggat gatcttcgaa aagaggagta   1140

ctcggaccag actgtcaaca gagactggat tcgctctgct gggaggacac ccatgctttc   1200

tgaccacaca ggacattcat ctgggcgtga acgagtcact gaccgacaca gcccgggtgc   1260

tgagcagcat ggccgatgcc gtgctggcac gggtctacaa acagagcgac ctggataccc   1320

tggctaagga agcaagcatc cccatcatta atgggctgtc cgacctgtat caccctatcc   1380

agattctggc cgattacctg accctccagg agcattattc tagtctgaaa ggcctgacac   1440
```

```
tgagctggat tggggacgga aacaatatcc tgcactccat tatgatgtct gccgctaagt   1500

ttgggatgca cctccaggca gccacaccaa aaggctacga acccgatgcc agtgtgacta   1560

agctggccga acagtatgct aaagagaacg gcactaagct gctgctgacc aatgaccccc   1620

tggaggctgc acacggaggc aacgtcctga tcactgatac ctggatcagc atgggccagg   1680

aggaagagaa gaagaagcgg ctccaggcct tccagggcta ccaggtgaca atgaaaactg   1740

ccaaggtcgc cgcttctgat tggacttttc tgcattgtct gccccgaaaa cctgaagagg   1800

tggacgatga ggtcttctat tcacctagga gcctggtgtt tccagaagcc gagaatcgca   1860

agtggacaat catggccgtg atggtgtccc tgctgactga ctattcccca cagctgcaga   1920

agcctaagtt ttgagatatc gtcgactcgc tgatcagcct cgactgtgcc ttctagttgc   1980

cagccatctg ttgtttgccc ctcccccgtg ccttccttga ccctggaagg tgccactccc   2040

actgtccttt cctaataaaa tgaggaaatt gcatcgcatt gtctgagtag gtgtcattct   2100

attctggggg gtggggtggg gcaggacagc aagggggagg attgggaaga caatagcagg   2160

catgctgggg atgcggtggg ctctatggct tctgaggcgg aaagaac                 2207
```

```
<210> SEQ ID NO 24
<211> LENGTH: 2585
<212> TYPE: DNA
<213> ORGANISM: Artificial sequence
<220> FEATURE:
<223> OTHER INFORMATION: AAV2-2hOTCenh.hAATprom.SV40int.hOTCco.BGHpa
      expression cassette

<400> SEQUENCE: 24

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttccttacgt agccatgctc tagcgatcgc ggtaccttaa    180

ttaattaggg ctgattgttg agacactggt gaactttgaa cctctgtgat ttccctgttt    240

gctctgtgcc tgatagcttt cagtctgcta acaaatctcc tttatgcagt ttaacctctg    300

tacttccaat ggggaggaat tggaatcagc ctatgggaga agagatagct ctaggattct    360

tagggctgat tgttgagaca ctggtgaact ttgaacctct gtgatttccc tgtttgctct    420

gtgcctgata gctttcagtc tgctaacaaa tctcctttat gcagtttaac ctctgtactt    480

ccaatgggga ggaattggaa tcagcctatg ggagaagaga tagctctagg attcagatct    540

tgctaccagt ggaacagcca ctaaggattc tgcagtgaga gcagagggcc agctaagtgg    600

tactctccca gagactgtct gactcacgcc acccccctcca ccttggacac aggacgctgt    660

ggtttctgag ccaggtacaa tgactccttt cggtaagtgc agtggaagct gtacactgcc    720

caggcaaagc gtccgggcag cgtaggcggg cgactcagat cccagccagt ggacttagcc    780

cctgtttgct cctccgataa ctggggtgac cttggttaat attcaccagc agcctccccc    840

gttgcccctc tggatccact gcttaaatac ggacgaggac agggccctgt ctcctcagct    900

tcaggcacca ccactgacct gggacagtga atgcggccgc tctaaggtaa atataaaatt    960

tttaagtgta taatgtgtta aactactgat tctaattgtt tctctctttt agattccaac   1020

ctttggaact gatctagaga attcgccgcc accatgctgt ttaacctgag aatcctgctg   1080

aataacgctg cctttaggaa cggacataac ttcatggtcc gcaactttcg ctgtggccag   1140

cctctccaga acaaagtgca gctgaagggg agggacctgc tgaccctgaa aaatttcaca   1200

ggagaggaaa tcaagtacat gctgtggctg tctgccgatc tgaagttccg gatcaagcag   1260
```

aagggcgaat atctgccact gctccagggc aaaagtctgg ggatgatctt cgaaaagagg 1320
agtactcgga ccagactgtc aacagagact ggattcgctc tgctgggagg acacccatgc 1380
tttctgacca cacaggacat tcatctgggc gtgaacgagt cactgaccga cacagcccgg 1440
gtgctgagca gcatggccga tgccgtgctg gcacgggtct acaaacagag cgacctggat 1500
accctggcta aggaagcaag catccccatc attaatgggc tgtccgacct gtatcaccct 1560
atccagattc tggccgatta cctgaccctc caggagcatt attctagtct gaaaggcctg 1620
acactgagct ggattgggga cggaaacaat atcctgcact ccattatgat gtctgccgct 1680
aagtttggga tgcacctcca ggcagccaca ccaaaaggct acgaacccga tgccagtgtg 1740
actaagctgg ccgaacagta tgctaaagag aacggcacta agctgctgct gaccaatgac 1800
cccctggagg ctgcacacgg aggcaacgtc ctgatcactg atacctggat cagcatgggc 1860
caggaggaag agaagaagaa gcggctccag gccttccagg gctaccaggt gacaatgaaa 1920
actgccaagg tcgccgcttc tgattggact tttctgcatt gtctgccccg aaaacctgaa 1980
gaggtggacg atgaggtctt ctattcacct aggagcctgg tgtttccaga agccgagaat 2040
cgcaagtgga caatcatggc cgtgatggtg tccctgctga ctgactattc cccacagctg 2100
cagaagccta agttttgaga tatcgtcgac tcgctgatca gcctcgactg tgccttctag 2160
ttgccagcca tctgttgttt gcccctcccc cgtgccttcc ttgaccctgg aaggtgccac 2220
tcccactgtc ctttcctaat aaaatgagga aattgcatcg cattgtctga gtaggtgtca 2280
ttctattctg gggggtgggg tggggcagga cagcaagggg gaggattggg aagacaatag 2340
caggcatgct ggggatgcgg tgggctctat ggcttctgag gcggaaagaa ccagctgggg 2400
ctcgactaga ctagtcctgc aggtagagca tggctacgta aggaacccct agtgatggag 2460
ttggccactc cctctctgcg cgctcgctcg ctcactgagg ccgggcgacc aaaggtcgcc 2520
cgacgcccgg gctttgcccg ggcggcctca gtgagcgagc gagcgcgcag agagggagtg 2580
gccaa 2585

<210> SEQ ID NO 25
<211> LENGTH: 2659
<212> TYPE: DNA
<213> ORGANISM: Artificial sequence
<220> FEATURE:
<223> OTHER INFORMATION: 2hOTCenh.hAATprom.beta gint.hOTCco.BGHpa expression cassette

<400> SEQUENCE: 25
ttagggctga ttgttgagac actggtgaac tttgaacctc tgtgatttcc ctgtttgctc 60
tgtgcctgat agctttcagt ctgctaacaa atctccttta tgcagtttaa cctctgtact 120
tccaatgggg aggaattgga atcagcctat gggagaagag atagctctag gattcttagg 180
gctgattgtt gagacactgg tgaactttga acctctgtga tttccctgtt tgctctgtgc 240
ctgatagctt tcagtctgct aacaaatctc ctttatgcag tttaacctct gtacttccaa 300
tggggaggaa ttggaatcag cctatgggag aagagatagc tctaggattc agatcttgct 360
accagtggaa cagccactaa ggattctgca gtgagagcag agggccagct aagtggtact 420
ctcccagaga ctgtctgact cacgccaccc cctccacctt ggacacagga cgctgtggtt 480
tctgagccag gtacaatgac tcctttcggt aagtgcagtg gaagctgtac actgcccagg 540
caaagcgtcc gggcagcgta ggcgggcgac tcagatccca gccagtggac ttagcccctg 600
tttgctcctc cgataactgg ggtgaccttg gttaatattc accagcagcc tcccccgttg 660

```
cccctctgga tccactgctt aaatacggac gaggacaggg ccctgtctcc tcagcttcag    720
gcaccaccac tgacctggga cagtgaatgc ggccgctgag aacttcaggg tgagtctatg    780
ggacccttga tgttttcttt ccccttcttt tctatggtta agttcatgtc ataggaaggg    840
gagaagtaac agggtacaca tattgaccaa atcagggtaa ttttgcattt gtaattttaa    900
aaaatgcttt cttcttttaa tatacttttt tgtttatctt atttctaata ctttccctaa    960
tctctttctt tcagggcaat aatgatacaa tgtatcatgc ctctttgcac cattctaaag   1020
aataacagtg ataatttctg ggttaaggca atagcaatat ttctgcatat aaatatttct   1080
gcatataaat tgtaactgat gtaagaggtt tcatattgct aatagcagct acaatccagc   1140
taccattctg cttttatttt atggttggga taaggctgga ttattctgag tccaagctag   1200
gcccttttgc taatcatgtt catacctctt atcttcctcc cacagctcct gggcaacgtg   1260
ctggtctgtg tgctggccca tcactttggc aaagcacgtg agatctgaat tcgccgccac   1320
catgctgttt aacctgagaa tcctgctgaa taacgctgcc tttaggaacg gacataactt   1380
catggtccgc aactttcgct gtggccagcc tctccagaac aaagtgcagc tgaaggggag   1440
ggacctgctg accctgaaaa atttcacagg agaggaaatc aagtacatgc tgtggctgtc   1500
tgccgatctg aagttccgga tcaagcagaa gggcgaatat ctgccactgc tccagggcaa   1560
aagtctgggg atgatcttcg aaaagaggag tactcggacc agactgtcaa cagagactgg   1620
attcgctctg ctgggaggac acccatgctt tctgaccaca caggacattc atctgggcgt   1680
gaacgagtca ctgaccgaca cagcccgggt gctgagcagc atggccgatg ccgtgctggc   1740
acgggtctac aaacagagcg acctggatac cctggctaag gaagcaagca tccccatcat   1800
taatgggctg tccgacctgt atcaccctat ccagattctg gccgattacc tgaccctcca   1860
ggagcattat tctagtctga aaggcctgac actgagctgg attggggacg gaaacaatat   1920
cctgcactcc attatgatgt ctgccgctaa gtttgggatg cacctccagg cagccacacc   1980
aaaaggctac gaacccgatg ccagtgtgac taagctggcc gaacagtatg ctaaagagaa   2040
cggcactaag ctgctgctga ccaatgaccc cctggaggct gcacacggag gcaacgtcct   2100
gatcactgat acctggatca gcatgggcca ggaggaagag aagaagaagc ggctccaggc   2160
cttccagggc taccaggtga caatgaaaac tgccaaggtc gccgcttctg attggacttt   2220
tctgcattgt ctgccccgaa aacctgaaga ggtggacgat gaggtcttct attcacctag   2280
gagcctggtg tttccagaag ccgagaatcg caagtggaca atcatggccg tgatggtgtc   2340
cctgctgact gactattccc cacagctgca gaagcctaag ttttgagata tcgtcgactc   2400
gctgatcagc ctcgactgtg ccttctagtt gccagccatc tgttgtttgc ccctcccccg   2460
tgccttcctt gaccctggaa ggtgccactc ccactgtcct ttcctaataa aatgaggaaa   2520
ttgcatcgca ttgtctgagt aggtgtcatt ctattctggg gggtggggtg gggcaggaca   2580
gcaaggggga ggattgggaa gacaatagca ggcatgctgg ggatgcggtg ggctctatgg   2640
cttctgaggc ggaaagaac                                                2659
```

<210> SEQ ID NO 26
<211> LENGTH: 3037
<212> TYPE: DNA
<213> ORGANISM: Artificial sequence
<220> FEATURE:
<223> OTHER INFORMATION: AAV2-2hOTCenh.hAATprom.beta gint.hOTCco.BGHpa expression cassette

<400> SEQUENCE: 26

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttccttacgt agccatgctc tagcgatcgc ggtaccttaa    180
ttaattaggg ctgattgttg agacactggt gaactttgaa cctctgtgat ttccctgttt    240
gctctgtgcc tgatagcttt cagtctgcta acaaatctcc tttatgcagt ttaacctctg    300
tacttccaat ggggaggaat tggaatcagc ctatgggaga agagatagct ctaggattct    360
tagggctgat tgttgagaca ctggtgaact ttgaacctct gtgatttccc tgtttgctct    420
gtgcctgata gctttcagtc tgctaacaaa tctcctttat gcagtttaac ctctgtactt    480
ccaatgggga ggaattggaa tcagcctatg ggagaagaga tagctctagg attcagatct    540
tgctaccagt ggaacagcca ctaaggattc tgcagtgaga gcagagggcc agctaagtgg    600
tactctccca gagactgtct gactcacgcc accccctcca ccttggacac aggacgctgt    660
ggtttctgag ccaggtacaa tgactccttt cggtaagtgc agtggaagct gtacactgcc    720
caggcaaagc gtccgggcag cgtaggcggg cgactcagat cccagccagt ggacttagcc    780
cctgtttgct cctccgataa ctggggtgac cttggttaat attcaccagc agcctccccc    840
gttgcccctc tggatccact gcttaaatac ggacgaggac agggccctgt ctcctcagct    900
tcaggcacca ccactgacct gggacagtga atgcggccgc tgagaacttc agggtgagtc    960
tatgggaccc ttgatgtttt ctttcccctt cttttctatg gttaagttca tgtcatagga   1020
aggggagaag taacagggta cacatattga ccaaatcagg gtaattttgc atttgtaatt   1080
ttaaaaaatg ctttcttctt ttaatatact tttttgttta tcttatttct aatactttcc   1140
ctaatctctt tctttcaggg caataatgat acaatgtatc atgcctcttt gcaccattct   1200
aaagaataac agtgataatt tctgggttaa ggcaatagca atatttctgc atataaatat   1260
ttctgcatat aaattgtaac tgatgtaaga ggtttcatat tgctaatagc agctacaatc   1320
cagctaccat tctgctttta ttttatggtt gggataaggc tggattattc tgagtccaag   1380
ctaggccctt ttgctaatca tgttcatacc tcttatcttc ctcccacagc tcctgggcaa   1440
cgtgctggtc tgtgtgctgg cccatcactt tggcaaagca cgtgagatct gaattcgccg   1500
ccaccatgct gtttaacctg agaatcctgc tgaataacgc tgcctttagg aacggacata   1560
acttcatggt ccgcaacttt cgctgtggcc agcctctcca gaacaaagtg cagctgaagg   1620
ggagggacct gctgaccctg aaaaatttca caggagagga aatcaagtac atgctgtggc   1680
tgtctgccga tctgaagttc cggatcaagc agaagggcga atatctgcca ctgctccagg   1740
gcaaaagtct ggggatgatc ttcgaaaaga ggagtactcg gaccagactg tcaacagaga   1800
ctggattcgc tctgctggga ggacacccat gctttctgac cacacaggac attcatctgg   1860
gcgtgaacga gtcactgacc gacacagccc gggtgctgag cagcatggcc gatgccgtgc   1920
tggcacgggt ctacaaacag agcgacctgg ataccctggc taaggaagca agcatcccca   1980
tcattaatgg gctgtccgac ctgtatcacc ctatccagat tctggccgat tacctgaccc   2040
tccaggagca ttattctagt ctgaaaggcc tgacactgag ctggattggg gacggaaaca   2100
atatcctgca ctccattatg atgtctgccg ctaagtttgg gatgcacctc caggcagcca   2160
caccaaaagg ctacgaaccc gatgccagtg tgactaagct ggccgaacag tatgctaaag   2220
agaacggcac taagctgctg ctgaccaatg acccccctgga ggctgcacac ggaggcaacg   2280
tcctgatcac tgatacctgg atcagcatgg gccaggagga agagaagaag aagcggctcc   2340
```

```
aggccttcca gggctaccag gtgacaatga aaactgccaa ggtcgccgct tctgattgga   2400

cttttctgca ttgtctgccc cgaaaacctg aagaggtgga cgatgaggtc ttctattcac   2460

ctaggagcct ggtgtttcca gaagccgaga atcgcaagtg gacaatcatg gccgtgatgg   2520

tgtccctgct gactgactat tccccacagc tgcagaagcc taagttttga gatatcgtcg   2580

actcgctgat cagcctcgac tgtgccttct agttgccagc catctgttgt ttgcccctcc   2640

cccgtgcctt ccttgaccct ggaaggtgcc actcccactg tcctttccta ataaaatgag   2700

gaaattgcat cgcattgtct gagtaggtgt cattctattc tggggggtgg ggtggggcag   2760

gacagcaagg gggaggattg ggaagacaat agcaggcatg ctggggatgc ggtgggctct   2820

atggcttctg aggcggaaag aaccagctgg ggctcgacta gactagtcct gcaggtagag   2880

catggctacg taaggaaccc ctagtgatgg agttggccac tccctctctg cgcgctcgct   2940

cgctcactga ggccgggcga ccaaaggtcg cccgacgccc gggctttgcc cgggcggcct   3000

cagtgagcga gcgagcgcgc agagagggag tggccaa                            3037
```

<210> SEQ ID NO 27
<211> LENGTH: 7338
<212> TYPE: DNA
<213> ORGANISM: Artificial sequence
<220> FEATURE:
<223> OTHER INFORMATION: pAAV2-hOTCenh.hOTCprom.SV40int.hOTCco.BGHpa

<400> SEQUENCE: 27

```
gctagcgatg accctgctga ttggttcgct gaccatttcc gggtgcggga cggcgttacc     60

agaaactcag aaggttcgtc caaccaaacc gactctgacg gcagtttacg agagagatga    120

tagggtctgc ttcagtaagc cagatgctac acaattaggc ttgtacatat tgtcgttaga    180

acgcggctac aattaataca taaccttatg tatcatacac atacgattta ggtgacacta    240

tagaatacac ggaattaatt cttggccact ccctctctgc gcgctcgctc gctcactgag    300

gccgcccggg caaagcccgg gcgtcgggcg acctttggtc gcccggcctc agtgagcgag    360

cgagcgcgca gagagggagt ggccaactcc atcactaggg gttccttacg tagccatgct    420

ctagcgatcg cggtacctta attaattagg gctgattgtt gagacactgg tgaactttga    480

acctctgtga tttccctgtt tgctctgtgc ctgatagctt tcagtctgct aacaaatctc    540

ctttatgcag tttaacctct gtacttccaa tggggaggaa ttggaatcag cctatgggag    600

aagagatagc tctaggattc agatctacaa gaaagttaaa attgaattag aggaatcatg    660

gggtcaacaa gagcccctgg atgaattctg aggatgaaca tcaaagcctg taaagtaaaa    720

cagactccac atgtgacata atcagcagaa gctgggtagt tgaaatctac ccctcaacaa    780

gttcattgag atgccctgcc ttttgagatt cagtgaaatt gcttttaact tcatcccact    840

tgtgatgcag ctcccctttt ccaatccctc tgggagttat tggtatctta acttttttttt   900

agttccctct ggctttgagc tcctgcatct gtagcattag gagggtttgt gagttgcttt    960

ggcatctcag aaatgctgcc tgtactctct agcatggaac tgcagacact tcttgatttc   1020

tccccaagca ttaccaatat gagttgtgtg tatggctagc acagttcagt gaagatatgg   1080

ggtcaagcta tgggctttat attagcctgt ggtttggcct catctccctc aggctccatg   1140

caaacgttca atttcactcc tgtattatgt ggagcgcttt tgctctctga aacctattca   1200

ataactggcc ttgtttgcct cttcaaagat gctttattat gtttttttaaa ttcactctct  1260

cccttctcac ctctgtacct ttgcaagcag ttgcttctgc ctggaatatc ctttccagaa   1320

tggaagattt ggtagaggtt gggaaatgtc agtctttccc ctcactttat ctcacatcat   1380
```

```
tctctgtaag tagaaggaaa tggtgacaat atttatttct ctactagtat taattatgac   1440

atcacaaaca tctcggctcc tgaggtggcc atagttggtc tttaaataac actttttggt   1500

attccacaaa cttctggaaa atatttactt gggtttgcta aagtcatata aattgaccag   1560

aagaggcagc cctacccctg cccctcctct ccttcctcct acccttccta ccttagaggg   1620

ctcccgcttc ttcgaagcca gacaactttg tctggacctc tcctatgggc ttgtattatg   1680

gatatttgtt tataaatcat accaccttta ctgaactgtg aactctgcaa agatgatgtc   1740

atcttccctc tctgaaactt cagtgcagct cggtatctga tacagaattg actttgaatc   1800

acctgatttc taactgagga taaatgaata aatgtgaagt tgcagatggc cccttagtga   1860

tctgaatagg ctgctagggg aagagcatat ggtatcccca cttcccactt gtactgactg   1920

tcaggtgctg ttagaatcaa taggcaacta tttcttttct ttttctttct ttctttcttt   1980

tttttgagac agtgtctctc tctgtcaccc aggctggagt acagtggtgc aatctgggct   2040

cactgcaacc tctgtctccc gggttcaagc gactctcatg cctcagcctc ccaaatagct   2100

gggattacag gtgtgcacca ccacgtctag ctaatttttg tatttttagt ggagacgggg   2160

attcaccatg ttggccaggc tggtctcgaa ctcctgggct caagtgatcc gcccgcctca   2220

gcctcccaaa gtgctgggat tacaggcgtg agccaccgtg cccggccagc aattatttct   2280

ttattgaaga cttatgtgca aggcacaaag ggagctccag gactgagata tttttactat   2340

accttctcta tcatcttgca cccccaaaat agcttccagg gcacttcttt ctatttgttt   2400

ttgtggaaag actggcaatt agaggtagaa aagtgaaata aatggaaata gtactactca   2460

ggactgtcac atctacatct gtgtttttgc agtgccaatt tgcattttct gagtgagtta   2520

cttctactca ccttcacagc agccggtacc gcagtgcctt gcatatatta tatcctcaat   2580

gagtacttgt caattgattt tgtacatgcg tgtgacagta taaatatatt atgaaaaatg   2640

aggaggccag gcaataaaag agtcaggatt tcttccaaaa aaaatacaca gcggtggagc   2700

ttggcataaa gttcaaatgc tcctacaccc tgccctgcag tatctctaac caggggactt   2760

tgataaggaa gctgaagggt gatattacct ttgctccctc actgcaactg aacacatttc   2820

ttagttttta ggtggccccc gctggctaac ttgctgtggc ggccgctcta aggtaaatat   2880

aaaattttta agtgtataat gtgttaaact actgattcta attgtttctc tcttttagat   2940

tccaaccttt ggaactgatc tagagaattc gccgccacca tgctgtttaa cctgagaatc   3000

ctgctgaata acgctgcctt taggaacgga cataacttca tggtccgcaa ctttcgctgt   3060

ggccagcctc tccagaacaa agtgcagctg aaggggaggg acctgctgac cctgaaaaat   3120

ttcacaggag aggaaatcaa gtacatgctg tggctgtctg ccgatctgaa gttccggatc   3180

aagcagaagg gcgaatatct gccactgctc cagggcaaaa gtctggggat gatcttcgaa   3240

aagaggagta ctcggaccag actgtcaaca gagactggat tcgctctgct gggaggacac   3300

ccatgctttc tgaccacaca ggacattcat ctgggcgtga acgagtcact gaccgacaca   3360

gcccgggtgc tgagcagcat ggccgatgcc gtgctggcac gggtctacaa acagagcgac   3420

ctggataccc tggctaagga agcaagcatc cccatcatta atgggctgtc cgacctgtat   3480

caccctatcc agattctggc cgattacctg accctccagg agcattattc tagtctgaaa   3540

ggcctgacac tgagctggat tggggacgga aacaatatcc tgcactccat tatgatgtct   3600

gccgctaagt ttgggatgca cctccaggca gccacaccaa aaggctacga acccgatgcc   3660

agtgtgacta agctggccga acagtatgct aaagagaacg gcactaagct gctgctgacc   3720
```

```
aatgaccccc tggaggctgc acacggaggc aacgtcctga tcactgatac ctggatcagc   3780
atgggccagg aggaagagaa gaagaagcgg ctccaggcct tccagggcta ccaggtgaca   3840
atgaaaactg ccaaggtcgc cgcttctgat tggacttttc tgcattgtct gccccgaaaa   3900
cctgaagagg tggacgatga ggtcttctat tcacctagga gcctggtgtt tccagaagcc   3960
gagaatcgca agtggacaat catggccgtg atggtgtccc tgctgactga ctattcccca   4020
cagctgcaga agcctaagtt ttgagatatc gtcgactcgc tgatcagcct cgactgtgcc   4080
ttctagttgc cagccatctg ttgtttgccc ctcccccgtg ccttccttga ccctggaagg   4140
tgccactccc actgtccttt cctaataaaa tgaggaaatt gcatcgcatt gtctgagtag   4200
gtgtcattct attctggggg gtggggtggg gcaggacagc aagggggagg attgggaaga   4260
caatagcagg catgctgggg atgcggtggg ctctatggct tctgaggcgg aaagaaccag   4320
ctggggctcg actagactag tcctgcaggt agagcatggc tacgtaagga acccctagtg   4380
atggagttgg ccactccctc tctgcgcgct cgctcgctca ctgaggccgg gcgaccaaag   4440
gtcgcccgac gcccgggctt tgcccgggcg gcctcagtga gcgagcgagc gcgcagagag   4500
ggagtggcca actttttgca aaagcctagg cctccaaaaa agcctcctca ctacttctgg   4560
aatagctcag aggccgaggc ggcctcggcc tctgcataaa taaaaaaaat tagtcagcca   4620
tggggcggag aatgggcgga actgggcgga gttaggggcg ggatgggcgg agttaggggc   4680
gggactatgg ttgctgacta attgagatgc atgctttgca tacttctgcc tgctggggag   4740
cctggggact ttccacacct ggttgctgac taattgagat gcatgctttg catacttctg   4800
cctgctgggg agcctgggga ctttccacac cctaactgac acacattcca cagctgcatt   4860
aatgaatcgg ccaacgcgcg gggagaggcg gtttgcgtat tgggcgctct tccgcttcct   4920
cgctcactga ctcgctgcgc tcggtcgttc ggctgcggcg agcggtatca gctcactcaa   4980
aggcggtaat acggttatcc acagaatcag gggataacgc aggaaagaac atgtgagcaa   5040
aaggccagca aaaggccagg aaccgtaaaa aggccgcgtt gctggcgttt ttccataggc   5100
tccgcccccc tgacgagcat cacaaaaatc gacgctcaag tcagaggtgg cgaaacccga   5160
caggactata aagataccag gcgtttcccc ctggaagctc cctcgtgcgc tctcctgttc   5220
cgaccctgcc gcttaccgga tacctgtccg cctttctccc ttcgggaagc gtggcgcttt   5280
ctcatagctc acgctgtagg tatctcagtt cggtgtaggt cgttcgctcc aagctgggct   5340
gtgtgcacga accccccgtt cagcccgacc gctgcgcctt atccggtaac tatcgtcttg   5400
agtccaaccc ggtaagacac gacttatcgc cactggcagc agccactggt aacaggatta   5460
gcagagcgag gtatgtaggc ggtgctacag agttcttgaa gtggtggcct aactacggct   5520
acactagaag aacagtattt ggtatctgcg ctctgctgaa gccagttacc ttcggaaaaa   5580
gagttggtag ctcttgatcc ggcaaacaaa ccaccgctgg tagcggtggt ttttttgttt   5640
gcaagcagca gattacgcgc agaaaaaaag gatctcaaga agatcctttg atcttttcta   5700
cggggtctga cgctcagtgg aacgaaaact cacgttaagg gattttggtc atgagattat   5760
caaaaaggat cttcacctag atccttttaa attaaaaatg aagttttaaa tcaagcccaa   5820
tctgaataat gttacaacca attaaccaat tctgattaga aaaactcatc gagcatcaaa   5880
tgaaactgca atttattcat atcaggatta tcaataccat atttttgaaa aagccgtttc   5940
tgtaatgaag gagaaaactc accgaggcag ttccatagga tggcaagatc ctggtatcgg   6000
tctgcgattc cgactcgtcc aacatcaata caacctatta atttcccctc gtcaaaaata   6060
aggttatcaa gtgagaaatc accatgagtg acgactgaat ccggtgagaa tggcaaaagt   6120
```

```
ttatgcattt ctttccagac ttgttcaaca ggccagccat tacgctcgtc atcaaaatca   6180
ctcgcatcaa ccaaaccgtt attcattcgt gattgcgcct gagcgagacg aaatacgcga   6240
tcgctgttaa aaggacaatt acaaacagga atcgaatgca accggcgcag gaacactgcc   6300
agcgcatcaa caatattttc acctgaatca ggatattctt ctaatacctg gaatgctgtt   6360
tttccgggga tcgcagtggt gagtaaccat gcatcatcag gagtacggat aaaatgcttg   6420
atggtcggaa gaggcataaa ttccgtcagc cagtttagtc tgaccatctc atctgtaaca   6480
tcattggcaa cgctaccttt gccatgtttc agaaacaact ctggcgcatc gggcttccca   6540
tacaagcgat agattgtcgc acctgattgc ccgacattat cgcgagccca tttataccca   6600
tataaatcag catccatgtt ggaatttaat cgcggcctcg acgtttcccg ttgaatatgg   6660
ctcataccgg tactcttcct ttttcaatat tattgaagca tttatcaggg ttattgtctc   6720
atgagcggat acatatttga atgtatttag aaaaataaac aaataggggt tccgcgcaca   6780
tttccccgaa aagtgccacc tgacgtctaa gaaaccatta ttatcatgac attaacctat   6840
aaaaataggc gtatcacgag gccctttcgt ctcgcgcgtt tcggtgatga cggtgaaaac   6900
ctctgacaca tgcagctccc ggagacggtc acagcttgtc tgtaagcgga tgccgggagc   6960
agacaagccc gtcagggcgc gtcagcgggt gttggcgggt gtcggggctg gcttaactat   7020
gcggcatcag agcagattgt actgagagtg caccattcga cgctctccct tatgcgactc   7080
ctgcattagg aagcagccca gtagtaggtt gaggccgttg agcaccgccg ccgcaaggaa   7140
tggtgcatgc aaggagatgg cgcccaacag tcccccggcc acggggcctg ccaccatacc   7200
cacgccgaaa caagcgctca tgagcccgaa gtggcgagcc cgatcttccc catcggtgat   7260
gtcggcgata taggcgccag caaccgcacc tgtggcgccg gtgatgccgg ccacgatgcg   7320
tccggcgtag aggatctg                                                 7338
```

<210> SEQ ID NO 28
<211> LENGTH: 7338
<212> TYPE: DNA
<213> ORGANISM: Artificial sequence
<220> FEATURE:
<223> OTHER INFORMATION: pAAV2-hOTCenh.hAATprom.SV40int.hOTCco.BGHpa

<400> SEQUENCE: 28

```
gctagcgatg accctgctga ttggttcgct gaccatttcc gggtgcggga cggcgttacc     60
agaaactcag aaggttcgtc caaccaaacc gactctgacg gcagtttacg agagagatga    120
tagggtctgc ttcagtaagc cagatgctac acaattaggc ttgtacatat tgtcgttaga    180
acgcggctac aattaataca taaccttatg tatcatacac atacgattta ggtgacacta    240
tagaatacac ggaattaatt cttggccact ccctctctgc gcgctcgctc gctcactgag    300
gccgcccggg caaagcccgg gcgtcgggcg acctttggtc gcccggcctc agtgagcgag    360
cgagcgcgca gagagggagt ggccaactcc atcactaggg gttccttacg tagccatgct    420
ctagcgatcg cggtacctta attaattagg gctgattgtt gagacactgg tgaactttga    480
acctctgtga tttccctgtt tgctctgtgc ctgatagctt tcagtctgct aacaaatctc    540
ctttatgcag tttaacctct gtacttccaa tggggaggaa ttggaatcag cctatgggag    600
aagagatagc tctaggattc agatctccca gtcttgtgtc tgccgggcaa tgagcaaggc    660
tccttcctgt ccaagctccc cgcccctccc cagcctactg cctccacccg aagtctactt    720
cctgggtggg caggaactgg gcactgtgcc cagggcatgc actgcctcca cgcagcaacc    780
```

-continued

```
ctcagagtcc tgagctgaac caagaaggag gagggggtcg ggcctccgag gaaggcctag    840
ccgctgctgc tgccaggaat tccaggttgg aggggcggca acctcctgcc agccttcagg    900
ccactctcct gtgcctgcca gaagagacag agcttgagga gagcttgagg agagcaggaa    960
aggtgggaca ttgctgctgc tgctcactca gttccacagg tgggagggac agcagggctt   1020
agagtggggg tcattgtgca gatgggaaaa caaaggccca gagaggggaa gaaatgccca   1080
ggagctaccg agggcaggcg acctcaacca cagcccagtg ctggagctgt gagtggatgt   1140
agagcagcgg aatatccatt cagccagctc aggggaagga caggggccct gaagccaggg   1200
gatggagctg cagggaaggg agctcagaga gaaggggagg ggagtctgag ctcagtttcc   1260
cgctgcctga aaggagggtg gtacctactc ccttcacagg gtaactgaat gagagactgc   1320
ctggaggaaa gctcttcaag tgtggcccac cccaccccag tgacaccagc ccctgacacg   1380
ggggagggag ggcagcatca ggagggggctt tctgggcaca cccagtaccc gtctctgagc   1440
tttccttgaa ctgttgcatt ttaatcctca cagcagctca acaaggtaca taccgtcacc   1500
atccccattt tacagatagg gaaattgagg ctcggagcgg ttaaacaact cacctgaggc   1560
ctcacagcca gtaagtgggt tccctggtct gaatgtgtgt gctggaggat cctgtgggtc   1620
actcgcctgg tagagcccca aggtggaggc ataaatggga ctggtgaatg acagaagggg   1680
caaaaatgca ctcatccatt cactctgcaa gtatctacgg cacgtacgcc agctcccaag   1740
caggtttgcg ggttgcacag cgggcgatgc aatctgattt aggcttttaa agggattgca   1800
atcaagtggg gccccactag cctcaaccct gtacctcccc tcccctccac ccccagcagt   1860
ctccaaaggc ctccaacaac cccagagtgg gggccatgta tccaaagaaa ctccaagctg   1920
tatacggatc acactggttt tccaggagca aaaacagaaa caggcctgag gctggtcaaa   1980
attgaacctc ctcctgctct gagcagcctg gggggcagac taagcagagg gctgtgcaga   2040
cccacataaa gagcctactg tgtgccaggc acttcacccg aggcacttca caagcatgct   2100
tgggaatgaa acttccaact ctttgggatg caggtgaaac agttcctggt tcagagaggt   2160
gaagcggcct gcctgaggca gcacagctct tctttacaga tgtgcttccc cacctctacc   2220
ctgtctcacg gcccccccatg ccagcctgac ggttgtgtct gcctcagtca tgctccattt   2280
ttccatcggg accatcaaga gggtgtttgt gtctaaggct gactgggtaa ctttggatga   2340
gcggtctctc cgctctgagc ctgtttcctc atctgtcaaa tgggctctaa cccactctga   2400
tctcccaggg cggcagtaag tcttcagcat caggcatttt ggggtgactc agtaaatggt   2460
agatcttgct accagtggaa cagccactaa ggattctgca gtgagagcag agggccagct   2520
aagtggtact ctcccagaga ctgtctgact cacgccaccc cctccacctt ggacacagga   2580
cgctgtggtt tctgagccag gtacaatgac tcctttcggt aagtgcagtg gaagctgtac   2640
actgcccagg caaagcgtcc gggcagcgta ggcgggcgac tcagatccca gccagtggac   2700
ttagcccctg tttgctcctc cgataactgg ggtgaccttg gttaatattc accagcagcc   2760
tcccccgttg cccctctgga tccactgctt aaatacggac gaggacaggg ccctgtctcc   2820
tcagcttcag gcaccaccac tgacctggga cagtgaatgc ggccgctcta aggtaaatat   2880
aaaattttta agtgtataat gtgttaaact actgattcta attgtttctc tcttttagat   2940
tccaaccttt ggaactgatc tagagaattc gccgccacca tgctgtttaa cctgagaatc   3000
ctgctgaata acgctgcctt taggaacgga cataacttca tggtccgcaa ctttcgctgt   3060
ggccagcctc tccagaacaa agtgcagctg aaggggaggg acctgctgac cctgaaaaat   3120
ttcacaggag aggaaatcaa gtacatgctg tggctgtctg ccgatctgaa gttccggatc   3180
```

```
aagcagaagg gcgaatatct gccactgctc cagggcaaaa gtctggggat gatcttcgaa   3240
aagaggagta ctcggaccag actgtcaaca gagactggat tcgctctgct gggaggacac   3300
ccatgctttc tgaccacaca ggacattcat ctgggcgtga acgagtcact gaccgacaca   3360
gcccgggtgc tgagcagcat ggccgatgcc gtgctggcac gggtctacaa acagagcgac   3420
ctggataccc tggctaagga agcaagcatc cccatcatta atgggctgtc cgacctgtat   3480
caccctatcc agattctggc cgattacctg accctccagg agcattattc tagtctgaaa   3540
ggcctgacac tgagctggat tggggacgga aacaatatcc tgcactccat tatgatgtct   3600
gccgctaagt ttgggatgca cctccaggca gccacaccaa aaggctacga acccgatgcc   3660
agtgtgacta agctggccga acagtatgct aaagagaacg gcactaagct gctgctgacc   3720
aatgaccccc tggaggctgc acacggaggc aacgtcctga tcactgatac ctggatcagc   3780
atgggccagg aggaagagaa gaagaagcgg ctccaggcct tccagggcta ccaggtgaca   3840
atgaaaactg ccaaggtcgc cgcttctgat tggacttttc tgcattgtct gccccgaaaa   3900
cctgaagagg tggacgatga ggtcttctat tcacctagga gcctggtgtt tccagaagcc   3960
gagaatcgca agtggacaat catggccgtg atggtgtccc tgctgactga ctattcccca   4020
cagctgcaga agcctaagtt ttgagatatc gtcgactcgc tgatcagcct cgactgtgcc   4080
ttctagttgc cagccatctg ttgtttgccc ctcccccgtg ccttccttga ccctggaagg   4140
tgccactccc actgtccttt cctaataaaa tgaggaaatt gcatcgcatt gtctgagtag   4200
gtgtcattct attctggggg gtggggtggg gcaggacagc aagggggagg attgggaaga   4260
caatagcagg catgctgggg atgcggtggg ctctatggct tctgaggcgg aaagaaccag   4320
ctggggctcg actagactag tcctgcaggt agagcatggc tacgtaagga acccctagtg   4380
atggagttgg ccactccctc tctgcgcgct cgctcgctca ctgaggccgg gcgaccaaag   4440
gtcgcccgac gcccgggctt tgcccgggcg gcctcagtga gcgagcgagc gcgcagagag   4500
ggagtggcca actttttgca aaagcctagg cctccaaaaa agcctcctca ctacttctgg   4560
aatagctcag aggccgaggc ggcctcggcc tctgcataaa taaaaaaaat tagtcagcca   4620
tggggcggag aatgggcgga actgggcgga gttaggggcg ggatgggcgg agttaggggc   4680
gggactatgg ttgctgacta attgagatgc atgctttgca tacttctgcc tgctggggag   4740
cctggggact ttccacacct ggttgctgac taattgagat gcatgctttg catacttctg   4800
cctgctgggg agcctgggga ctttccacac cctaactgac acacattcca cagctgcatt   4860
aatgaatcgg ccaacgcgcg gggagaggcg gtttgcgtat tgggcgctct tccgcttcct   4920
cgctcactga ctcgctgcgc tcggtcgttc ggctgcggcg agcggtatca gctcactcaa   4980
aggcggtaat acggttatcc acagaatcag gggataacgc aggaaagaac atgtgagcaa   5040
aaggccagca aaaggccagg aaccgtaaaa aggccgcgtt gctggcgttt ttccataggc   5100
tccgcccccc tgacgagcat cacaaaaatc gacgctcaag tcagaggtgg cgaaacccga   5160
caggactata aagataccag gcgtttcccc ctggaagctc cctcgtgcgc tctcctgttc   5220
cgaccctgcc gcttaccgga tacctgtccg cctttctccc ttcgggaagc gtggcgcttt   5280
ctcatagctc acgctgtagg tatctcagtt cggtgtaggt cgttcgctcc aagctgggct   5340
gtgtgcacga accccccgtt cagcccgacc gctgcgcctt atccggtaac tatcgtcttg   5400
agtccaaccc ggtaagacac gacttatcgc cactggcagc agccactggt aacaggatta   5460
gcagagcgag gtatgtaggc ggtgctacag agttcttgaa gtggtggcct aactacggct   5520
```

-continued

```
acactagaag aacagtattt ggtatctgcg ctctgctgaa gccagttacc ttcggaaaaa   5580
gagttggtag ctcttgatcc ggcaaacaaa ccaccgctgg tagcggtggt ttttttgttt   5640
gcaagcagca gattacgcgc agaaaaaaag gatctcaaga agatcctttg atcttttcta   5700
cggggtctga cgctcagtgg aacgaaaact cacgttaagg gattttggtc atgagattat   5760
caaaaaggat cttcacctag atccttttaa attaaaaatg aagttttaaa tcaagcccaa   5820
tctgaataat gttacaacca attaaccaat tctgattaga aaaactcatc gagcatcaaa   5880
tgaaactgca atttattcat atcaggatta tcaataccat atttttgaaa aagccgtttc   5940
tgtaatgaag gagaaaactc accgaggcag ttccatagga tggcaagatc ctggtatcgg   6000
tctgcgattc cgactcgtcc aacatcaata caacctatta atttcccctc gtcaaaaata   6060
aggttatcaa gtgagaaatc accatgagtg acgactgaat ccggtgagaa tggcaaaagt   6120
ttatgcattt ctttccagac ttgttcaaca ggccagccat tacgctcgtc atcaaaatca   6180
ctcgcatcaa ccaaaccgtt attcattcgt gattgcgcct gagcgagacg aaatacgcga   6240
tcgctgttaa aaggacaatt acaaacagga atcgaatgca accggcgcag gaacactgcc   6300
agcgcatcaa caatattttc acctgaatca ggatattctt ctaatacctg gaatgctgtt   6360
tttccgggga tcgcagtggt gagtaaccat gcatcatcag gagtacggat aaaatgcttg   6420
atggtcggaa gaggcataaa ttccgtcagc cagtttagtc tgaccatctc atctgtaaca   6480
tcattggcaa cgctaccttt gccatgtttc agaaacaact ctggcgcatc gggcttccca   6540
tacaagcgat agattgtcgc acctgattgc ccgacattat cgcgagccca tttataccca   6600
tataaatcag catccatgtt ggaatttaat cgcggcctcg acgtttcccg ttgaatatgg   6660
ctcataccgg tactcttcct ttttcaatat tattgaagca tttatcaggg ttattgtctc   6720
atgagcggat acatatttga atgtatttag aaaaataaac aaataggggt tccgcgcaca   6780
tttccccgaa aagtgccacc tgacgtctaa gaaaccatta ttatcatgac attaacctat   6840
aaaaataggc gtatcacgag gccctttcgt ctcgcgcgtt tcggtgatga cggtgaaaac   6900
ctctgacaca tgcagctccc ggagacggtc acagcttgtc tgtaagcgga tgccgggagc   6960
agacaagccc gtcagggcgc gtcagcgggt gttggcgggt gtcggggctg gcttaactat   7020
gcggcatcag agcagattgt actgagagtg caccattcga cgctctccct tatgcgactc   7080
ctgcattagg aagcagccca gtagtaggtt gaggccgttg agcaccgccg ccgcaaggaa   7140
tggtgcatgc aaggagatgg cgcccaacag tcccccggcc acggggcctg ccaccatacc   7200
cacgccgaaa caagcgctca tgagcccgaa gtggcgagcc cgatcttccc catcggtgat   7260
gtcggcgata taggcgccag caaccgcacc tgtggcgccg gtgatgccgg ccacgatgcg   7320
tccggcgtag aggatctg                                                 7338
```

<210> SEQ ID NO 29
<211> LENGTH: 6108
<212> TYPE: DNA
<213> ORGANISM: Artificial sequence
<220> FEATURE:
<223> OTHER INFORMATION: pAAV2-2hOTCenh.hOTCprom.SV40int.hOTCco.BGHpa

<400> SEQUENCE: 29

```
gctagcgatg accctgctga ttggttcgct gaccatttcc gggtgcggga cggcgttacc     60
agaaactcag aaggttcgtc caaccaaacc gactctgacg gcagtttacg agagagatga    120
tagggtctgc ttcagtaagc cagatgctac acaattaggc ttgtacatat tgtcgttaga    180
acgcggctac aattaataca taaccttatg tatcatacac atacgattta ggtgacacta    240
```

```
tagaatacac ggaattaatt cttggccact ccctctctgc gcgctcgctc gctcactgag    300
gccgcccggg caaagcccgg gcgtcgggcg acctttggtc gcccggcctc agtgagcgag    360
cgagcgcgca gagagggagt ggccaactcc atcactaggg gttccttacg tagccatgct    420
ctagcgatcg cggtacctta attaattagg gctgattgtt gagacactgg tgaactttga    480
acctctgtga tttccctgtt tgctctgtgc ctgatagctt tcagtctgct aacaaatctc    540
ctttatgcag tttaacctct gtacttccaa tggggaggaa ttggaatcag cctatgggag    600
aagagatagc tctaggattc ttagggctga ttgttgagac actggtgaac tttgaacctc    660
tgtgatttcc ctgtttgctc tgtgcctgat agctttcagt ctgctaacaa atctccttta    720
tgcagtttaa cctctgtact tccaatgggg aggaattgga atcagcctat gggagaagag    780
atagctctag gattcagatc tcaagcgact ctcatgcctc agcctcccaa atagctggga    840
ttacaggtgt gcaccaccac gtctagctaa tttttgtatt tttagtggag acggggattc    900
atcatgttgg ccaggctggt ctcgaactcc tgggctcaag tgatccgccc gcctcagcct    960
cccaaagtgc tgggattata ggcgtgagcc accatgcccg gccagcaatt atttctttat   1020
tgaagactta tgtgcaaggc acaaagggag ctccaggact gagatatttt tactatacct   1080
tctctatcat cttgcacccc caaaatagct tccagggcac ttctatttgt ttttgtggaa   1140
agactggcaa ttagaggtag aaaagtgaaa taaatggaaa tagtactact cagggctgtc   1200
acatctacat ctgtgttttt gcagtgccaa tttgcatttt ctgagtgagt tacttctact   1260
caccttcaca gcagccagta ccgcagtgcc ttgcatatat tatatcctca atgagtactt   1320
gtcaattgat tttgtacatg cgtgtgacag tataaatata ttatgaaaaa tgaggaggcc   1380
aggcaataaa agagtcagga tttcttccaa aaaaaataca cagcggtgga gcttggcata   1440
aagttcaaat gctcctacac cctgccctgc agtatctcta accaggggac tttgataagg   1500
aagctgaagg gtgatattac ctttgctccc tcactgcaac tgaacacatt tcttagtttt   1560
taggtggccc ccgctggcta acttgctgtg gcggccgctc taaggtaaat ataaaatttt   1620
taagtgtata atgtgttaaa ctactgattc taattgtttc tctcttttag attccaacct   1680
ttggaactga tctagagaat tcgccgccac catgctgttt aacctgagaa tcctgctgaa   1740
taacgctgcc tttaggaacg gacataactt catggtccgc aactttcgct gtggccagcc   1800
tctccagaac aaagtgcagc tgaaggggag ggacctgctg accctgaaaa atttcacagg   1860
agaggaaatc aagtacatgc tgtggctgtc tgccgatctg aagttccgga tcaagcagaa   1920
gggcgaatat ctgccactgc tccagggcaa aagtctgggg atgatcttcg aaaagaggag   1980
tactcggacc agactgtcaa cagagactgg attcgctctg ctgggaggac acccatgctt   2040
tctgaccaca caggacattc atctgggcgt gaacgagtca ctgaccgaca cagcccgggt   2100
gctgagcagc atggccgatg ccgtgctggc acgggtctac aaacagagcg acctggatac   2160
cctggctaag gaagcaagca tccccatcat taatgggctg tccgacctgt atcaccctat   2220
ccagattctg gccgattacc tgaccctcca ggagcattat tctagtctga aaggcctgac   2280
actgagctgg attggggacg gaaacaatat cctgcactcc attatgatgt ctgccgctaa   2340
gtttgggatg cacctccagg cagccacacc aaaaggctac gaacccgatg ccagtgtgac   2400
taagctggcc gaacagtatg ctaaagagaa cggcactaag ctgctgctga ccaatgaccc   2460
cctggaggct gcacacggag gcaacgtcct gatcactgat acctggatca gcatgggcca   2520
ggaggaagag aagaagaagc ggctccaggc cttccagggc taccaggtga caatgaaaac   2580
```

```
tgccaaggtc gccgcttctg attggacttt tctgcattgt ctgccccgaa aacctgaaga   2640
ggtggacgat gaggtcttct attcacctag gagcctggtg tttccagaag ccgagaatcg   2700
caagtggaca atcatggccg tgatggtgtc cctgctgact gactattccc cacagctgca   2760
gaagcctaag ttttgagata tcgtcgactc gctgatcagc ctcgactgtg ccttctagtt   2820
gccagccatc tgttgtttgc ccctcccccg tgccttcctt gaccctggaa ggtgccactc   2880
ccactgtcct ttcctaataa aatgaggaaa ttgcatcgca ttgtctgagt aggtgtcatt   2940
ctattctggg gggtggggtg gggcaggaca gcaaggggga ggattgggaa gacaatagca   3000
ggcatgctgg ggatgcggtg ggctctatgg cttctgaggc ggaaagaacc agctggggct   3060
cgactagact agtcctgcag gtagagcatg gctacgtaag gaacccctag tgatggagtt   3120
ggccactccc tctctgcgcg ctcgctcgct cactgaggcc gggcgaccaa aggtcgcccg   3180
acgcccgggc tttgcccggg cggcctcagt gagcgagcga gcgcgcagag agggagtggc   3240
caactttttg caaaagccta ggcctccaaa aaagcctcct cactacttct ggaatagctc   3300
agaggccgag gcggcctcgg cctctgcata aataaaaaaa attagtcagc catggggcgg   3360
agaatgggcg gaactgggcg gagttagggg cgggatgggc ggagttaggg gcgggactat   3420
ggttgctgac taattgagat gcatgctttg catacttctg cctgctgggg agcctgggga   3480
ctttccacac ctggttgctg actaattgag atgcatgctt tgcatacttc tgcctgctgg   3540
ggagcctggg gactttccac accctaactg acacacattc cacagctgca ttaatgaatc   3600
ggccaacgcg cggggagagg cggtttgcgt attgggcgct cttccgcttc ctcgctcact   3660
gactcgctgc gctcggtcgt tcggctgcgg cgagcggtat cagctcactc aaaggcggta   3720
atacggttat ccacagaatc aggggataac gcaggaaaga acatgtgagc aaaaggccag   3780
caaaaggcca ggaaccgtaa aaaggccgcg ttgctggcgt ttttccatag gctccgcccc   3840
cctgacgagc atcacaaaaa tcgacgctca agtcagaggt ggcgaaaccc gacaggacta   3900
taaagatacc aggcgtttcc ccctggaagc tccctcgtgc gctctcctgt tccgaccctg   3960
ccgcttaccg gatacctgtc cgcctttctc ccttcgggaa gcgtggcgct ttctcatagc   4020
tcacgctgta ggtatctcag ttcggtgtag gtcgttcgct ccaagctggg ctgtgtgcac   4080
gaaccccccg ttcagcccga ccgctgcgcc ttatccggta actatcgtct tgagtccaac   4140
ccggtaagac acgacttatc gccactggca gcagccactg gtaacaggat tagcagagcg   4200
aggtatgtag gcggtgctac agagttcttg aagtggtggc ctaactacgg ctacactaga   4260
agaacagtat ttggtatctg cgctctgctg aagccagtta ccttcggaaa aagagttggt   4320
agctcttgat ccggcaaaca aaccaccgct ggtagcggtg gtttttttgt ttgcaagcag   4380
cagattacgc gcagaaaaaa aggatctcaa gaagatcctt tgatcttttc tacggggtct   4440
gacgctcagt ggaacgaaaa ctcacgttaa gggattttgg tcatgagatt atcaaaaagg   4500
atcttcacct agatcctttt aaattaaaaa tgaagtttta aatcaatcta aagtatatat   4560
gagtaaactt ggtctgacag ttaccaatgc ttaatcagtg aggcacctat ctcagcgatc   4620
tgtctatttc gttcatccat agttgcctga ctccccgtcg tgtagataac tacgatacgg   4680
gagggcttac catctggccc cagtgctgca atgataccgc gagacccacg ctcaccggct   4740
ccagatttat cagcaataaa ccagccagcc ggaagggccg agcgcagaag tggtcctgca   4800
actttatccg cctccatcca gtctattaat tgttgccggg aagctagagt aagtagttcg   4860
ccagttaata gtttgcgcaa cgttgttgcc attgctacag gcatcgtggt gtcacgctcg   4920
tcgtttggta tggcttcatt cagctccggt tcccaacgat caaggcgagt tacatgatcc   4980
```

```
cccatgttgt gcaaaaaagc ggttagctcc ttcggtcctc cgatcgttgt cagaagtaag   5040

ttggccgcag tgttatcact catggttatg gcagcactgc ataattctct tactgtcatg   5100

ccatccgtaa gatgcttttc tgtgactggt gagtactcaa ccaagtcatt ctgagaatag   5160

tgtatgcggc gaccgagttg ctcttgcccg gcgtcaatac gggataatac cgcgccacat   5220

agcagaactt taaaagtgct catcattgga aaacgttctt cggggcgaaa actctcaagg   5280

atcttaccgc tgttgagatc cagttcgatg taacccactc gtgcacccaa ctgatcttca   5340

gcatctttta ctttcaccag cgtttctggg tgagcaaaaa caggaaggca aaatgccgca   5400

aaaaagggaa taagggcgac acggaaatgt tgaatactca tactcttcct ttttcaatat   5460

tattgaagca tttatcaggg ttattgtctc atgagcggat acatatttga atgtatttag   5520

aaaaataaac aaataggggt tccgcgcaca tttccccgaa aagtgccacc tgacgtctaa   5580

gaaaccatta ttatcatgac attaacctat aaaaataggc gtatcacgag gccctttcgt   5640

ctcgcgcgtt tcggtgatga cggtgaaaac ctctgacaca tgcagctccc ggagacggtc   5700

acagcttgtc tgtaagcgga tgccgggagc agacaagccc gtcagggcgc gtcagcgggt   5760

gttggcgggt gtcggggctg gcttaactat gcggcatcag agcagattgt actgagagtg   5820

caccattcga cgctctccct tatgcgactc ctgcattagg aagcagccca gtagtaggtt   5880

gaggccgttg agcaccgccg ccgcaaggaa tggtgcatgc aaggagatgg cgcccaacag   5940

tcccccggcc acggggcctg ccaccatacc cacgccgaaa caagcgctca tgagcccgaa   6000

gtggcgagcc cgatcttccc catcggtgat gtcggcgata taggcgccag caaccgcacc   6060

tgtggcgccg gtgatgccgg ccacgatgcg tccggcgtag aggatctg                6108
```

```
<210> SEQ ID NO 30
<211> LENGTH: 6554
<212> TYPE: DNA
<213> ORGANISM: Artificial sequence
<220> FEATURE:
<223> OTHER INFORMATION: pAAV2-2hOTCenh.hOTCprom.beta gint.hOTCco.BGHpa

<400> SEQUENCE: 30

gctagcgatg accctgctga ttggttcgct gaccatttcc gggtgcggga cggcgttacc     60

agaaactcag aaggttcgtc caaccaaacc gactctgacg gcagtttacg agagagatga    120

tagggtctgc ttcagtaagc cagatgctac acaattaggc ttgtacatat tgtcgttaga    180

acgcggctac aattaataca taaccttatg tatcatacac atacgattta ggtgacacta    240

tagaatacac ggaattaatt cttggccact ccctctctgc gcgctcgctc gctcactgag    300

gccgcccggg caaagcccgg gcgtcgggcg acctttggtc gcccggcctc agtgagcgag    360

cgagcgcgca gagagggagt ggccaactcc atcactaggg gttccttacg tagccatgct    420

ctagcgatcg cggtacctta attaattagg gctgattgtt gagacactgg tgaactttga    480

acctctgtga tttccctgtt tgctctgtgc ctgatagctt tcagtctgct aacaaatctc    540

ctttatgcag tttaacctct gtacttccaa tggggaggaa ttggaatcag cctatgggag    600

aagagatagc tctaggattc ttagggctga ttgttgagac actggtgaac tttgaacctc    660

tgtgatttcc ctgtttgctc tgtgcctgat agctttcagt ctgctaacaa atctccttta    720

tgcagtttaa cctctgtact tccaatgggg aggaattgga atcagcctat gggagaagag    780

atagctctag gattcagatc tcaagcgact ctcatgcctc agcctcccaa atagctggga    840

ttacaggtgt gcaccaccac gtctagctaa tttttgtatt tttagtggag acggggattc    900
```

```
atcatgttgg ccaggctggt ctcgaactcc tgggctcaag tgatccgccc gcctcagcct    960
cccaaagtgc tgggattata ggcgtgagcc accatgcccg gccagcaatt atttctttat   1020
tgaagactta tgtgcaaggc acaaagggag ctccaggact gagatatttt tactatacct   1080
tctctatcat cttgcacccc caaaatagct tccagggcac ttctatttgt ttttgtggaa   1140
agactggcaa ttagaggtag aaaagtgaaa taaatggaaa tagtactact cagggctgtc   1200
acatctacat ctgtgttttt gcagtgccaa tttgcatttt ctgagtgagt tacttctact   1260
caccttcaca gcagccagta ccgcagtgcc ttgcatatat tatatcctca atgagtactt   1320
gtcaattgat tttgtacatg cgtgtgacag tataaatata ttatgaaaaa tgaggaggcc   1380
aggcaataaa agagtcagga tttcttccaa aaaaaataca cagcggtgga gcttggcata   1440
aagttcaaat gctcctacac cctgccctgc agtatctcta accaggggac tttgataagg   1500
aagctgaagg gtgatattac ctttgctccc tcactgcaac tgaacacatt tcttagtttt   1560
taggtggccc ccgctggcta acttgctgtg gcggccgctg agaacttcag ggtgagtcta   1620
tgggaccctt gatgttttct ttccccttct tttctatggt taagttcatg tcataggaag   1680
gggagaagta acagggtaca catattgacc aaatcagggt aattttgcat ttgtaatttt   1740
aaaaaatgct ttcttctttt aatatacttt tttgtttatc ttatttctaa tactttccct   1800
aatctctttc tttcagggca ataatgatac aatgtatcat gcctctttgc accattctaa   1860
agaataacag tgataatttc tgggttaagg caatagcaat atttctgcat ataaatattt   1920
ctgcatataa attgtaactg atgtaagagg tttcatattg ctaatagcag ctacaatcca   1980
gctaccattc tgcttttatt ttatggttgg gataaggctg gattattctg agtccaagct   2040
aggccctttt gctaatcatg ttcatacctc ttatcttcct cccacagctc ctgggcaacg   2100
tgctggtctg tgtgctggcc catcactttg gcaaagcacg tggaattcgc cgccaccatg   2160
ctgtttaacc tgagaatcct gctgaataac gctgccttta ggaacggaca taacttcatg   2220
gtccgcaact ttcgctgtgg ccagcctctc cagaacaaag tgcagctgaa ggggagggac   2280
ctgctgaccc tgaaaaattt cacaggagag gaaatcaagt acatgctgtg gctgtctgcc   2340
gatctgaagt tccggatcaa gcagaagggc gaatatctgc cactgctcca gggcaaaagt   2400
ctggggatga tcttcgaaaa gaggagtact cggaccagac tgtcaacaga gactggattc   2460
gctctgctgg gaggacaccc atgctttctg accacacagg acattcatct gggcgtgaac   2520
gagtcactga ccgacacagc ccgggtgctg agcagcatgg ccgatgccgt gctggcacgg   2580
gtctacaaac agagcgacct ggataccctg gctaaggaag caagcatccc catcattaat   2640
gggctgtccg acctgtatca ccctatccag attctggccg attacctgac cctccaggag   2700
cattattcta gtctgaaagg cctgacactg agctggattg gggacggaaa caatatcctg   2760
cactccatta tgatgtctgc cgctaagttt gggatgcacc tccaggcagc cacaccaaaa   2820
ggctacgaac ccgatgccag tgtgactaag ctggccgaac agtatgctaa agagaacggc   2880
actaagctgc tgctgaccaa tgacccccctg gaggctgcac acggaggcaa cgtcctgatc   2940
actgatacct ggatcagcat gggccaggag gaagagaaga agaagcggct ccaggccttc   3000
cagggctacc aggtgacaat gaaaactgcc aaggtcgccg cttctgattg gacttttctg   3060
cattgtctgc cccgaaaacc tgaagaggtg gacgatgagg tcttctattc acctaggagc   3120
ctggtgtttc cagaagccga gaatcgcaag tggacaatca tggccgtgat ggtgtccctg   3180
ctgactgact attccccaca gctgcagaag cctaagtttt gagatatcgt cgactcgctg   3240
atcagcctcg actgtgcctt ctagttgcca gccatctgtt gtttgcccct cccccgtgcc   3300
```

```
ttccttgacc ctggaaggtg ccactcccac tgtcctttcc taataaaatg aggaaattgc   3360
atcgcattgt ctgagtaggt gtcattctat tctggggggt ggggtggggc aggacagcaa   3420
gggggaggat tgggaagaca atagcaggca tgctggggat gcggtgggct ctatggcttc   3480
tgaggcggaa agaaccagct ggggctcgac tagactagtc ctgcaggtag agcatggcta   3540
cgtaaggaac ccctagtgat ggagttggcc actccctctc tgcgcgctcg ctcgctcact   3600
gaggccgggc gaccaaaggt cgcccgacgc ccgggctttg cccgggcggc ctcagtgagc   3660
gagcgagcgc gcagagaggg agtggccaac tttttgcaaa agcctaggcc tccaaaaaag   3720
cctcctcact acttctggaa tagctcagag gccgaggcgg cctcggcctc tgcataaata   3780
aaaaaaatta gtcagccatg gggcggagaa tgggcggaac tgggcggagt taggggcggg   3840
atgggcggag ttaggggcgg gactatggtt gctgactaat tgagatgcat gctttgcata   3900
cttctgcctg ctggggagcc tggggacttt ccacacctgg ttgctgacta attgagatgc   3960
atgctttgca tacttctgcc tgctggggag cctggggact ttccacaccc taactgacac   4020
acattccaca gctgcattaa tgaatcggcc aacgcgcggg gagaggcggt ttgcgtattg   4080
ggcgctcttc cgcttcctcg ctcactgact cgctgcgctc ggtcgttcgg ctgcggcgag   4140
cggtatcagc tcactcaaag gcggtaatac ggttatccac agaatcaggg gataacgcag   4200
gaaagaacat gtgagcaaaa ggccagcaaa aggccaggaa ccgtaaaaag gccgcgttgc   4260
tggcgttttt ccataggctc cgcccccctg acgagcatca caaaaatcga cgctcaagtc   4320
agaggtggcg aaacccgaca ggactataaa gataccaggc gtttccccct ggaagctccc   4380
tcgtgcgctc tcctgttccg accctgccgc ttaccggata cctgtccgcc tttctccctt   4440
cgggaagcgt ggcgctttct catagctcac gctgtaggta tctcagttcg gtgtaggtcg   4500
ttcgctccaa gctgggctgt gtgcacgaac cccccgttca gcccgaccgc tgcgccttat   4560
ccggtaacta tcgtcttgag tccaacccgg taagacacga cttatcgcca ctggcagcag   4620
ccactggtaa caggattagc agagcgaggt atgtaggcgg tgctacagag ttcttgaagt   4680
ggtggcctaa ctacggctac actagaagaa cagtatttgg tatctgcgct ctgctgaagc   4740
cagttacctt cggaaaaaga gttggtagct cttgatccgg caaacaaacc accgctggta   4800
gcggtggttt ttttgtttgc aagcagcaga ttacgcgcag aaaaaaagga tctcaagaag   4860
atcctttgat cttttctacg gggtctgacg ctcagtggaa cgaaaactca cgttaaggga   4920
ttttggtcat gagattatca aaaaggatct tcacctagat ccttttaaat taaaaatgaa   4980
gttttaaatc aatctaaagt atatatgagt aaacttggtc tgacagttac caatgcttaa   5040
tcagtgaggc acctatctca gcgatctgtc tatttcgttc atccatagtt gcctgactcc   5100
ccgtcgtgta gataactacg atacgggagg gcttaccatc tggccccagt gctgcaatga   5160
taccgcgaga cccacgctca ccggctccag atttatcagc aataaaccag ccagccggaa   5220
gggccgagcg cagaagtggt cctgcaactt tatccgcctc catccagtct attaattgtt   5280
gccgggaagc tagagtaagt agttcgccag ttaatagttt gcgcaacgtt gttgccattg   5340
ctacaggcat cgtggtgtca cgctcgtcgt ttggtatggc ttcattcagc tccggttccc   5400
aacgatcaag gcgagttaca tgatccccca tgttgtgcaa aaaagcggtt agctccttcg   5460
gtcctccgat cgttgtcaga agtaagttgg ccgcagtgtt atcactcatg gttatggcag   5520
cactgcataa ttctcttact gtcatgccat ccgtaagatg cttttctgtg actggtgagt   5580
actcaaccaa gtcattctga gaatagtgta tgcggcgacc gagttgctct tgcccggcgt   5640
```

caatacggga taataccgcg ccacatagca gaactttaaa agtgctcatc attggaaaac 5700
gttcttcggg gcgaaaactc tcaaggatct taccgctgtt gagatccagt tcgatgtaac 5760
ccactcgtgc acccaactga tcttcagcat cttttacttt caccagcgtt tctgggtgag 5820
caaaaacagg aaggcaaaat gccgcaaaaa agggaataag ggcgacacgg aaatgttgaa 5880
tactcatact cttccttttt caatattatt gaagcattta tcagggttat tgtctcatga 5940
gcggatacat atttgaatgt atttagaaaa ataaacaaat aggggttccg cgcacatttc 6000
cccgaaaagt gccacctgac gtctaagaaa ccattattat catgacatta acctataaaa 6060
ataggcgtat cacgaggccc tttcgtctcg cgcgtttcgg tgatgacggt gaaaacctct 6120
gacacatgca gctcccggag acggtcacag cttgtctgta agcggatgcc gggagcagac 6180
aagcccgtca gggcgcgtca gcgggtgttg gcgggtgtcg gggctggctt aactatgcgg 6240
catcagagca gattgtactg agagtgcacc attcgacgct ctcccttatg cgactcctgc 6300
attaggaagc agcccagtag taggttgagg ccgttgagca ccgccgccgc aaggaatggt 6360
gcatgcaagg agatggcgcc caacagtccc ccggccacgg ggcctgccac catacccacg 6420
ccgaaacaag cgctcatgag cccgaagtgg cgagcccgat cttccccatc ggtgatgtcg 6480
gcgatatagg cgccagcaac cgcacctgtg gcgccggtga tgccggccac gatgcgtccg 6540
gcgtagagga tctg 6554

<210> SEQ ID NO 31
<211> LENGTH: 5711
<212> TYPE: DNA
<213> ORGANISM: Artificial sequence
<220> FEATURE:
<223> OTHER INFORMATION: pAAV2-2hOTCenh.hAATprom.SV40int.hOTCco.BGHpa

<400> SEQUENCE: 31
gctagcgatg accctgctga ttggttcgct gaccatttcc gggtgcggga cggcgttacc 60
agaaactcag aaggttcgtc caaccaaacc gactctgacg gcagtttacg agagagatga 120
tagggtctgc ttcagtaagc cagatgctac acaattaggc ttgtacatat tgtcgttaga 180
acgcggctac aattaataca taaccttatg tatcatacac atacgattta ggtgacacta 240
tagaatacac ggaattaatt cttggccact ccctctctgc gcgctcgctc gctcactgag 300
gccgcccggg caaagcccgg gcgtcgggcg acctttggtc gcccggcctc agtgagcgag 360
cgagcgcgca gagagggagt ggccaactcc atcactaggg gttccttacg tagccatgct 420
ctagcgatcg cggtacctta attaattagg gctgattgtt gagacactgg tgaactttga 480
acctctgtga tttccctgtt tgctctgtgc ctgatagctt tcagtctgct aacaaatctc 540
ctttatgcag tttaacctct gtacttccaa tggggaggaa ttggaatcag cctatgggag 600
aagagatagc tctaggattc ttagggctga ttgttgagac actggtgaac tttgaacctc 660
tgtgatttcc ctgtttgctc tgtgcctgat agctttcagt ctgctaacaa atctccttta 720
tgcagtttaa cctctgtact tccaatgggg aggaattgga atcagcctat gggagaagag 780
atagctctag gattcagatc ttgctaccag tggaacagcc actaaggatt ctgcagtgag 840
agcagagggc cagctaagtg gtactctccc agagactgtc tgactcacgc cacccccctcc 900 accttggaca caggacgctg tggtttctga gccaggtaca atgactcctt tcggtaagtg 960
cagtggaagc tgtacactgc ccaggcaaag cgtccgggca gcgtaggcgg gcgactcaga 1020
tcccagccag tggacttagc ccctgtttgc tcctccgata actggggtga ccttggttaa 1080
tattcaccag cagcctcccc cgttgcccct ctggatccac tgcttaaata cggacgagga 1140

```
cagggccctg tctcctcagc ttcaggcacc accactgacc tgggacagtg aatgcggccg   1200
ctctaaggta aatataaaat ttttaagtgt ataatgtgtt aaactactga ttctaattgt   1260
ttctctcttt tagattccaa cctttggaac tgatctagag aattcgccgc caccatgctg   1320
tttaacctga gaatcctgct gaataacgct gcctttagga acggacataa cttcatggtc   1380
cgcaactttc gctgtggcca gcctctccag aacaaagtgc agctgaaggg gagggacctg   1440
ctgaccctga aaaatttcac aggagaggaa atcaagtaca tgctgtggct gtctgccgat   1500
ctgaagttcc ggatcaagca gaagggcgaa tatctgccac tgctccaggg caaaagtctg   1560
gggatgatct tcgaaaagag gagtactcgg accagactgt caacagagac tggattcgct   1620
ctgctgggag gacacccatg ctttctgacc acacaggaca ttcatctggg cgtgaacgag   1680
tcactgaccg acacagcccg ggtgctgagc agcatggccg atgccgtgct ggcacgggtc   1740
tacaaacaga gcgacctgga taccctggct aaggaagcaa gcatccccat cattaatggg   1800
ctgtccgacc tgtatcaccc tatccagatt ctggccgatt acctgaccct ccaggagcat   1860
tattctagtc tgaaaggcct gacactgagc tggattgggg acggaaacaa tatcctgcac   1920
tccattatga tgtctgccgc taagtttggg atgcacctcc aggcagccac accaaaaggc   1980
tacgaacccg atgccagtgt gactaagctg gccgaacagt atgctaaaga gaacggcact   2040
aagctgctgc tgaccaatga ccccctggag gctgcacacg gaggcaacgt cctgatcact   2100
gatacctgga tcagcatggg ccaggaggaa gagaagaaga agcggctcca ggccttccag   2160
ggctaccagg tgacaatgaa aactgccaag gtcgccgctt ctgattggac ttttctgcat   2220
tgtctgcccc gaaaacctga agaggtggac gatgaggtct tctattcacc taggagcctg   2280
gtgtttccag aagccgagaa tcgcaagtgg acaatcatgg ccgtgatggt gtccctgctg   2340
actgactatt ccccacagct gcagaagcct aagttttgag atatcgtcga ctcgctgatc   2400
agcctcgact gtgccttcta gttgccagcc atctgttgtt tgcccctccc ccgtgccttc   2460
cttgaccctg gaaggtgcca ctcccactgt cctttcctaa taaaatgagg aaattgcatc   2520
gcattgtctg agtaggtgtc attctattct ggggggtggg gtggggcagg acagcaaggg   2580
ggaggattgg gaagacaata gcaggcatgc tggggatgcg gtgggctcta tggcttctga   2640
ggcggaaaga accagctggg gctcgactag actagtcctg caggtagagc atggctacgt   2700
aaggaacccc tagtgatgga gttggccact ccctctctgc gcgctcgctc gctcactgag   2760
gccgggcgac caaaggtcgc ccgacgcccg ggctttgccc gggcggcctc agtgagcgag   2820
cgagcgcgca gagagggagt ggccaacttt ttgcaaaagc ctaggcctcc aaaaaagcct   2880
cctcactact tctggaatag ctcagaggcc gaggcggcct cggcctctgc ataaataaaa   2940
aaaattagtc agccatgggg cggagaatgg gcggaactgg gcggagttag gggcgggatg   3000
ggcggagtta ggggcgggac tatggttgct gactaattga gatgcatgct ttgcatactt   3060
ctgcctgctg gggagcctgg ggactttcca cacctggttg ctgactaatt gagatgcatg   3120
ctttgcatac ttctgcctgc tggggagcct ggggactttc cacaccctaa ctgacacaca   3180
ttccacagct gcattaatga atcggccaac gcgcggggag aggcggtttg cgtattgggc   3240
gctcttccgc ttcctcgctc actgactcgc tgcgctcggt cgttcggctg cggcgagcgg   3300
tatcagctca ctcaaaggcg gtaatacggt tatccacaga atcaggggat aacgcaggaa   3360
agaacatgtg agcaaaaggc cagcaaaagg ccaggaaccg taaaaaggcc gcgttgctgg   3420
cgtttttcca taggctccgc ccccctgacg agcatcacaa aaatcgacgc tcaagtcaga   3480
```

ggtggcgaaa cccgacagga ctataaagat accaggcgtt tccccctgga agctccctcg 3540
tgcgctctcc tgttccgacc ctgccgctta ccggatacct gtccgccttt ctcccttcgg 3600
gaagcgtggc gctttctcat agctcacgct gtaggtatct cagttcggtg taggtcgttc 3660
gctccaagct gggctgtgtg cacgaacccc ccgttcagcc cgaccgctgc gccttatccg 3720
gtaactatcg tcttgagtcc aacccggtaa gacacgactt atcgccactg gcagcagcca 3780
ctggtaacag gattagcaga gcgaggtatg taggcggtgc tacagagttc ttgaagtggt 3840
ggcctaacta cggctacact agaagaacag tatttggtat ctgcgctctg ctgaagccag 3900
ttaccttcgg aaaaagagtt ggtagctctt gatccggcaa acaaaccacc gctggtagcg 3960
gtggtttttt tgtttgcaag cagcagatta cgcgcagaaa aaaaggatct caagaagatc 4020
ctttgatctt ttctacgggg tctgacgctc agtggaacga aaactcacgt taagggattt 4080
tggtcatgag attatcaaaa aggatcttca cctagatcct tttaaattaa aaatgaagtt 4140
ttaaatcaat ctaaagtata tatgagtaaa cttggtctga cagttaccaa tgcttaatca 4200
gtgaggcacc tatctcagcg atctgtctat ttcgttcatc catagttgcc tgactccccg 4260
tcgtgtagat aactacgata cgggagggct taccatctgg ccccagtgct gcaatgatac 4320
cgcgagaccc acgctcaccg gctccagatt tatcagcaat aaaccagcca gccggaaggg 4380
ccgagcgcag aagtggtcct gcaactttat ccgcctccat ccagtctatt aattgttgcc 4440
gggaagctag agtaagtagt tcgccagtta atagtttgcg caacgttgtt gccattgcta 4500
caggcatcgt ggtgtcacgc tcgtcgtttg gtatggcttc attcagctcc ggttcccaac 4560
gatcaaggcg agttacatga tcccccatgt tgtgcaaaaa agcggttagc tccttcggtc 4620
ctccgatcgt tgtcagaagt aagttggccg cagtgttatc actcatggtt atggcagcac 4680
tgcataattc tcttactgtc atgccatccg taagatgctt ttctgtgact ggtgagtact 4740
caaccaagtc attctgagaa tagtgtatgc ggcgaccgag ttgctcttgc ccggcgtcaa 4800
tacgggataa taccgcgcca catagcagaa ctttaaaagt gctcatcatt ggaaaacgtt 4860
cttcggggcg aaaactctca aggatcttac cgctgttgag atccagttcg atgtaaccca 4920
ctcgtgcacc caactgatct tcagcatctt ttactttcac cagcgtttct gggtgagcaa 4980
aaacaggaag gcaaaatgcc gcaaaaaagg gaataagggc gacacggaaa tgttgaatac 5040
tcatactctt cctttttcaa tattattgaa gcatttatca gggttattgt ctcatgagcg 5100
gatacatatt tgaatgtatt tagaaaaata aacaaatagg ggttccgcgc acatttcccc 5160
gaaaagtgcc acctgacgtc taagaaacca ttattatcat gacattaacc tataaaaata 5220
ggcgtatcac gaggcccttt cgtctcgcgc gtttcggtga tgacggtgaa aacctctgac 5280
acatgcagct cccggagacg gtcacagctt gtctgtaagc ggatgccggg agcagacaag 5340
cccgtcaggg cgcgtcagcg ggtgttggcg ggtgtcgggg ctggcttaac tatgcggcat 5400
cagagcagat tgtactgaga gtgcaccatt cgacgctctc ccttatgcga ctcctgcatt 5460
aggaagcagc ccagtagtag gttgaggccg ttgagcaccg ccgccgcaag gaatggtgca 5520
tgcaaggaga tggcgcccaa cagtcccccg gccacggggc ctgccaccat acccacgccg 5580
aaacaagcgc tcatgagccc gaagtggcga gcccgatctt ccccatcggt gatgtcggcg 5640
atataggcgc cagcaaccgc acctgtggcg ccggtgatgc cggccacgat gcgtccggcg 5700
tagaggatct g 5711

<210> SEQ ID NO 32
<211> LENGTH: 6163

```
<212> TYPE: DNA
<213> ORGANISM: Artificial sequence
<220> FEATURE:
<223> OTHER INFORMATION: pAAV2-2hOTCenh.hAATprom.beta gint.hOTCco.BGHpa

<400> SEQUENCE: 32

gctagcgatg accctgctga ttggttcgct gaccatttcc gggtgcggga cggcgttacc      60

agaaactcag aaggttcgtc caaccaaacc gactctgacg gcagtttacg agagagatga     120

tagggtctgc ttcagtaagc cagatgctac acaattaggc ttgtacatat tgtcgttaga     180

acgcggctac aattaataca taaccttatg tatcatacac atacgattta ggtgacacta     240

tagaatacac ggaattaatt cttggccact ccctctctgc gcgctcgctc gctcactgag     300

gccgcccggg caaagcccgg gcgtcgggcg acctttggtc gcccggcctc agtgagcgag     360

cgagcgcgca gagagggagt ggccaactcc atcactaggg gttccttacg tagccatgct     420

ctagcgatcg cggtacctta attaattagg gctgattgtt gagacactgg tgaactttga     480

acctctgtga tttccctgtt tgctctgtgc ctgatagctt tcagtctgct aacaaatctc     540

ctttatgcag tttaacctct gtacttccaa tggggaggaa ttggaatcag cctatgggag     600

aagagatagc tctaggattc ttagggctga ttgttgagac actggtgaac tttgaacctc     660

tgtgatttcc ctgtttgctc tgtgcctgat agctttcagt ctgctaacaa atctccttta     720

tgcagtttaa cctctgtact tccaatgggg aggaattgga atcagcctat gggagaagag     780

atagctctag gattcagatc ttgctaccag tggaacagcc actaaggatt ctgcagtgag     840

agcagagggc cagctaagtg gtactctccc agagactgtc tgactcacgc caccccctcc     900

accttggaca caggacgctg tggtttctga gccaggtaca atgactcctt tcggtaagtg     960

cagtggaagc tgtacactgc ccaggcaaag cgtccgggca gcgtaggcgg gcgactcaga    1020

tcccagccag tggacttagc ccctgtttgc tcctccgata actggggtga ccttggttaa    1080

tattcaccag cagcctcccc cgttgcccct ctggatccac tgcttaaata cggacgagga    1140

cagggccctg tctcctcagc ttcaggcacc accactgacc tgggacagtg aatgcggccg    1200

ctgagaactt cagggtgagt ctatgggacc cttgatgttt tctttcccct tcttttctat    1260

ggttaagttc atgtcatagg aaggggagaa gtaacagggt acacatattg accaaatcag    1320

ggtaattttg catttgtaat tttaaaaaat gctttcttct tttaatatac tttttttgtt    1380

atcttatttc taatactttc cctaatctct ttctttcagg gcaataatga tacaatgtat    1440

catgcctctt tgcaccattc taaagaataa cagtgataat ttctgggtta aggcaatagc    1500

aatatttctg catataaata tttctgcata taaattgtaa ctgatgtaag aggtttcata    1560

ttgctaatag cagctacaat ccagctacca ttctgctttt attttatggt tgggataagg    1620

ctggattatt ctgagtccaa gctaggccct tttgctaatc atgttcatac ctcttatctt    1680

cctcccacag ctcctgggca acgtgctggt ctgtgtgctg gcccatcact ttggcaaagc    1740

acgtgagatc tgaattcgcc gccaccatgc tgtttaacct gagaatcctg ctgaataacg    1800

ctgcctttag gaacggacat aacttcatgg tccgcaactt tcgctgtggc cagcctctcc    1860

agaacaaagt gcagctgaag ggagagggacc tgctgaccct gaaaaatttc acaggagagg   1920

aaatcaagta catgctgtgg ctgtctgccg atctgaagtt ccggatcaag cagaagggcg    1980

aatatctgcc actgctccag ggcaaaagtc tggggatgat cttcgaaaag aggagtactc    2040

ggaccagact gtcaacagag actggattcg ctctgctggg aggacaccca tgctttctga    2100

ccacacagga cattcatctg ggcgtgaacg agtcactgac cgacacagcc cgggtgctga    2160
```

```
gcagcatggc cgatgccgtg ctggcacggg tctacaaaca gagcgacctg gataccctgg   2220
ctaaggaagc aagcatcccc atcattaatg ggctgtccga cctgtatcac cctatccaga   2280
ttctggccga ttacctgacc ctccaggagc attattctag tctgaaaggc ctgacactga   2340
gctggattgg ggacggaaac aatatcctgc actccattat gatgtctgcc gctaagtttg   2400
ggatgcacct ccaggcagcc acaccaaaag gctacgaacc cgatgccagt gtgactaagc   2460
tggccgaaca gtatgctaaa gagaacggca ctaagctgct gctgaccaat gacccccctgg  2520
aggctgcaca cggaggcaac gtcctgatca ctgatacctg gatcagcatg ggccaggagg   2580
aagagaagaa gaagcggctc caggccttcc agggctacca ggtgacaatg aaaactgcca   2640
aggtcgccgc ttctgattgg acttttctgc attgtctgcc ccgaaaacct gaagaggtgg   2700
acgatgaggt cttctattca cctaggagcc tggtgtttcc agaagccgag aatcgcaagt   2760
ggacaatcat ggccgtgatg gtgtccctgc tgactgacta ttccccacag ctgcagaagc   2820
ctaagttttg agatatcgtc gactcgctga tcagcctcga ctgtgccttc tagttgccag   2880
ccatctgttg tttgcccctc ccccgtgcct tccttgaccc tggaaggtgc cactcccact   2940
gtcctttcct aataaaatga ggaaattgca tcgcattgtc tgagtaggtg tcattctatt   3000
ctggggggtg gggtggggca ggacagcaag ggggaggatt gggaagacaa tagcaggcat   3060
gctggggatg cggtgggctc tatggcttct gaggcggaaa gaaccagctg gggctcgact   3120
agactagtcc tgcaggtaga gcatggctac gtaaggaacc cctagtgatg gagttggcca   3180
ctccctctct gcgcgctcgc tcgctcactg aggccgggcg accaaaggtc gcccgacgcc   3240
cgggctttgc ccgggcggcc tcagtgagcg agcgagcgcg cagagaggga gtggccaact   3300
ttttgcaaaa gcctaggcct ccaaaaaagc ctcctcacta cttctggaat agctcagagg   3360
ccgaggcggc ctcggcctct gcataaataa aaaaaattag tcagccatgg ggcggagaat   3420
gggcggaact gggcggagtt aggggcggga tgggcggagt taggggcggg actatggttg   3480
ctgactaatt gagatgcatg ctttgcatac ttctgcctgc tggggagcct ggggactttc   3540
cacacctggt tgctgactaa ttgagatgca tgctttgcat acttctgcct gctggggagc   3600
ctggggactt tccacaccct aactgacaca cattccacag ctgcattaat gaatcggcca   3660
acgcgcgggg agaggcggtt tgcgtattgg gcgctcttcc gcttcctcgc tcactgactc   3720
gctgcgctcg gtcgttcggc tgcggcgagc ggtatcagct cactcaaagg cggtaatacg   3780
gttatccaca gaatcagggg ataacgcagg aaagaacatg tgagcaaaag gccagcaaaa   3840
ggccaggaac cgtaaaaagg ccgcgttgct ggcgtttttc cataggctcc gcccccctga   3900
cgagcatcac aaaaatcgac gctcaagtca gaggtggcga aacccgacag gactataaag   3960
ataccaggcg tttccccctg gaagctccct cgtgcgctct cctgttccga ccctgccgct   4020
taccggatac ctgtccgcct ttctcccttc gggaagcgtg gcgctttctc atagctcacg   4080
ctgtaggtat ctcagttcgg tgtaggtcgt tcgctccaag ctgggctgtg tgcacgaacc   4140
ccccgttcag cccgaccgct gcgccttatc cggtaactat cgtcttgagt ccaacccggt   4200
aagacacgac ttatcgccac tggcagcagc cactggtaac aggattagca gagcgaggta   4260
tgtaggcggt gctacagagt tcttgaagtg gtggcctaac tacggctaca ctagaagaac   4320
agtatttggt atctgcgctc tgctgaagcc agttaccttc ggaaaaagag ttggtagctc   4380
ttgatccggc aaacaaacca ccgctggtag cggtggtttt tttgtttgca agcagcagat   4440
tacgcgcaga aaaaaaggat ctcaagaaga tcctttgatc ttttctacgg ggtctgacgc   4500
tcagtggaac gaaaactcac gttaagggat tttggtcatg agattatcaa aaaggatctt   4560
```

```
cacctagatc cttttaaatt aaaaatgaag ttttaaatca atctaaagta tatatgagta   4620
aacttggtct gacagttacc aatgcttaat cagtgaggca cctatctcag cgatctgtct   4680
atttcgttca tccatagttg cctgactccc cgtcgtgtag ataactacga tacgggaggg   4740
cttaccatct ggccccagtg ctgcaatgat accgcgagac ccacgctcac cggctccaga   4800
tttatcagca ataaaccagc cagccggaag ggccgagcgc agaagtggtc ctgcaacttt   4860
atccgcctcc atccagtcta ttaattgttg ccgggaagct agagtaagta gttcgccagt   4920
taatagtttg cgcaacgttg ttgccattgc tacaggcatc gtggtgtcac gctcgtcgtt   4980
tggtatggct tcattcagct ccggttccca acgatcaagg cgagttacat gatcccccat   5040
gttgtgcaaa aaagcggtta gctccttcgg tcctccgatc gttgtcagaa gtaagttggc   5100
cgcagtgtta tcactcatgg ttatggcagc actgcataat tctcttactg tcatgccatc   5160
cgtaagatgc ttttctgtga ctggtgagta ctcaaccaag tcattctgag aatagtgtat   5220
gcggcgaccg agttgctctt gcccggcgtc aatacgggat aataccgcgc cacatagcag   5280
aactttaaaa gtgctcatca ttggaaaacg ttcttcgggg cgaaaactct caaggatctt   5340
accgctgttg agatccagtt cgatgtaacc cactcgtgca cccaactgat cttcagcatc   5400
ttttactttc accagcgttt ctgggtgagc aaaaacagga aggcaaaatg ccgcaaaaaa   5460
gggaataagg gcgacacgga aatgttgaat actcatactc ttcctttttc aatattattg   5520
aagcatttat cagggttatt gtctcatgag cggatacata tttgaatgta tttagaaaaa   5580
taaacaaata ggggttccgc gcacatttcc ccgaaaagtg ccacctgacg tctaagaaac   5640
cattattatc atgacattaa cctataaaaa taggcgtatc acgaggccct ttcgtctcgc   5700
gcgtttcggt gatgacggtg aaaacctctg acacatgcag ctcccggaga cggtcacagc   5760
ttgtctgtaa gcggatgccg ggagcagaca agcccgtcag ggcgcgtcag cgggtgttgg   5820
cgggtgtcgg ggctggctta actatgcggc atcagagcag attgtactga gagtgcacca   5880
ttcgacgctc tcccttatgc gactcctgca ttaggaagca gcccagtagt aggttgaggc   5940
cgttgagcac cgccgccgca aggaatggtg catgcaagga gatggcgccc aacagtcccc   6000
cggccacggg gcctgccacc atacccacgc cgaaacaagc gctcatgagc ccgaagtggc   6060
gagcccgatc ttccccatcg gtgatgtcgg cgatataggc gccagcaacc gcacctgtgg   6120
cgccggtgat gccggccacg atgcgtccgg cgtagaggat ctg                      6163
```

<210> SEQ ID NO 33
<211> LENGTH: 20
<212> TYPE: DNA
<213> ORGANISM: Artificial sequence
<220> FEATURE:
<223> OTHER INFORMATION: OTC forward primer

<400> SEQUENCE: 33

```
cgatgccagt gtgactaagc                                                  20
```

<210> SEQ ID NO 34
<211> LENGTH: 20
<212> TYPE: DNA
<213> ORGANISM: Artificial sequence
<220> FEATURE:
<223> OTHER INFORMATION: OTC reverse primer

<400> SEQUENCE: 34

```
ggagccgctt cttcttctct                                                  20
```

```
<210> SEQ ID NO 35
<211> LENGTH: 19
<212> TYPE: DNA
<213> ORGANISM: Artificial sequence
<220> FEATURE:
<223> OTHER INFORMATION: GAPDH forward primer

<400> SEQUENCE: 35

acggcaaatt caacggcac                                                    19


<210> SEQ ID NO 36
<211> LENGTH: 20
<212> TYPE: DNA
<213> ORGANISM: Artificial sequence
<220> FEATURE:
<223> OTHER INFORMATION: GAPDH reverse primer

<400> SEQUENCE: 36

tagtggggtc tcgctcctgg                                                   20
```